(12) United States Patent
Skelton

(10) Patent No.: US 11,576,806 B2
(45) Date of Patent: Feb. 14, 2023

(54) ADJUSTABLE FINGER SPLINT

(71) Applicant: Andrew C. Skelton, Austin, TX (US)

(72) Inventor: Andrew C. Skelton, Austin, TX (US)

( * ) Notice: Subject to any disclaimer, the term of this patent is extended or adjusted under 35 U.S.C. 154(b) by 214 days.

(21) Appl. No.: 16/486,042

(22) PCT Filed: Jan. 31, 2019

(86) PCT No.: PCT/US2019/015939
§ 371 (c)(1),
(2) Date: Aug. 14, 2019

(87) PCT Pub. No.: WO2019/152576
PCT Pub. Date: Aug. 8, 2019

(65) Prior Publication Data
US 2020/0390583 A1    Dec. 17, 2020

Related U.S. Application Data

(60) Provisional application No. 62/624,375, filed on Jan. 31, 2018.

(51) Int. Cl.
A61F 5/058    (2006.01)

(52) U.S. Cl.
CPC .............................. A61F 5/05866 (2013.01)

(58) Field of Classification Search
CPC .......... A61F 5/05866; A61F 2005/0172; A61F 2005/0179; A61F 5/10; A61F 5/013; A61F 5/0118; A61F 5/01; A61F 5/05875; A61F 5/058; A61F 5/04; A61F 5/048; A61F 5/042
See application file for complete search history.

(56) References Cited

U.S. PATENT DOCUMENTS

| | | | | |
|---|---|---|---|---|
| 2,646,794 A * | 7/1953 | Baer | ................... | A61F 5/05875 602/22 |
| 4,220,334 A * | 9/1980 | Kanamoto | ............. | A63B 23/16 601/40 |
| 4,384,571 A | 5/1983 | Nuzzo et al. | | |
| 4,456,002 A * | 6/1984 | Barber | ................ | A61F 5/05866 482/44 |
| 4,558,694 A | 12/1985 | Barber | | |

(Continued)

FOREIGN PATENT DOCUMENTS

| | | | | |
|---|---|---|---|---|
| GB | 1326351 | 8/1973 | | |
| WO | WO-9945864 A1 * | 9/1999 | ............. | A61F 5/013 |

OTHER PUBLICATIONS

European Office Action dated Sep. 8, 2020 for European Patent Application No. 19705649.2, a counterpart foreign application of U.S. Appl. No. 16/486,042, 3 pages.

(Continued)

Primary Examiner — Tarla R Patel
(74) Attorney, Agent, or Firm — Lee & Hayes, P.C.

(57) ABSTRACT

An adjustable finger splint having a main body and slide. The slide configured to move relative to the main body and including a wedge to apply variable pressure to an injured finger to cause the injured finger to extend or straighten. The main body having a proximal interphalangeal platform to support the proximal interphalangeal joint, a metacarpophalangeal platform to support the palm and metacarpophalangeal joint, and a slide platform to support the slide.

20 Claims, 44 Drawing Sheets

(56) References Cited

U.S. PATENT DOCUMENTS

| | | | |
|---|---|---|---|
| 4,665,905 A * | 5/1987 | Brown | A61F 5/0106 602/16 |
| D310,263 S | 3/1990 | Ellis | |
| 4,944,290 A * | 7/1990 | Hepburn | A61F 5/05875 602/22 |
| D310,883 S | 9/1990 | Ellis | |
| 5,038,764 A * | 8/1991 | Paez | A61F 5/0118 602/30 |
| 5,136,743 A * | 8/1992 | Pirela-Cruz | A61B 6/0421 378/208 |
| 5,197,943 A | 3/1993 | Link | |
| 5,232,436 A | 3/1993 | Janevski | |
| 5,328,448 A * | 7/1994 | Gray, Sr. | A61H 1/0288 601/40 |
| 5,372,145 A * | 12/1994 | Berger | A61F 5/3723 602/20 |
| 5,547,463 A * | 8/1996 | Hinchliffe | A61B 90/00 600/102 |
| 6,561,995 B1 | 5/2003 | Thibodo, Jr. | |
| 6,575,925 B1 | 6/2003 | Noble | |
| 7,878,997 B2 | 2/2011 | Bolla | |
| 8,070,702 B2 * | 12/2011 | Farrell | A61F 5/05866 602/5 |
| D715,951 S | 10/2014 | Stuart | |
| D843,589 S | 3/2019 | Han | |
| D844,153 S | 3/2019 | Han | |
| 10,363,158 B1 | 7/2019 | Rhinier | |
| 2014/0267116 A1 | 9/2014 | Weiner | |
| 2017/0281386 A1 | 10/2017 | Salido, III | |
| 2019/0175376 A1 * | 6/2019 | Peisner | A61H 1/0274 |

OTHER PUBLICATIONS

European Office Action dated Sep. 1, 2022 for European Patent Application No. 19705649.2, a foreign counterpart to U.S. Appl. No. 16/486,042.

* cited by examiner

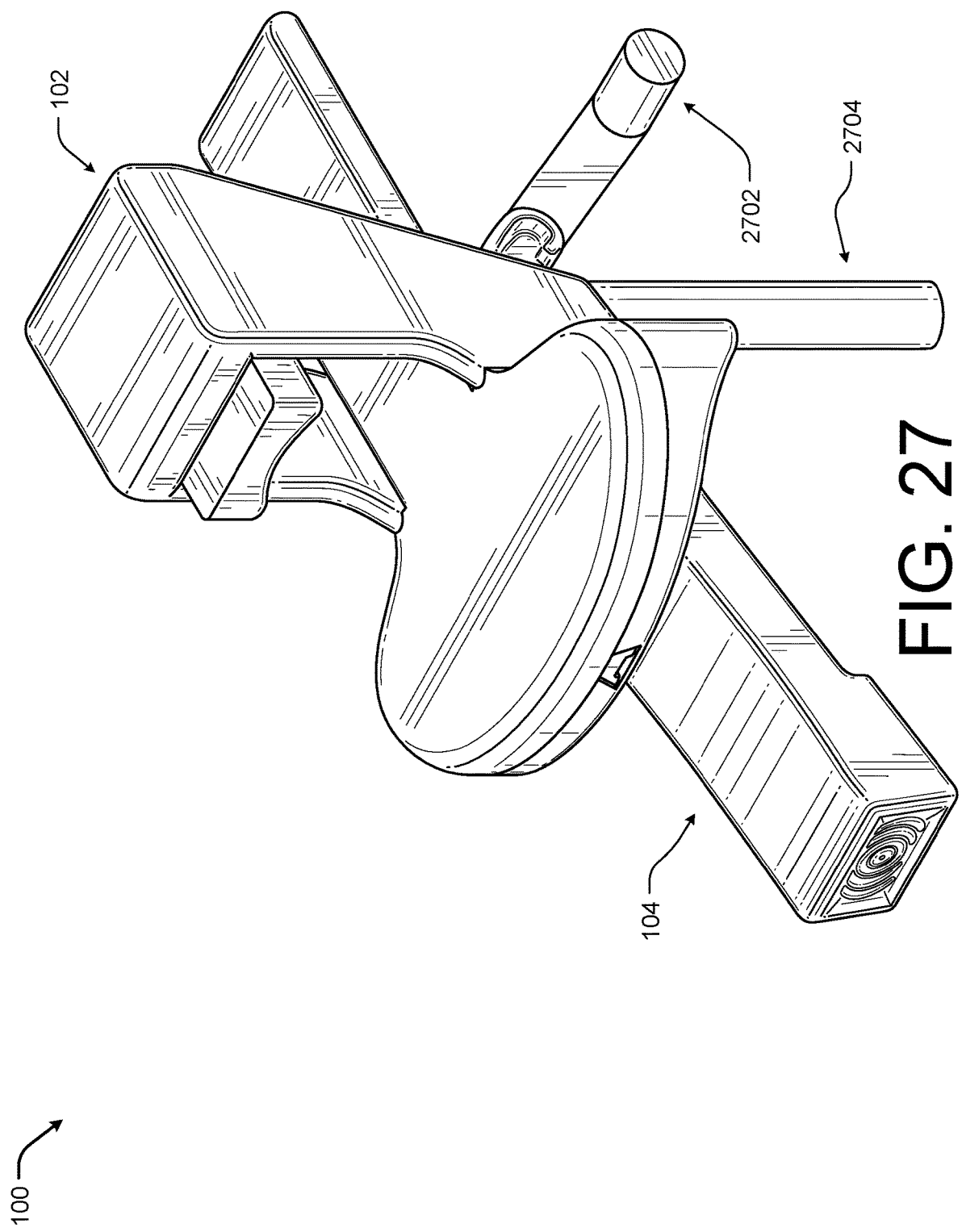

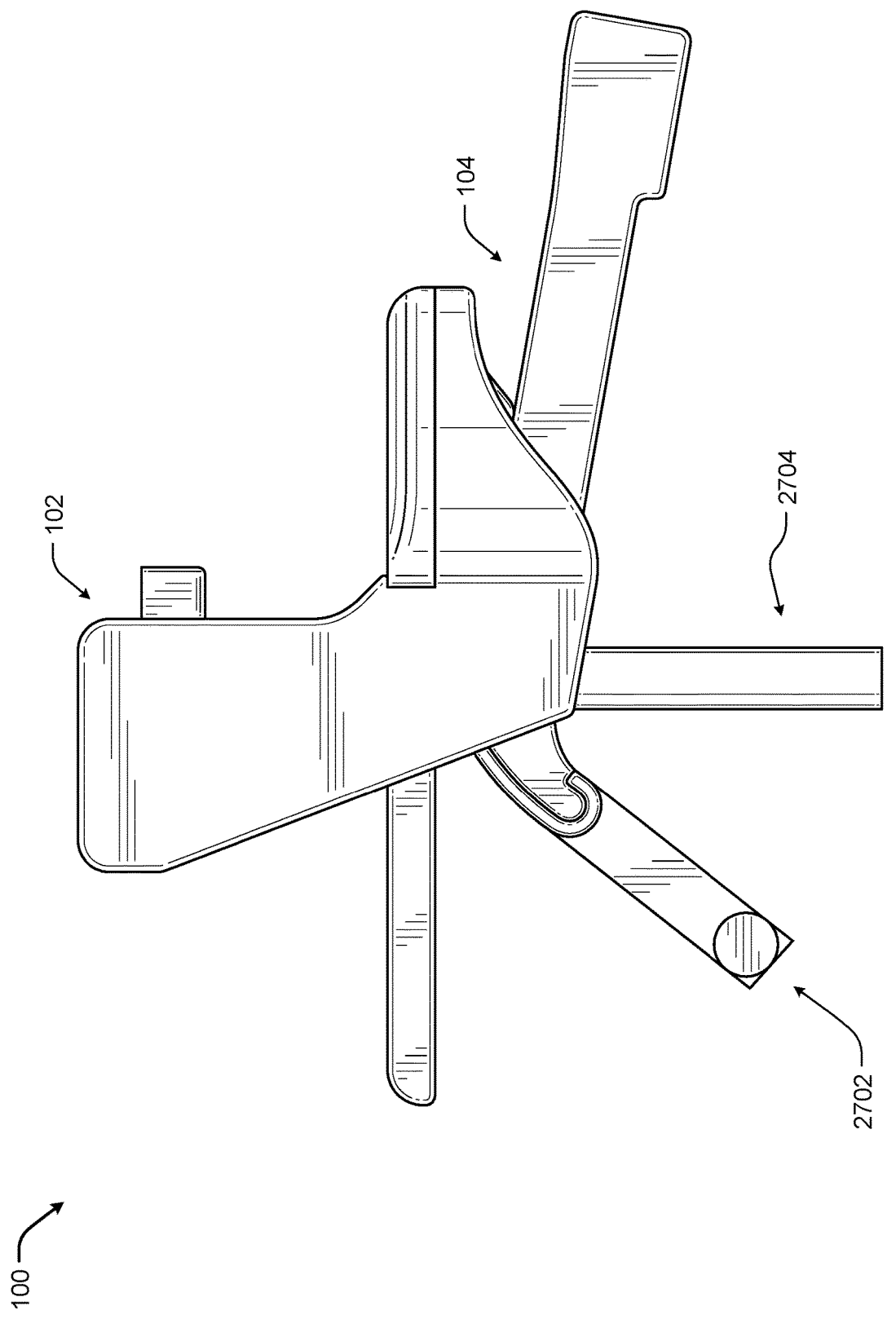

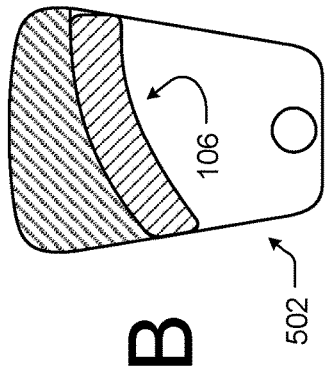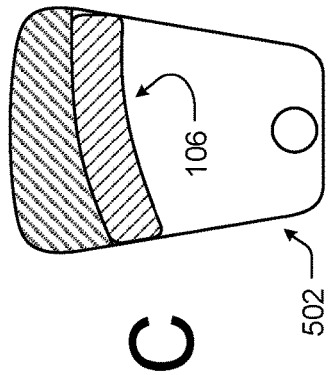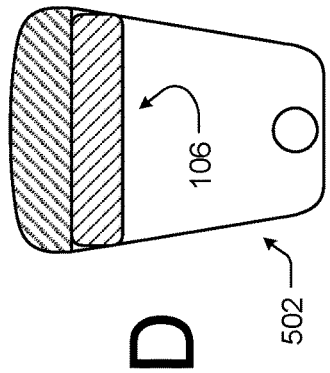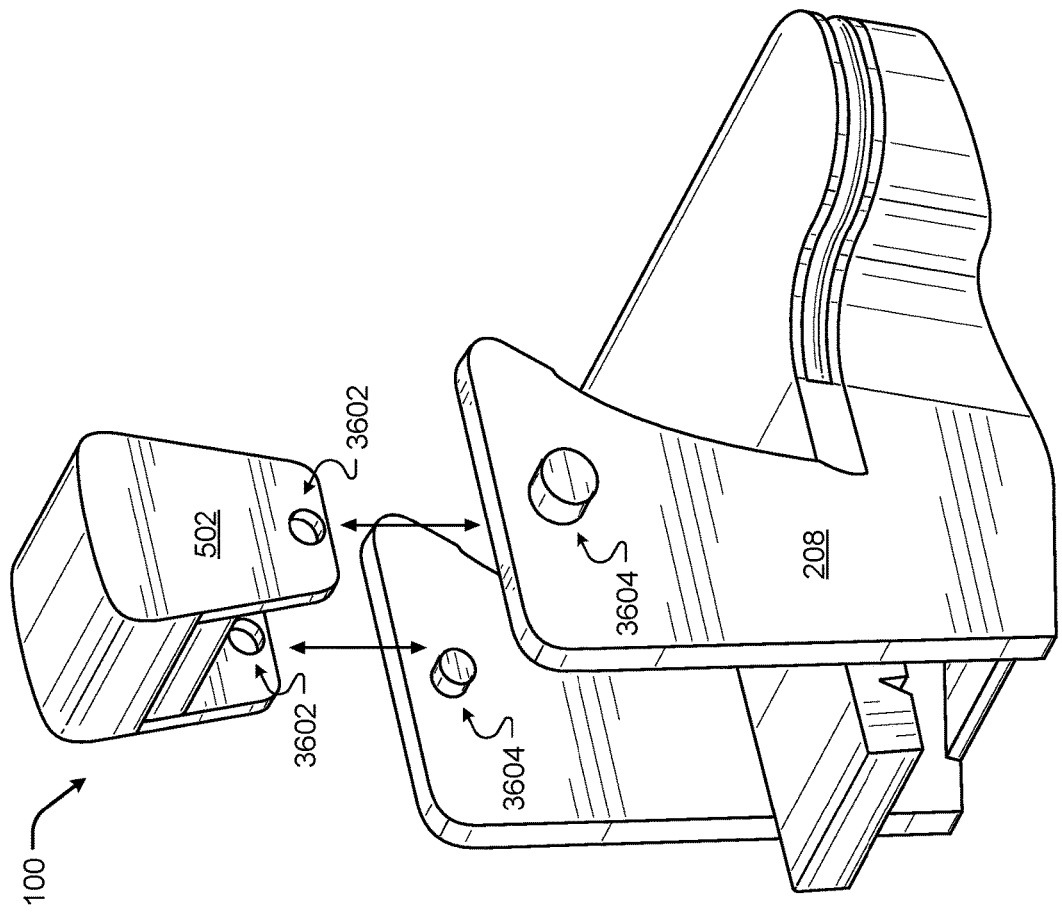

ADJUSTABLE FINGER SPLINT

CROSS-REFERENCE TO RELATED APPLICATION(S)

This application is a national stage application of international patent application PCT/US19/15939 filed Jan. 31, 2019, which claims priority to U.S. Provisional Application No. 62/624,375 filed on Jan. 31, 2018 entitled "ADJUSTABLE FINGER SPLINT," the entire contents of which are incorporated herein by reference.

BACKGROUND

A human hand has numerous bones, including phalanges and metacarpals. Each finger has three phalanges: a proximal phalange, an intermediate phalange, and a distal phalange. A thumb has two phalanges. Phalanges are hinged together with interphalangeal joints. For example, a finger's proximal phalange and intermediate phalange are joined by a proximal interphalangeal (PIP) joint, while a finger's intermediate phalange and distal phalange are joined by a distal interphalangeal (DIP) joint. A finger's proximal phalange is joined to a metacarpal with a metacarpophalangeal (MCP) joint.

Unfortunately, accidents or other medical conditions can impact the flexion and/or extension of a finger's interphalangeal joints. For example, when a tendon used to extend a finger becomes torn while another tendon used to pull the finger toward the palm of the hand remains intact, the finger can become contracted against the palm. Treatment of such an injured finger can involve bracing the finger into a desired position while the finger heals. Some devices have been developed that use screws to move parts into place to brace an injured finger. However, conventional devices fail to achieve sufficed magnitude of force or rigidity on the finger.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

FIG. 27 depicts an example perspective view of an adjustable finger splint usable by a third-party according to some implementations.

FIG. 28 depicts an example side view of the adjustable finger splint of FIG. 27 according to some implementations.

FIG. 36A depicts an example perspective view of an adjustable finger splint with adjustable proximal interphalangeal platform according to some implementations.

FIG. 36B depicts an example side view of an adjustable proximal interphalangeal platform according to some implementations.

FIG. 36C depicts an example side view of an adjustable proximal interphalangeal platform according to some implementations.

FIG. 36D depicts an example side view of an adjustable proximal interphalangeal platform according to some implementations.

DETAILED DESCRIPTION

Figure 1:
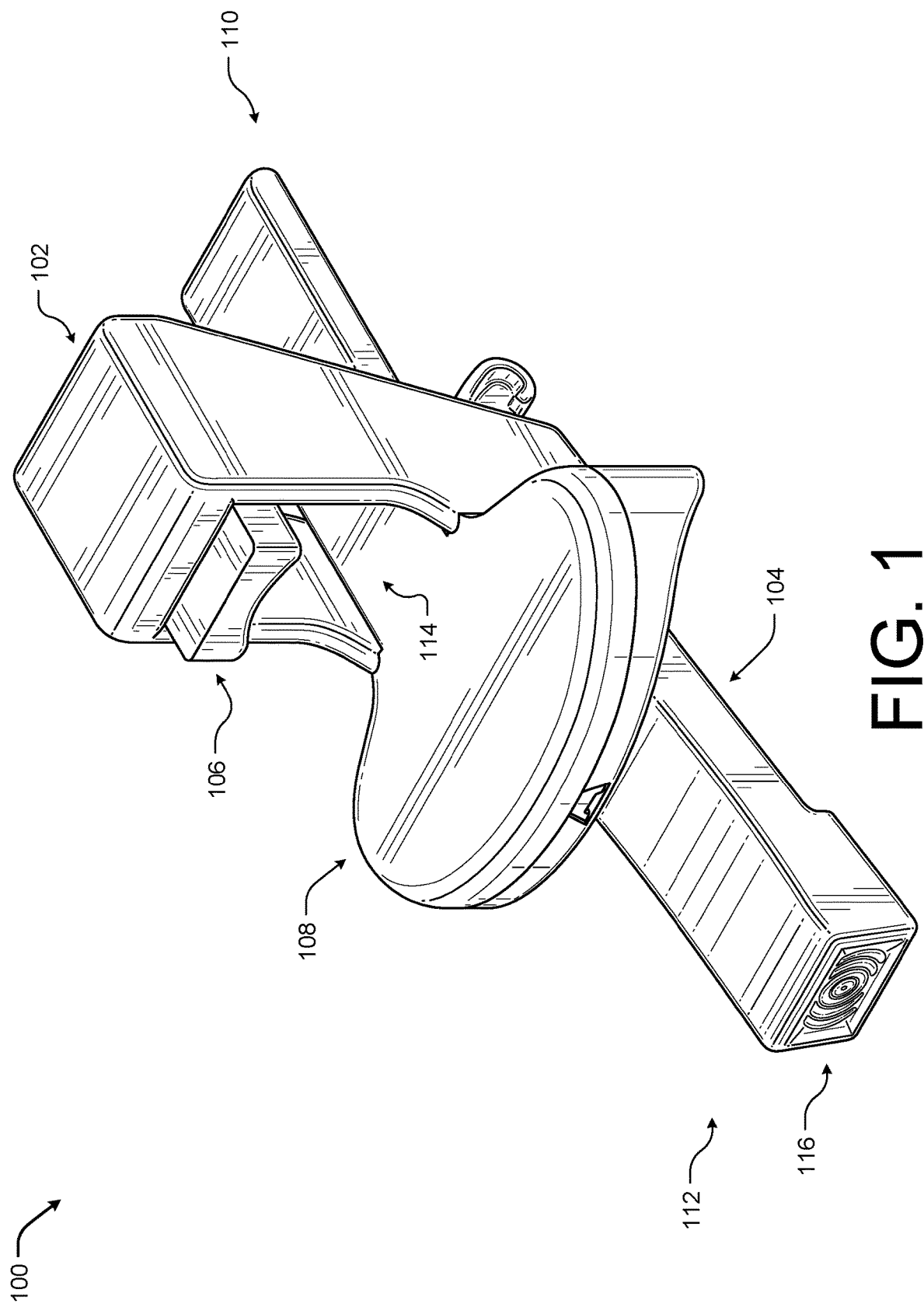
FIG. 1 depicts an example perspective view of an example adjustable finger splint according to some implementations.

This disclosure includes systems and implementations for providing an adjustable finger splint usable to treat various finger related injuries. For example, age, injury, or damage to one or more of the figures may cause the fingers to stiffen or lock in a bent or flexed position. For instance, damage or injury to the extensor tendons or ligaments in the finger often cause the finger to lock in a bent or flexed position due to force exerted by the flexor tendons on the finger. In this instance, if the injury remains untreated the finger may remain permanently in a flexed position. However, conventional treatments including casting the finger locks the finger in an extended position for long periods of time. Therefore, the adjustable finger splint discussed herein provides for a splint that allows the user to remove the finger from the splint when the user's pain threshold is elapsed as well as for the user to self-adjust the amount of pressure applied by the splint at any time during use, thereby, allowing the injury to be treated without the need for continuous casting or long recovery times due to surgery.

In some cases, the adjustable finger splint may include a self-contained unit or may be formed as an assembly of two or more separate components. The adjustable finger splint may include a main body that may be permanently or releasably coupled to a slide. The main body may have a front end positioned away from the user during use and a rear end, opposite the front end, or positioned proximate to the user during use. The main body may also include an opening or cavity configured to receive a finger of the user and to hold the finger in place during treatment or use. When the finger is secured within the opening, the user's finger may be positioned such that the end of the user's finger is proximate the front end and the palm of the user is proximate the rear end.

A slide may be movable, adjustable, or slidable relative to the main body of the finger splint, and, thus movable, adjustable, or slidable relative to the injured finger held immobile by the main body. In these cases, the slide may be used to increase or decrease the pressure applied to the end of the finger by adjusting the position of the slide relative to the main body. In some implementations, the slide may have a wedge that is configured to apply increasing pressure on the end of the finger held within the main body as the slide is pushed or pulled outwards towards the front end of the main body. In this manner, as the slide is moved away from the body of the user, a curvature of the wedge forces the finger further and further toward a fully extended position. Thus, in some examples, the user may gradually reduce the angle of the injured finger relative to the hand (e.g., further straighten the finger) over a period of treatment (e.g., days, weeks, or months depending on the severity of the injury).

In some implementations, the slide may be releasably coupled to the main body, such that the slide may be removed or separated from the main body when not in use and, thus, allow for the adjustable finger splint to be more easily stored or carried. In alternative implementations, the finger splint may be configured to prevent loss of the independent components of the splint and, thus while the palm side may be movable or adjustable with respect to the main body, the slide may be affixed, such as via a track, to the main body. In these alternative implementations, the slide and the main body may be inseparable. In some cases, the slide and/or the main body may be formed form a substantially rigid material, such as various plastics, polymers, metals, alloys, polyurethanes, gases, fluids, gels, foams, fibers, or combinations thereof.

As discussed above, the adjustable finger splint may include two or more substantially rigid components that apply pressure to an injured finger in a manner to hold the finger in a straighten or extended position. However, in some situations, direct contact between the substantially rigid material of the main body and slide of the splint may result in pain levels that exceeds the tolerance thresholds of the individual being treated, even for a short duration. Thus, the adjustable finger splint may also include a dorsal pad and a palmar pad to increase comfort and reduce pain caused by the finger splint to the user when in use. In some cases, the palmar pad may be secured to the slide below the hand of the user and the dorsal pad may be secured along a bottom of a top surface of the opening within the main body of the adjustable finger splint in a position above the finger. In some cases, either or both of the dorsal pad and the palmar pad may be formed from a material, such as polyurethanes, elastomers, etc.

In some cases, injury to one or more fingers may be caused by age or be one of numerous injuries stained by the user. In these cases, the user may be unable to apply necessary force to the slide to cause the injured finger to extend. Thus, in some implementations, the adjustable finger splint may be designed, such that a third-party (e.g., physical therapist, hand therapist, doctor, surgeon, nurse, or other medical professional) is able to adjust the slide relative to the main body. In these implementations, the slide may include a pull or handle proximate to the front end that the third-party may use to adjust the slide relative to the main body. The main body may also include a grip or other stabilizing portion that the third-party may utilize to substantially maintain the position of the main body when adjusting the position of the slide. In one particular implementation, the main body may be weighted such that when the adjustable finger splint is set or rests on a table or other surface, the main body preserves its position as the palm side is moved.

In some cases, the finger splint may also be configured to allow the user or other medical professional to measure the angle of the finger relative to the hand of the user both at rest and during use of the splint. For instance, in some implementations, the adjustable finger splint may include a window such that the user or the medical professional may utilize a protractor or other tool to measure the relative angles between the finger and hand. In other implementations, the protractor may be built into the splint, such as printed along the window, or the main body may include an extended portion that may mirror the position of the finger within the opening of the main body. In still other implementations, the adjustable finger splint may include a dial that may be turned to adjust the position of the slide relative to the main body and also provide or determine the relative angle of the finger and hand.

FIG. 1 depicts an embodiment of an adjustable finger splint 100. The adjustable finger splint 100 may comprise a main body 102, a slide 104, a dorsal pad 106, and a palmar pad 108, as discussed above. As illustrated, the finger splint 100 may include a front 110 and a back 112. In the illustrated example, the front 110 is positioned away from the user during use and the back 112, opposite the front 110, is positioned proximate to or facing the body of the user during use.

As discussed above, the main body may also include an opening or cavity, generally indicated by 114, configured to receive a finger of the user during treatment or use. When the finger is secured within the finger opening 114, the user's finger may be resting on the palmar pad 108, such that the end of the user's finger is proximate the front 110 and the palm of the user is proximate the back 112. The user may then push on a back end 116 of the slide 104, to cause the slide 104 to move in a direction towards the front 110 of the splint 100. As the palmar pad 108 is flexible, the inserted finger may force the palmar pad 108 downward such that it bends down to rest atop the slide 104. The slide 104 may push the palmar pad 108 and the finger of the user upwards as the slide 104 is moved towards the front 110. As the palmar pad 108 and the finger are extended upward the finger may contact the dorsal pad 106. The dorsal pad 106 and the main body 102 apply pressure in opposite directions (e.g., upward and downward respectively) on the finger causing the finger to extend and straighten. As the position of the slide 104 relative to the main body 102 may be moved or adjusted to increase or decrease the pressure applied to the end of the finger, the user may set the pressure load based on the discomfort that the user is experiencing (e.g., by increasing the pressure, the effect of the treatment is increased but so is the discomfort).

In the illustrated example, both the main body 102 and the slide 104 are substantially rigid, such that the splint 100 may apply opposing pressure on a finger placed within the finger opening 114 of the main body 102. However, in some situations, direct contact between the substantially rigid material of the main body 102 and slide 104 may result in increased pain levels that exceeds the tolerance thresholds of the individual being treated, even for a short duration. Thus, in the illustrated implementation, the adjustable finger splint 100 may also include the dorsal pad 106 and the palmar pad 108 to increase comfort and reduce pain caused by the finger splint 100 during use. It should be understood that in other implementations, the dorsal pad 106 and the palmar pad 108 may be optional or removable. For instance, the dorsal pad 106 and/or the palmar pad 108 may wear out or occasionally need to be replaced. In these instances, by including a removable dorsal pad 106 and palmar pad 108, the entire splint 100 does not have to be discarded when the pads 106 and 108 are worn out. In some situations, the thickness and/length of either or both of the dorsal pad 106 or the palmar pad 108 may be adjusted or custom sized to fit the intended user. In these situations, by including removable dorsal pads 106 and palmar pads 108, the main body 102 and the slide 104 may be stock to reduce manufacturing costs of the splint 100.

Figure 2:
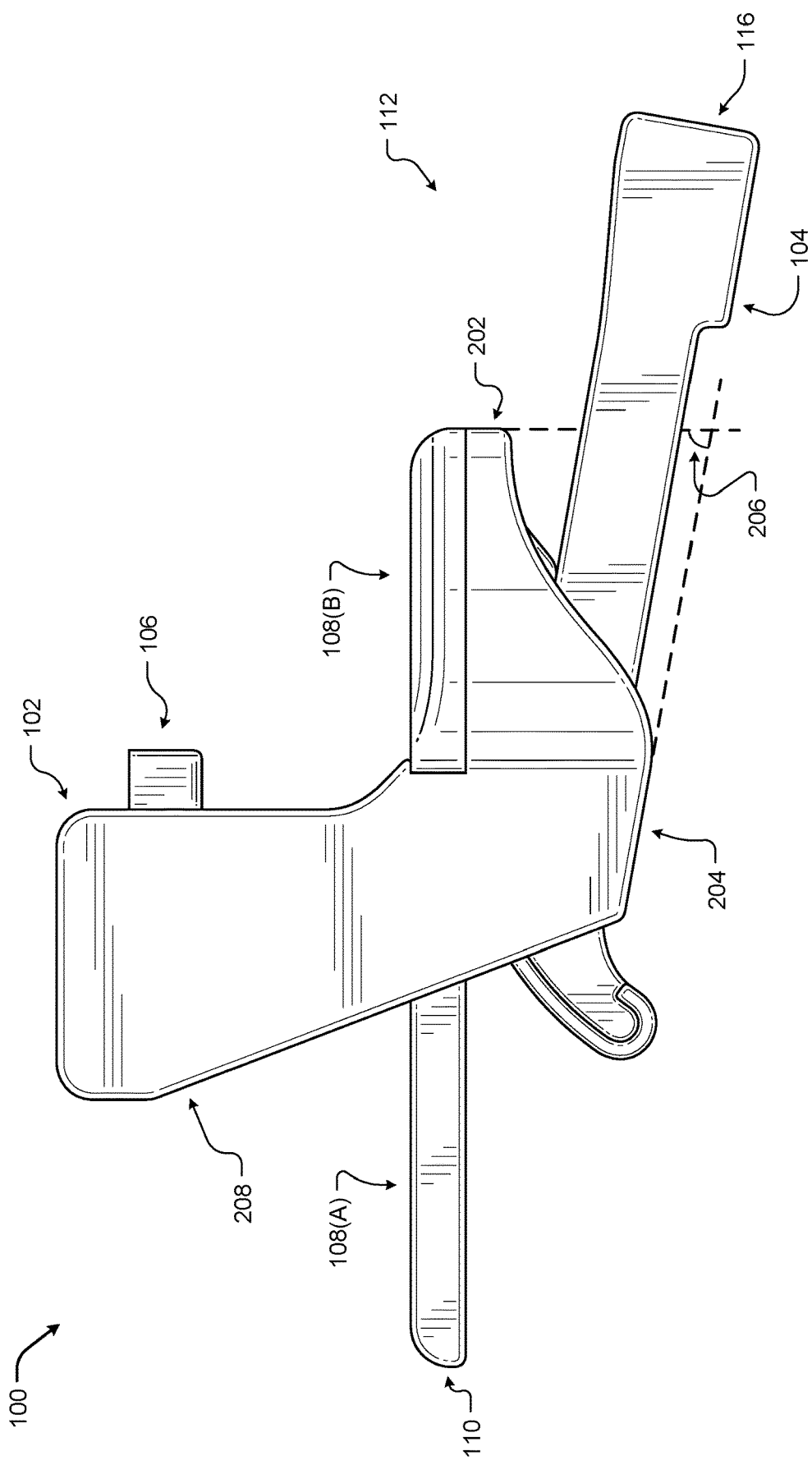
FIG. 2 depicts an example left side view of the adjustable finger splint of FIG. 1 according to some implementations.

FIG. 2 depicts an example left side view of the adjustable finger splint 100 of FIG. 1 according to some implementations. In the illustrated example, the finger splint 100 again includes two rigid or hard component, the main body 102 and the slide 104, as well as two pads, the dorsal pad 106 and the palmar pad 108. In this example, a finger of a user may be placed between the dorsal pad 106 and the palmar pad 108, such that the finger of the user rests on the front portion of the palmar pad 108(A) and the palm of the user rests on the rear portion of the palmar pad 108(B) during use. In this implementation, the main body 104 includes a metacarpophalangeal (MCP) platform 202 that is configured to support the rear portion of the palmar pad 108(B) and, thereby, maintain the palm of the user in a fixed position during use. In some implementations, a frame 208 may extend upward from the MCP platform 202. The frame 208 may be configured to support a PIP platform (not shown) over the finger of the user when the splint 100 is in use. The PIP platform may be configured to couple to the Dorsal pad 106 and maintain the Dorsal pad 106 above the finger being treated. In the illustrated example, the MCP platform 202 may be integral to the frame 208, however, in some implementations the MCP platform 202 and/or frame 208 may be configured to decouple from each other, such that different sized MCP platforms 202 and/or frames 208 may be selected based on the specific finger, anatomical measurements of the injured hand, the characteristics associated with the palmar pad 108 (such as thickness of the padding, material type, number of layers, etc.), and/or the characteristics of the associated with the dorsal pad 106 (e.g., as thickness of the padding, material type, number of layers, etc.).

In the current example, the main body 102 may have a slide platform 204 extending between walls of the frame 208. The slide platform 204 may support the slide 104 during use and include a top surface (not shown) that is included at a predetermined angle relative 206 to the MCP platform 202. The relative angle of the incline of the slide platform 204 to the MCP platform 202 causes the slide 104 to engage the palmar pad 108 in a manner that lifts the front end of the palmar pad 108 at an angle complementary to the relative angle 206 between the MCP platform 202 and the slide platform 204, as discussed below with respect to FIG. 4 in more detail.

Figure 3:
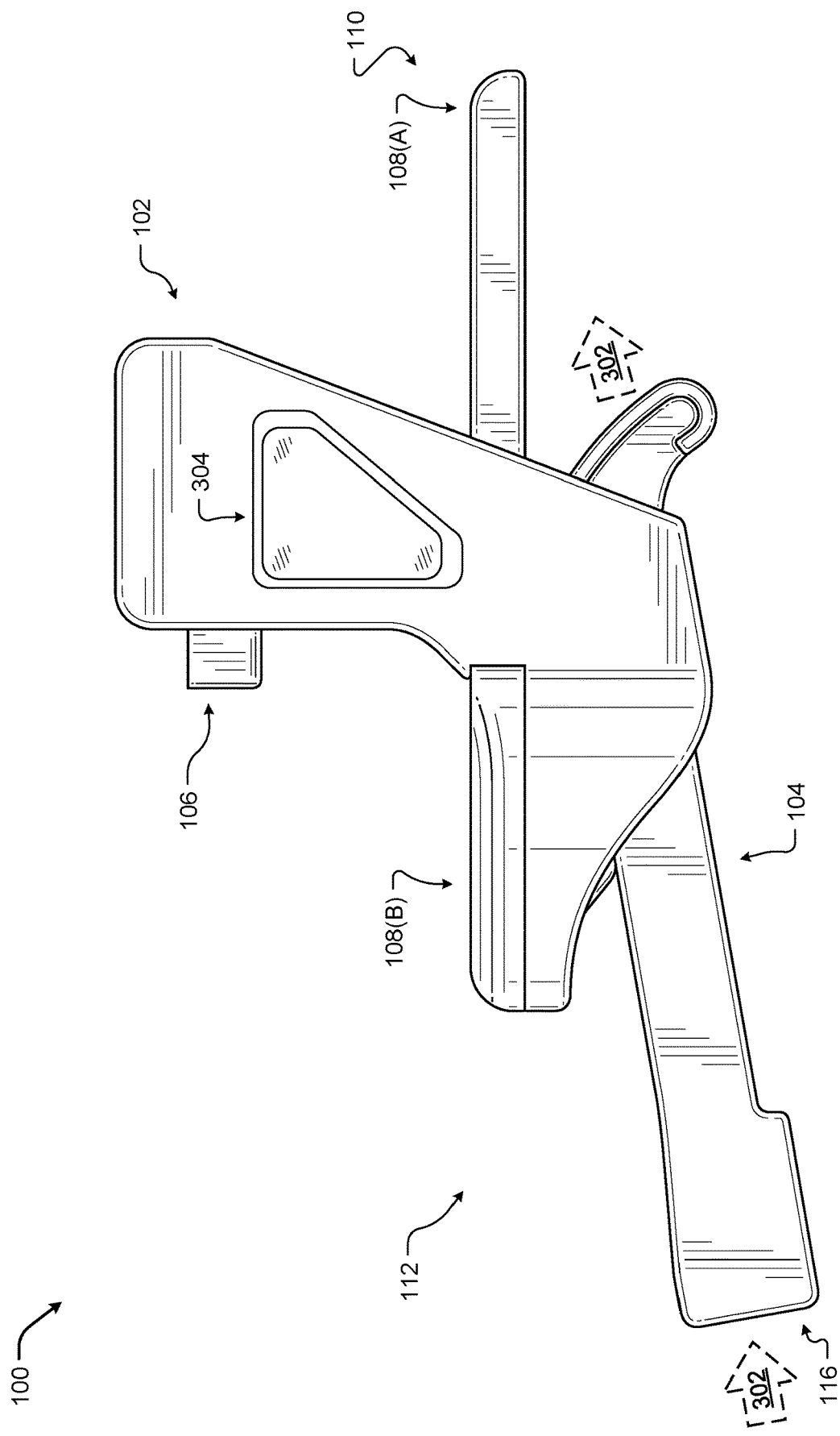
FIG. 3 depicts an example right side view of the adjustable finger splint with the palm side in initial or loose position of FIG. 1 according to some implementations.

FIG. 3 depicts an example right side view of the adjustable finger splint 100 with the palm side 104 in initial or loose position of FIG. 1 according to some implementations. In this example, once the user's hand is engaged with the splint 100 (e.g., the palm of the user is resting on the rear portion of the palmar pad 108(B) and the finger being treated is resting on the front portion of the palmar pad 108(A)), the user may apply forward pressure, generally indicated by arrows 302, on the slide 104 by pushing on the back end 116 of the slide 104 to cause the slide 104 to move forward (e.g., toward the front end 110 of the splint 100) and, thereby, raising the front portion of the palmar pad 108(A) upwards, as illustrated below with respect to FIG. 4.

In the illustrated example, the main body 102 may also include a window 304. The window 304 may allow the user and/or a medical professional to view the position or angle of the finger during treatment. For example, the user and/or a medical professional may utilize a tool (e.g., a protractor) to measure the relative angle of the finger during treatment and, thereby, gage a level of affect or improvement (e.g., relative straightening of the finger) experienced by the user. In some cases, the window 304 may include markings (e.g., degrees) that may be used to measure the relative angle of the finger without the use of additional tools.

Figure 4:
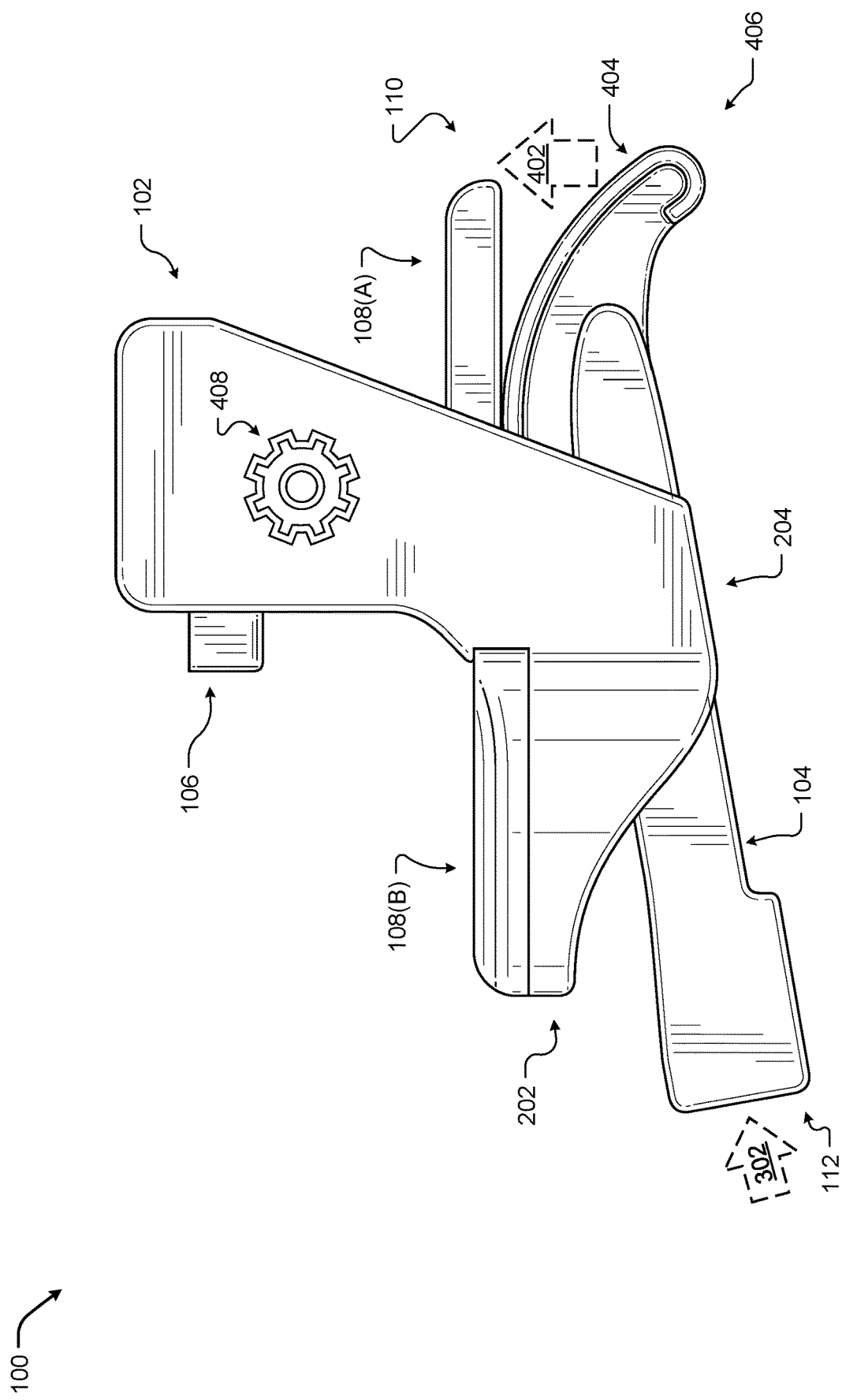
FIG. 4 depicts an example right side view of the adjustable finger splint of FIG. 1 with slide in an engaged position according to some implementations.

FIG. 4 depicts an example right side view of the adjustable finger splint 100 of FIG. 1 with slide 104 in an engaged position according to some implementations. As discussed above with respect to FIG. 3, the user may apply forward pressure 302 on the back end 116 of the slide 104 to cause the slide 104 to engage with the front portion of the palmar pad 108(A). As illustrated when the slide 104 is engaged with the front end of the palmar pad 108(A), the front end of the palmar pad 108(A) is raised upward toward the dorsal pad 106. Thus, in the engaged position, the dorsal pad 106 applies a downward or stabling pressure on the proximal phalanx and the front end of the palmar pad 108(A) applies an opposite upward pressure on the distal phalanx (or the end of the finger), causing the finger to extend as the MCP joint and the PIP joint are straightened. By maintaining force on the joint at maximum extension, the contracted tissues are elongated and mobility is restored. However, by allowing the user to apply the pressure 302 to the slide 104, the user is able to control the amount of time spent applying the treatment and, in some situations, to remove the hand from the splint 100, allowing the user use of the hand and a break from the treatment.

As discussed above, the main body 102 may include a slide platform 204 that has an incline that is at a predetermined angle (not shown) relative to the MCP platform 202. The relative angle of the incline of the slide platform 204 to the MCP platform 202 causes the slide 104 to engage the palmar pad 108 in a manner that lifts the front end of the palmar pad 108(A) at an angle complementary to the relative angle between the MCP platform 202 and the slide platform 204. In the current example, the slide 104 also has a wedge 404 positioned proximate to a front end 406 of the slide 104. The wedge 404 has a curvature that is configured to cause the finger to straighten as the slide 104 is pushed towards the front end 110. Thus, in the illustrated implementation, the finger of the user is forced into the extended position in part due to the relative angle between the incline of the top surface of the slide platform 204 and the MCP platform and in part based on the curvature of the wedge 404. The radius of the curvature of the wedge 404 is calibrated to maintain the DIP joint in a neutral position throughout the range of extension of the slide 104.

In the illustrated example, the main body 102 may also include a measuring device 408. As discussed above, the splint 100 may include a window to allow the user and/or a medical professional to view the position or angle of the finger during treatment. In this example, the splint 100 may include a measuring device 408 that may indicate the angle or straightness of the finger being treated. For example, the measuring device 408 may be mechanically coupled to a component that is adjusted based on contact or position of the slide 104. In this example, the measuring device 408 may rotate to provide an indication of the angle or straightness of the finger being treated as the slide 104 is adjusted. It should be understood that in other examples, the measuring device 408 may take other forms.

Figure 5:
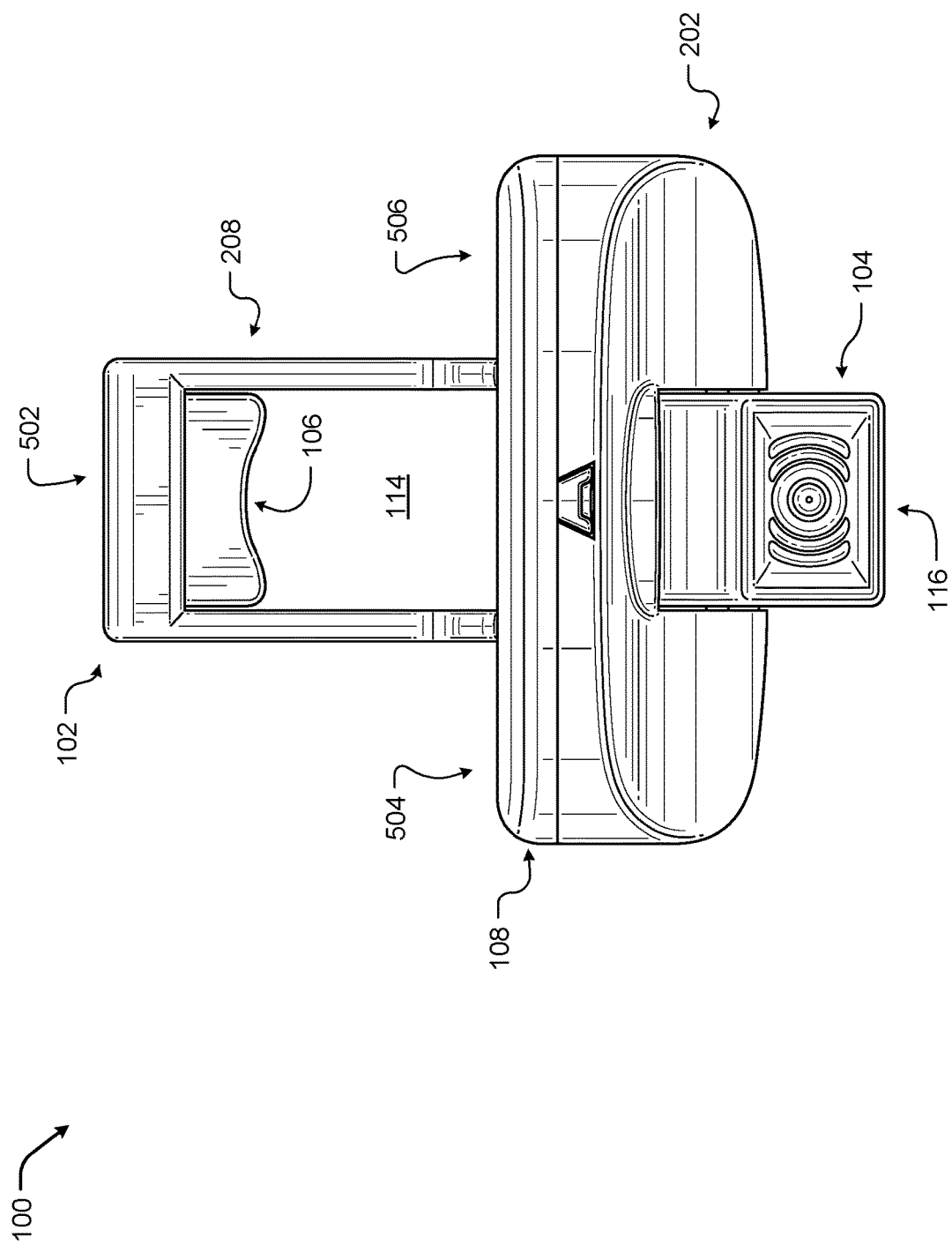
FIG. 5 depicts an example rear view of the adjustable finger splint of FIG. 1 according to some implementations.

FIG. 5 depicts an example rear view of the adjustable finger splint 100 of FIG. 1 according to some implementations. As discussed above, the main body 102 includes a frame 208 that supports a PIP platform 502. The frame 208 and the PIP platform 502 of the main body 102 forms a finger opening 114 to receive a finger of the user as discussed above. In the illustrated example, the dorsal pad 106 may be secured or adhered to the PIP platform 502 and the palmar pad 108 may be secured or adhered to the MCP platform 202 as shown. For example, various types of adhesive may be used to affix the dorsal pad 106 to the underside of the PIP platform 502 and the palmar pad 108 to the top surface of the MCP platform 202.

In the illustrated example, the back end 116 of the finger splint 104 may be textured or patterned to allow for increased friction when the user pushes or applies pressure to the back end 116 of the slide 104. It should be understood, that the finger splint 100 may be operated by the user with one hand. For example, the user may grip a front (not shown) of the MCP platform 202 using healthy fingers, generally at locations 504 and/or 506, while engaging the back end 116 of the slide 104 using the thumb.

Figure 6:
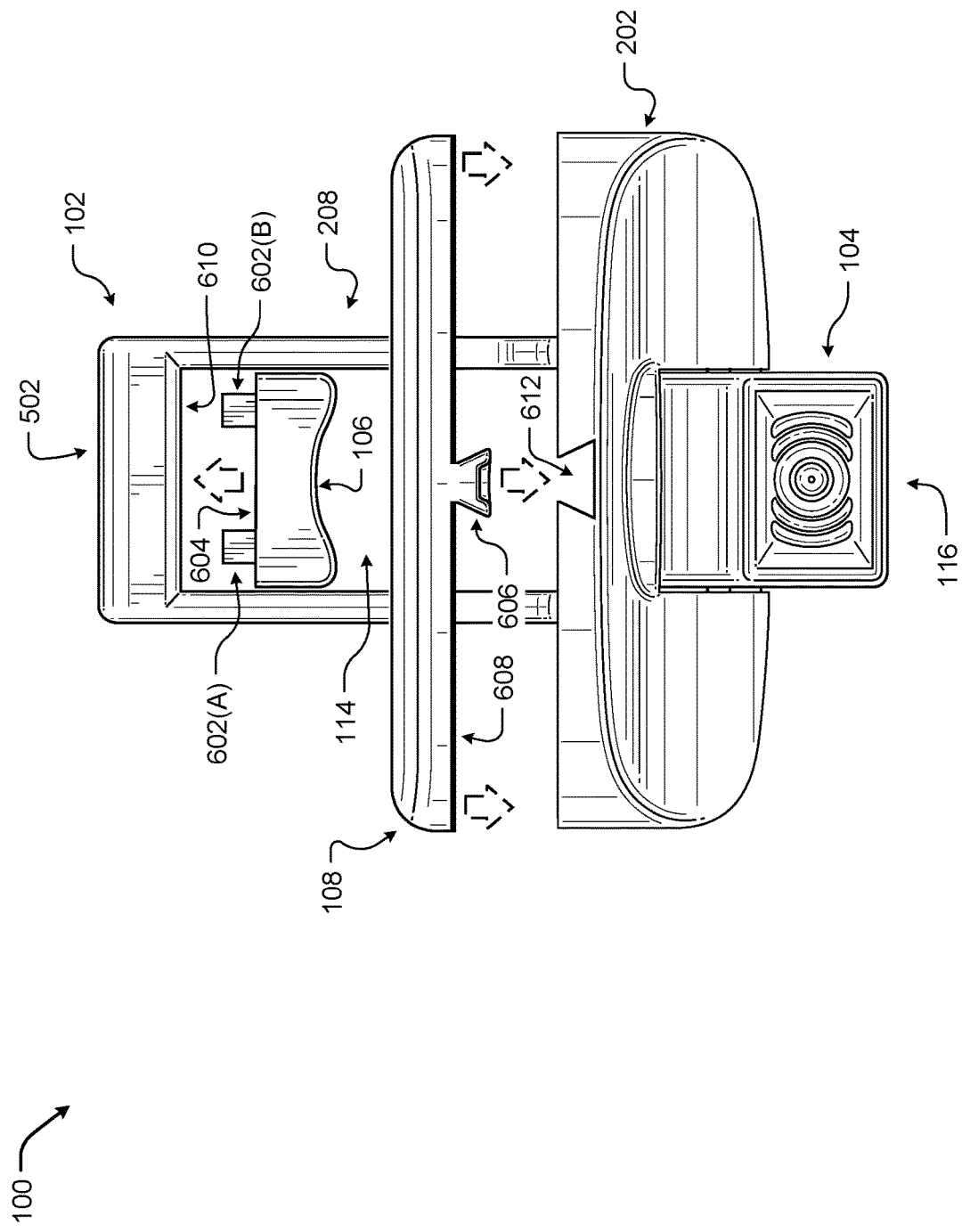
FIG. 6 depicts another example rear view of the adjustable finger splint 100 of FIG. 1 according to some implementations.

FIG. 6 depicts another example rear view of the adjustable finger splint 100 of FIG. 1 according to some implementations. In the current example, the dorsal pad 106 and the palmar pad 108 have been removed from the main body 102. In some situations, the pads 106 and/or 108 may wear at a faster rate than the main body 102 and/or the slide 104 or the thickness of the dorsal pad 106 and/or the palmar pad 108 may be selected or adjusted based on the needs of the individual being treated. For instance, some individuals may have hands thinner than others. These individuals may require the use of larger dorsal pads 106 and/or palmar pads 108. Thus, such as in the illustrated example, in some implementations, the dorsal pad 106 and/or the palmar pad 108 may releasably couple to the main body 102.

In the current example, the dorsal pad 106 may include one or more coupling components 602 that extend upwards from a top surface 604 of the body of the dorsal pad 106, such that the coupling components 602 may be received by corresponding receptacles (not shown) over the finger opening 114 along a bottom surface 610 of the PIP platform 502. In some implementations, the dorsal pad 106 may include two coupling components, such as left coupling components 602(A) and right coupling components 602(B). In some examples, the coupling components 602 may include a locking or mating member that may secure the dorsal pad 106 to the main body 102. In some implementations, such as the illustrated example, the dorsal pad 106 may be secured by friction between the coupling components 602 and the corresponding receptacles within the bottom surface 610 of the PIP platform 502. In some implementations, the bottom surface of the dorsal pad 106 may be contoured to receive the top surface of the finger of the user to provide increased comfort. In some implementations the dorsal pad 106 may be coupled in a manner that allows its position to be adjusted for the fit and comfort of the user, as will be discussed in more detail below.

The palmar pad 108 may also include one or more coupling components 606 that extend downward from a bottom surface 608 of the body of the palmar pad 108. For example, the MCP platform 202 may include a receptacle 612 for receiving the coupling component 606. In this example, the receptacle 612 may open to the back 112 of the MCP platform 202 such that the coupling component 606 may be pushed or slide into the receptacle 612 from the back 112 of the splint 100. In some instances, the receptacle 612 may extend along at least a portion of the MCP platform 202, such that the front of the coupling component 606 abuts a back surface (not shown) of the receptacle 612 to resist forward movement caused by pressure on the back end 116 of the slide 104 and maintain the palmar pad 108 on the MCP platform 202. In these examples, the coupling component 606 and receptacle 612 may have corresponding angled walls such that the coupling component 606 may resist upward movement caused by pressure of the slide 104 on the front end of the palmar pad 108, as discussed above.

Figure 7:
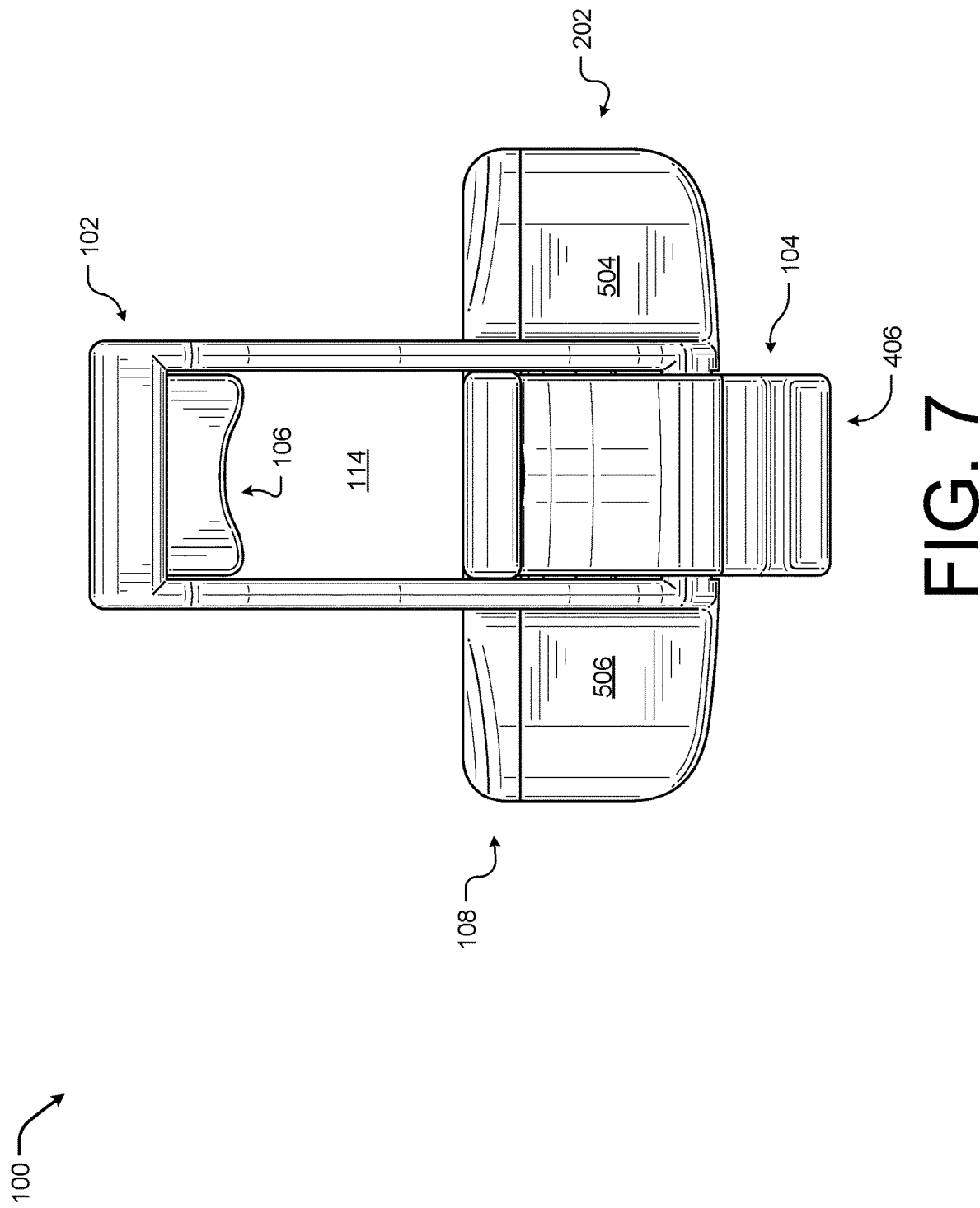
FIG. 7 depicts an example front view of the adjustable finger splint of FIG. 1 according to some implementations.

FIG. 7 depicts an example front view of the adjustable finger splint 100 of FIG. 1 according to some implementations. In the current example, the slide 104 is at rest or has not been engaged with the palmar pad 108. In this example, the main body 102 includes the finger opening 114 to receive the finger of the user prior to engaging the slide 104 with the palmar pad 108. In the illustrated implementation, a front of the MCP platform 202 is visible. In this illustrated implementation and as discussed above, the user may place one or more healthy fingers at locations 504 and 506 to provide apply a backwards pressure when the user pushes the slide 104 forward. In some cases, the locations 504 and 506 may include a texture or grip that provides increased frictions and allows the user to more easily apply the backwards pressure on the MCP platform 202.

Figure 8:
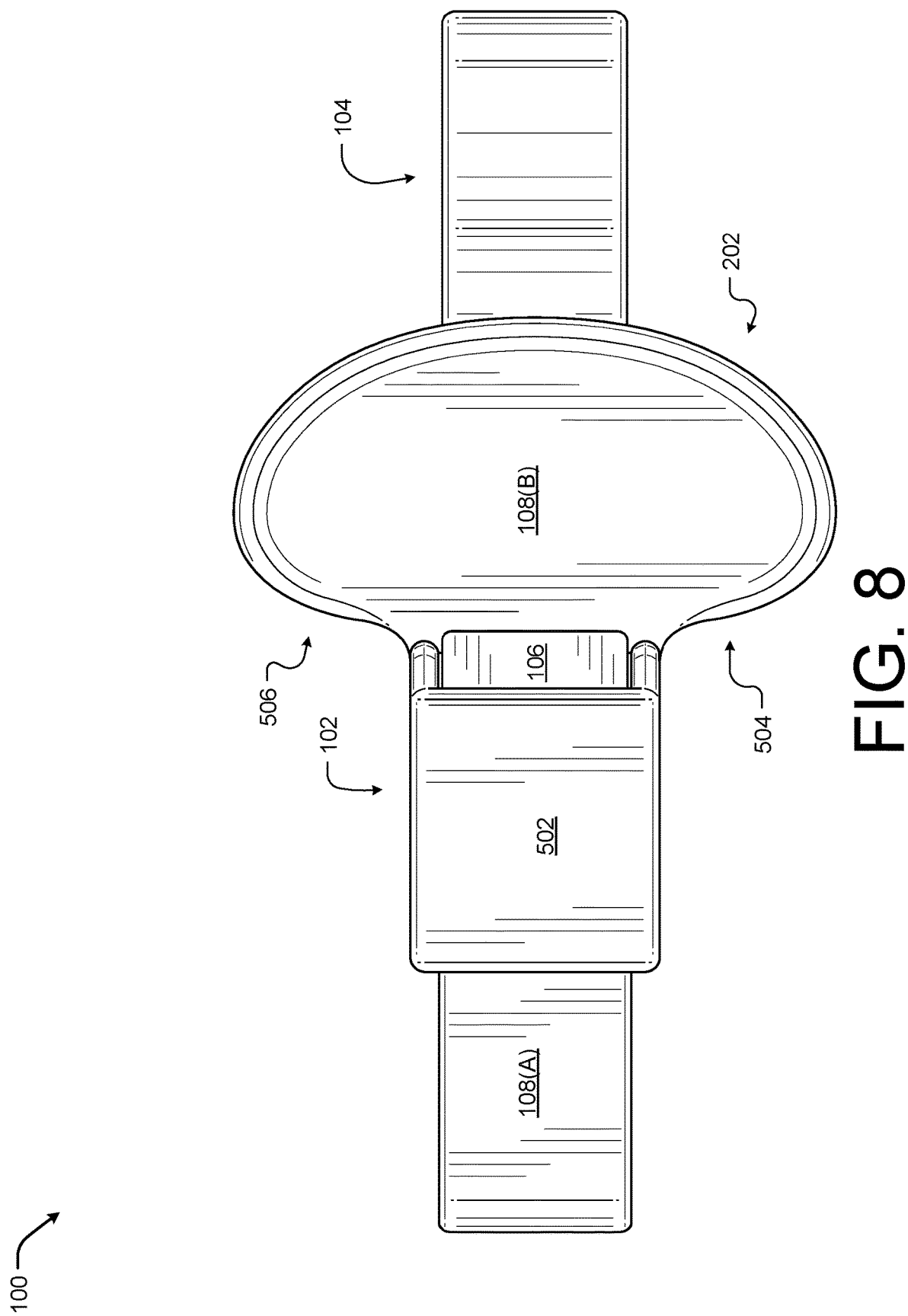
FIG. 8 depicts an example top view of the adjustable finger splint of FIG. 1 according to some implementations.

FIG. 8 depicts an example top view of the adjustable finger splint 100 of FIG. 1 according to some implementations. In the current example, the dorsal pad 106 and the palmar pad 108 are in place and the slide 104 is currently in the at rest position. As shown, the back portion of the palmar pad 108(A) may cover the surface of the MCP platform 202 and the palmar pad 108 may then extend through and out of the main body 102, as illustrated by the front end of the palmar pad 108(A). As the palmar pad 108 is formed from a flexible material the front end of the palmar pad 108(A) may flex upwards when in contract with the slide 104.

The dorsal pad 106 is secured to the bottom surface or underside of the PIP platform 502. In the current example, the dorsal pad 106 may extend past a front or rear edge of the PIP platform 502 to allow the user or other individual to pinch and remove the dorsal pad 106 from the main body 102 by pulling downward on the dorsal pad 106.

Figure 9:
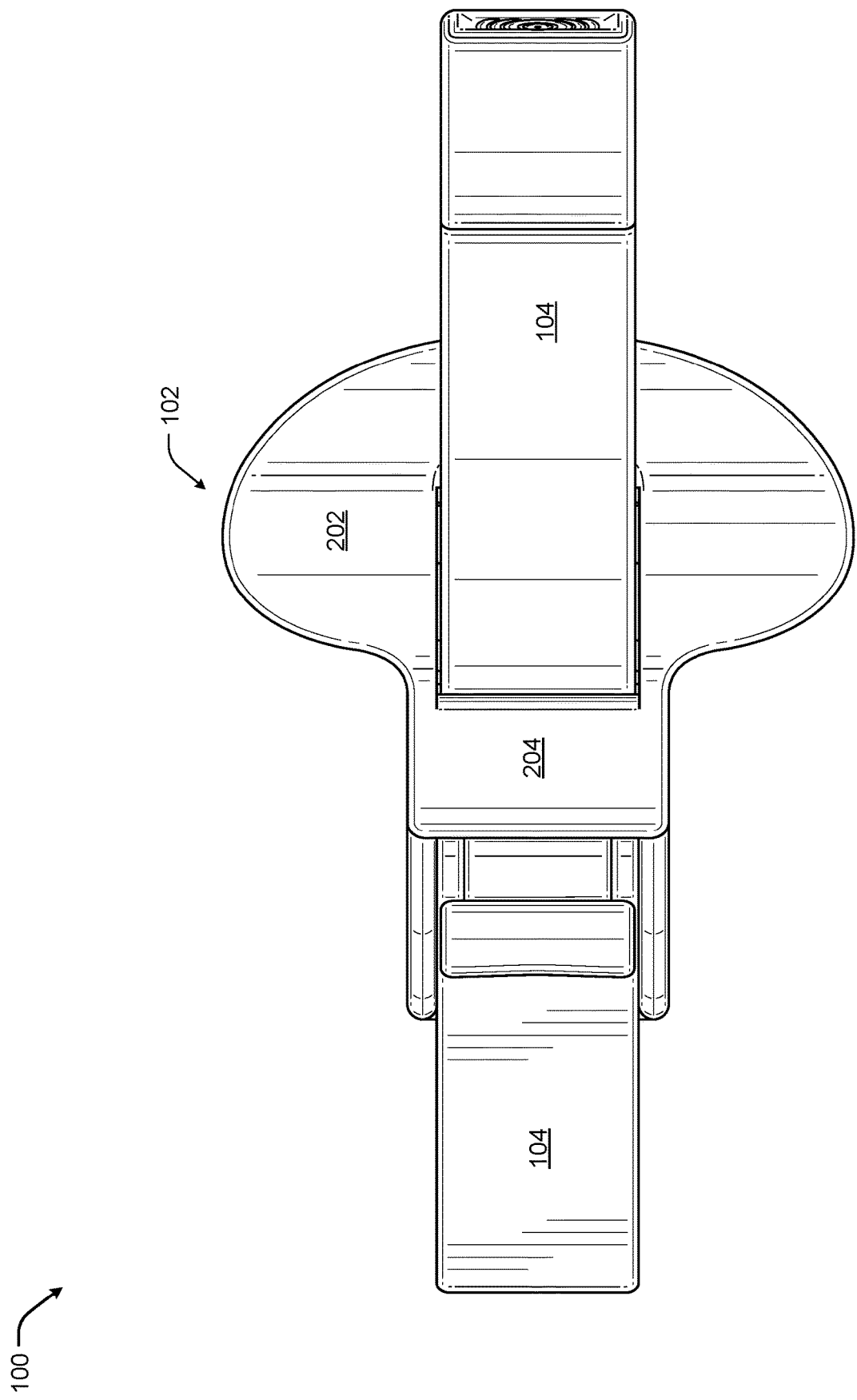
FIG. 9 depicts an example bottom view of the adjustable finger splint of FIG. 1 according to some implementations.

FIG. 9 depicts an example bottom view of the adjustable finger splint 100 of FIG. 1 according to some implementations. As illustrated, the slide 104 is resting on the slide platform 204. As discussed above, the slide platform 204 has a top surface (e.g., the surface in contact with the slide 104 and not shown) that includes an incline at a predetermine angle relative to the MCP platform 202.

Figure 10:
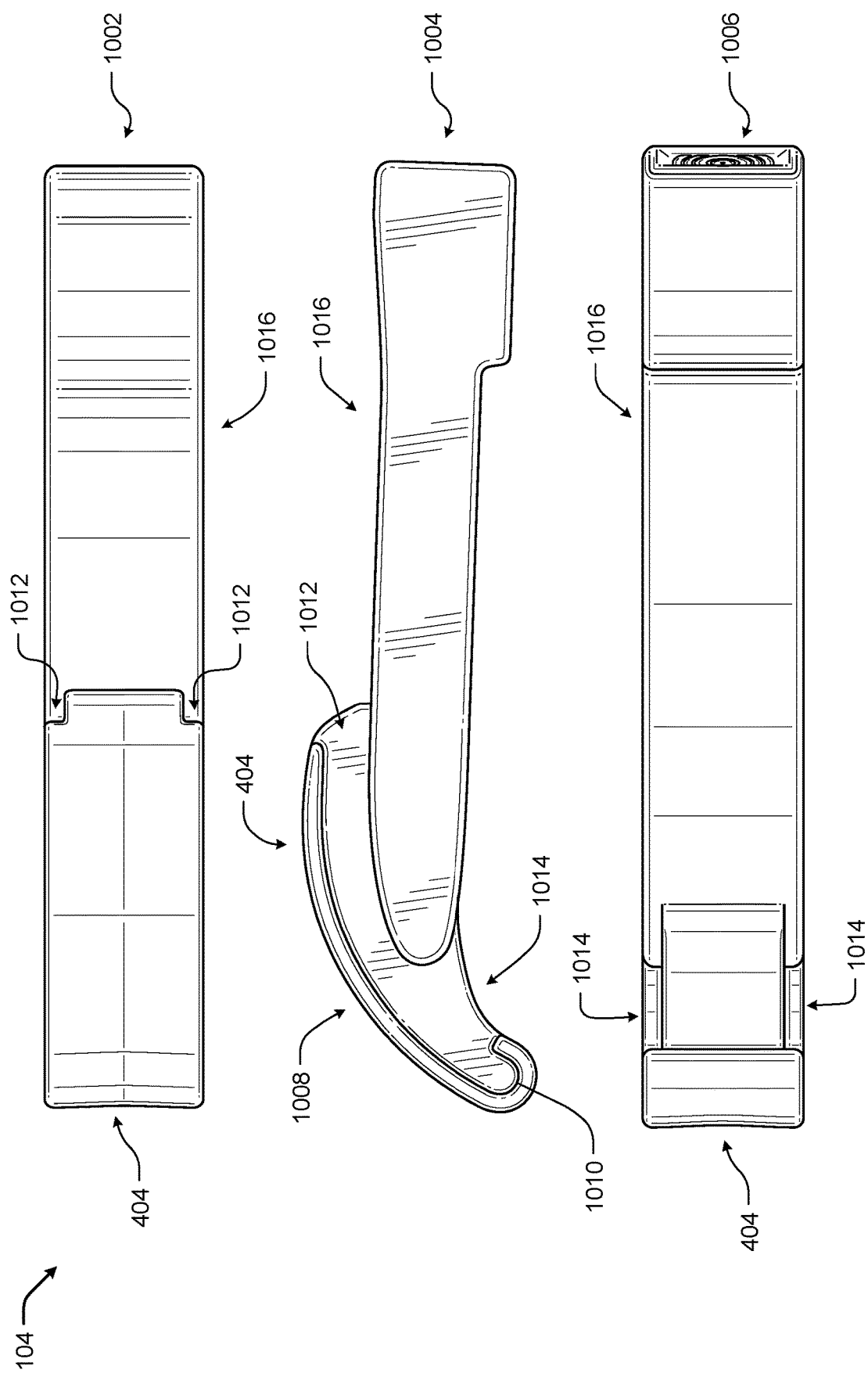
FIG. 10 depicts an example top view, side view, and bottom view of the slide of the adjustable finger splint of FIG. 1 according to some implementations.

FIG. 10 depicts an example top view 1002, side view 1004, and bottom view 1006 of the slide 104 of FIG. 1 according to some implementations. As discussed above, in some implementations, the slide 104 may be releasably coupled to the main body 102 of FIGS. 1-9, such that the slide 104 may be removed or separated from the main body 102 when not in use and, thus, allow for the adjustable finger splint 100 to be more easily stored or carried. In the illustrated example, the slide 104 includes a slide rail 1016 and a wedge 404 having a predefined curvature 1008. The curvature 1008 of the wedge 404 causes the finger to gradually extend or straighten as the slide 104 is moved in a direction towards the front end 110 of the splint 100. The curvature 1008 having a radius of between approximately 3.0 centimeters (cm) and 5.0 cm. In one particular example, the radius of the curvature 1008 may be 4.0 cm.

The wedge 404 also includes a lip or edge 1010 that forms a groove or recessed portion 1012 along either side of the wedge 404. The main body may include two locking members that may be received into the recessed portion 1012 via an opening 1014 on either side of the slide 104. In some examples, the slide 104 may be coupled with the main body 102 by placing the locking members into the recessed portion 1012. Then when the palmar pad 108 may be coupled to the main body 102 over the slide 104, such that the palmar pad 108 prevents the slide 104 from decoupling from the main body 102. In this manner, the slide 104 is less likely to decouple or become lost.

In some implementations, the length (e.g., the distance between a back end 116 and a front end 406) of the slide 104 may be between approximately 9.0 cm and 10 cm. In one particular example, the length of the slide 104 may be 10.3 cm. The wedge 404 may also have a length that is between one-third and one-fourth the length of the slide 104 and the slide rail 1016 may have length between two-third and three-fourths of the length of the slide 104. For example, the wedge 404 may be between 3.0 cm and 4.0 cm long and the slide rail 1016 may be between 6.0 cm and 7.0 cm. In one particular example, the wedge 404 may have a length of 4.6 cm and the slide rail may have a length of 6.4 cm. The slide rail 1016 may also have a height of between approximately 1.0 cm and 2.0 cm and a width between approximately 1.5 cm and 2.5 cm. The wedge 404 may have a height of between approximately 2.0 cm and 3.0 cm and a width between approximately 1.5 cm and 2.5 cm. In some cases, the width of the slide rail 1016 and the wedge 404 may be the same or equal to the size of the slide opening 1102 in the main body 102, as discussed below with respect to FIG. 11.

In some examples, the slide 104 may be formed as a single component or unit. The slide 104 may be formed from a rigid material, such as various plastics, polymers, polyethylene terephthalate, among others. In some cases, the slide 104 may have a shore D average hardness rating of between approximately 75 and 85.

In the current example, the slide 104 is illustrated as removed from the main body 102. However, it should be understood in other alternative implementations, the finger splint 100 may be configured to prevent loss of the independent components of the splint 100 and, thus the palm side 104 may be movable or adjustable with respect to the main body 102 but affixed (e.g., via a track) to the main body 102, such that the splint 100 is a single unit.

Figure 11:
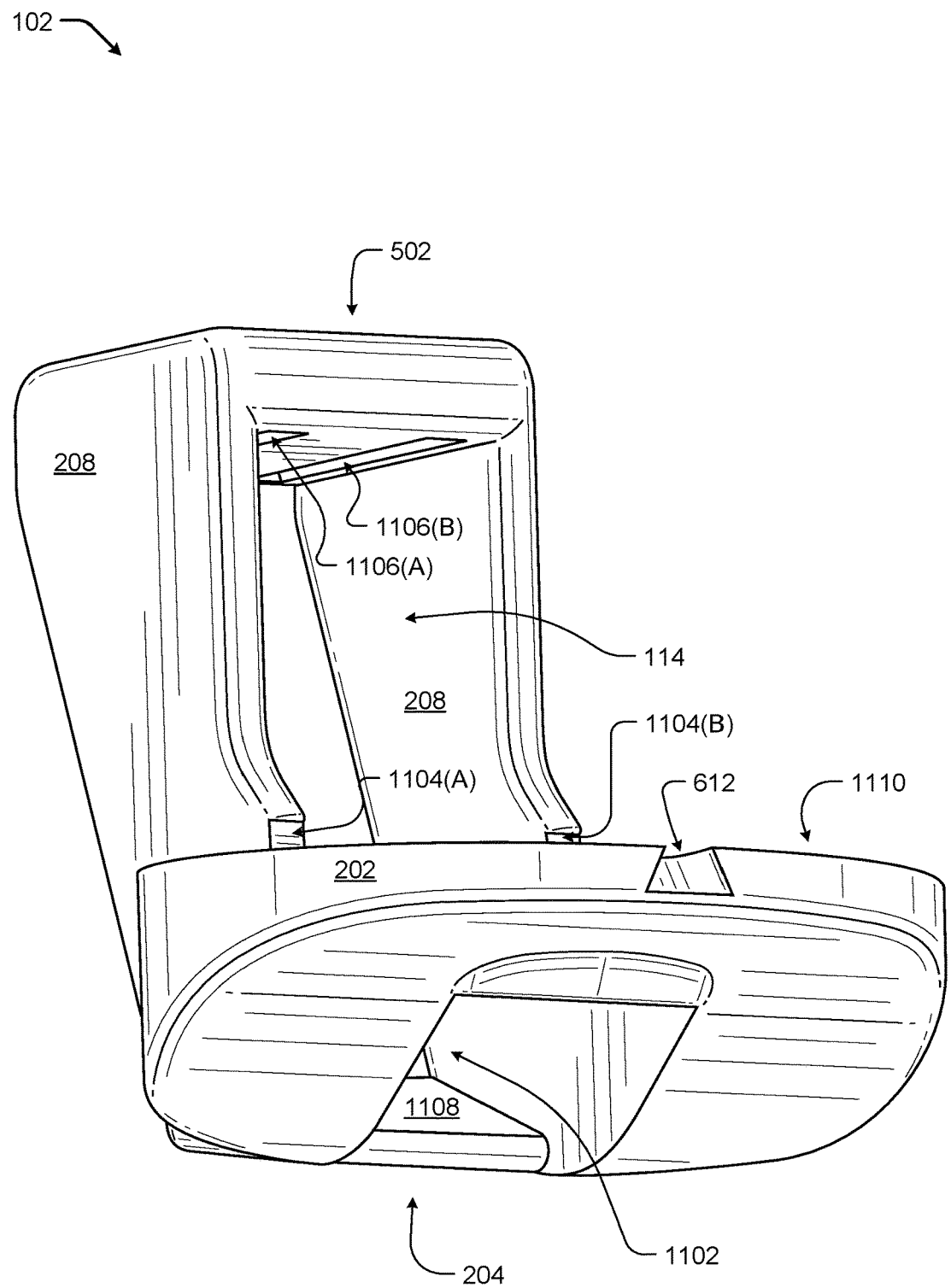
FIG. 11 depicts an example perspective view of the main body of the adjustable finger splint of FIG. 1 according to some implementations.

FIG. 11 depicts an example back perspective view of the main body 102 of the adjustable finger splint 100 of FIG. 1 according to some implementations. As discussed above, the main body 104 includes a MCP platform 202 for providing support for both the palmar pad (not shown) and a palm of the user (not shown), a frame 208 that supports both a PIP platform 502 and the slide platform 204 at opposite ends. For instance, the PIP platform 502 is position above a top surface 1110 of the MCP platform 202 and the slide platform 204 is positioned below a bottom surface of the MCP platform 202.

The frame 208 may form a continuous opening between the PIP platform 502 and the slide platform 204 from the front of the main body 102. However, the continuous opening may be divided into two segments from the back of the main body 102 by the MCP platform 202. The two segments of the continuous opening include the finger opening 114 for receiving the finger and a slide opening 1102 for receiving the slide 104 of FIGS. 1-10. Thus, in the illustrated implementation, the slide opening 1102 may receive or be occupied the slide 104 during use.

The MCP platform 202 may include one or more receptacles, such as a receptacle 612 configured to mate or lock with the palmar pad 108 of FIGS. 1-9. The receptacle 612 may be between approximately 0.5 cm and 3.0 cm long, 0.5 cm and 1.0 cm wide, and 0.2 cm and 0.5 cm deep. The receptacle 612 may also be narrow along the top and wider along the bottom such that the side walls are angled or flanged outward from top to bottom. The flanged walls prevent the palmar pad 108 from dislodging during use as the slide 104 pushes upward on the front end of the palmar pad 108(A). The receptacle 612 is also open at the top surface such that the palmar pad 108 may include a coupling component that may mate with the receptacle 612 and is integral with the body of the palmar pad 108, as discussed in more detail below. In some cases, the flange walls may be at an angle of between approximately 50 and 70 degrees. The frame 208 may also include grooves, generally indicated by 1104(A) and 1104(B), that may mate with the front portion of the palmar pad 108. The frame 208 may have an overhang that defines the grooves 1104. The overhangs may also act to resist upward movement of the palmar pad 108 when the slide 104 is engaged. The grooves 1104 may also help resist any forward movement of the palmar pad 108.

The PIP platform 502 includes a bottom surface that also includes one or more receptacles, such as receptacles 1106 (A) and 1106(B). The receptacles 1106 may run the full length of the PIP platform 502 or may only run a partial length of the PIP platform 502. For instance, the receptacles 1104 may be between approximately 1.0 cm and 3.0 cm long, 0.5 cm and 1.5 cm wide, and 0.5 cm and 1.0 cm deep. In some cases, the length of the receptacles 1106 may be longer than the length of the coupling components of the dorsal pad 106 such that the dorsal pad 106 may be able to slide or adjust as the slide 104 is engaged with the palmar pad 108, as will be discussed in more detail below.

The slide platform 204 may include a top surface 1108 that is at an incline relative to the top surface 1108 of the MCP platform 202. In some cases, the include may be at an angle of between approximately 5.0 and 15.0 degrees. The incline of the top surface 1108 causes the slide 104 to impact the front end of the palmar pad 108(A) at an angle that gradually extends or straightens the finger through zero degrees of flexion and into the range of hyperextension.

In some examples, the main body 102 may be formed as a single component or unit. The main body 102 may be formed from a rigid material, such as various plastics, polymers, polyethylene terephthalate, among others. In some cases, the main body 102 may have a hardness rating of between approximately shore D average hardness rating of between approximately 75 and 85.

Figure 12:
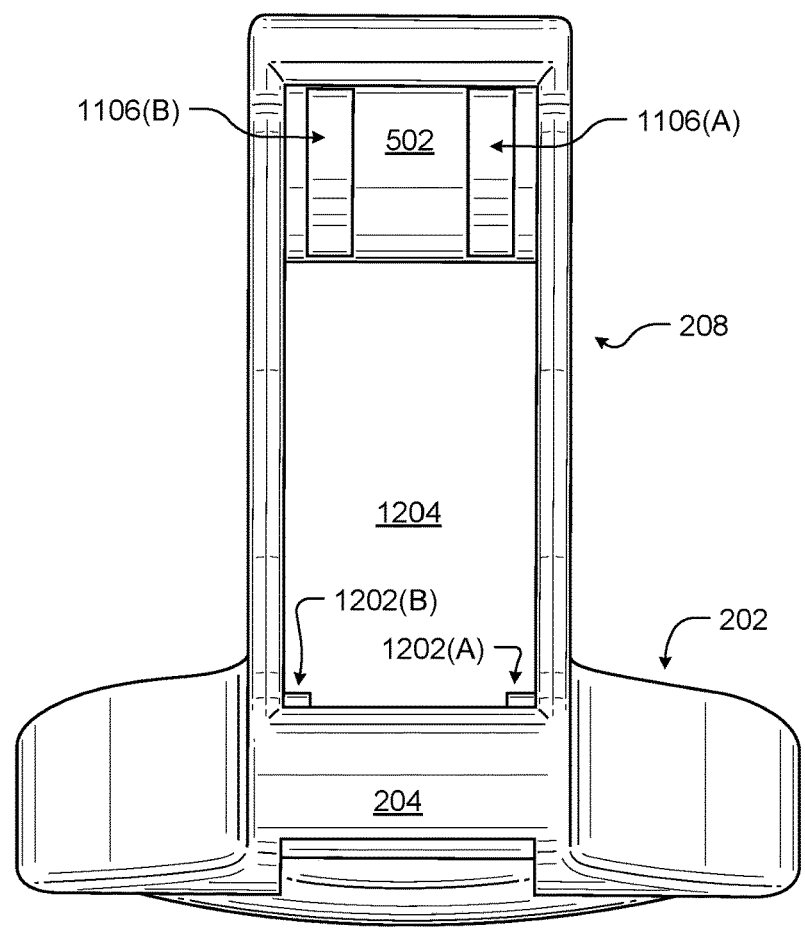
FIG. 12 depicts an example partial-front-partial-bottom view of the main body of the adjustable finger splint of FIG. 1 according to some implementations.

FIG. 12 depicts an example partial-front-partial-bottom view of the main body 102 of the adjustable finger splint 100 of FIG. 1 according to some implementations. In the illustrated example, the receptacles 1106(A) and 1106(B) for receiving the coupling components of the dorsal pad 106 (not shown) are visible along the bottom surface of the PIP platform 502. The frame 208 may also support slide locking members, generally indicated by 1202(A) and 1202(B), within the space of the continues opening 1204. As discussed above, the opening 1204 is continuous along the lengths of the main body 102 from the front but divided between the finger opening 114 and the slide opening 1102 from the back by the MCP platform 202. Thus, from the current partial-front view of the main body 102, the opening 1204 runs the full length between the PIP platform 502 and the slide platform 204 as shown.

Figure 13:
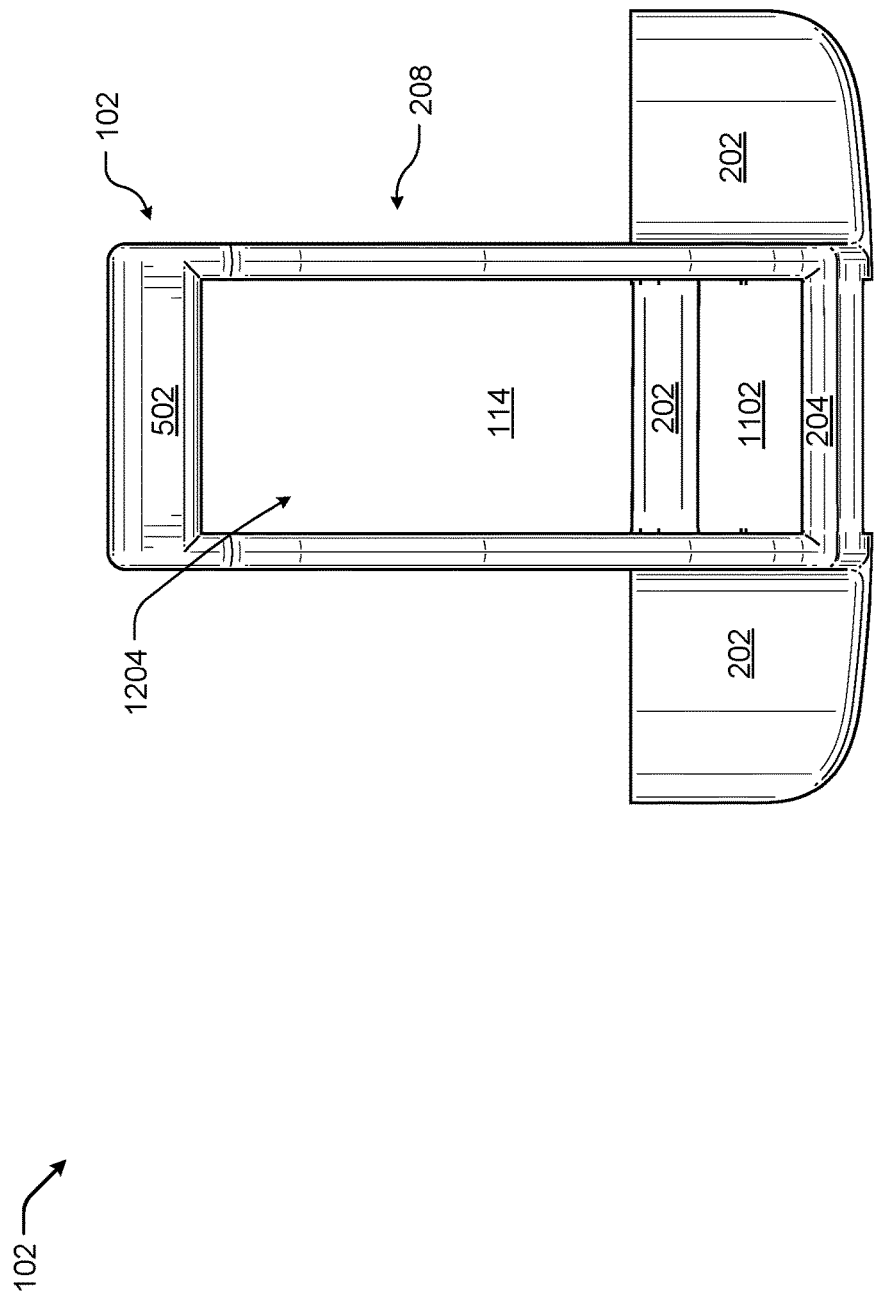
FIG. 13 depicts an example back view of the main body of the adjustable finger splint of FIG. 1 according to some implementations.

FIG. 13 depicts an example back view of the main body 102 of the adjustable finger splint 100 of FIG. 1 according to some implementations. In the current illustration, the continuous opening 1204 is defined by the frame 208, the slide platform 204, and the PIP platform 502 and is divided into two segments, finger opening 114 and the slide opening 1102 by the MCP platform 202. In the current implementation, the continuous opening 1204 may be between approximately 5.0 cm and 6.0 cm tall and 2.0 cm and 3.0 cm wide. Similarly, the finger opening 114 may be between approximately 3.5 cm and 4.5 cm tall and 2.0 cm and 3.0 cm wide and the slide opening 1102 may be between approximately 0.5 cm and 1.5 cm tall and 2.0 cm and 3.0 cm wide. In one particular example, continuous opening 1204 may be approximately 5.2 cm tall and 2.2 cm wide, the finger opening 114 may be approximately 3.8 cm tall and 2.2.2 cm wide, and the slide opening 1102 may be approximately 0.8 cm tall and 2.2 cm wide.

In some cases, the frame 208 may be between approximately 6.5 cm and 7.5 cm long or tall and vary between approximately 3.1 cm and 1.5 cm wide. The PIP platform 502 may be between approximately 2.5 cm and 3.5 cm wide and 2.5 cm and 3.5 cm deep. The PIP platform 502 may also have a thickness of between approximately 0.5 cm and 1.0 cm. Similarly, the slide platform 204 may be between approximately 2.5 cm and 3.5 cm wide and 1.0 cm and 2.0 cm deep. The slide platform 204 may also have a thickness of between approximately 0.1 cm and 0.5 cm.

Figure 14:
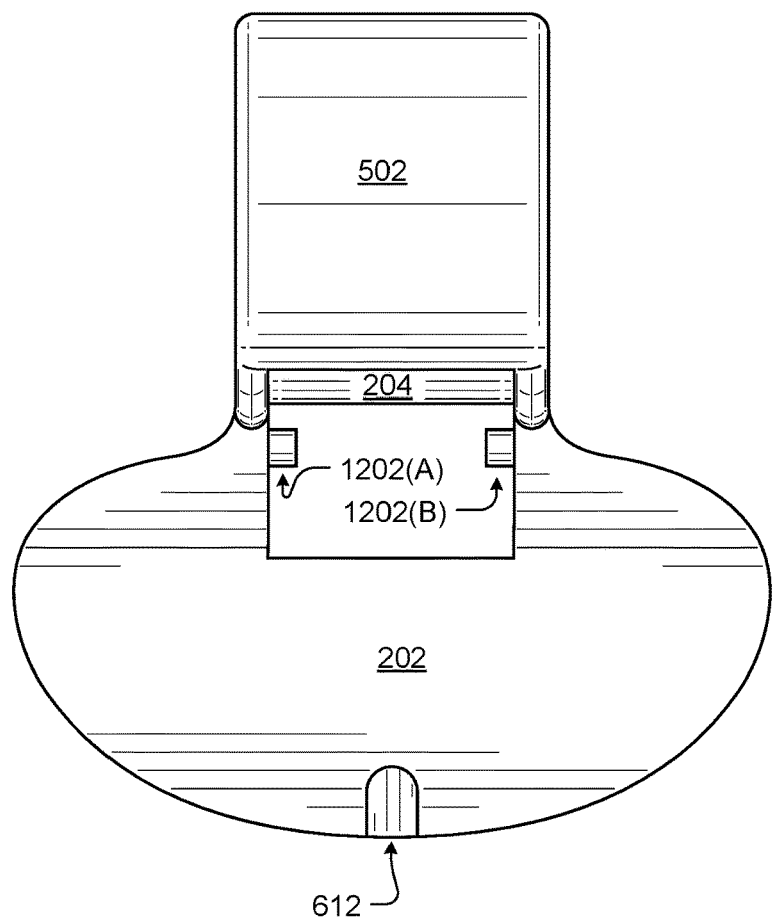
FIG. 14 depicts an example top view of the main body of the adjustable finger splint of FIG. 1 according to some implementations.

FIG. 14 depicts an example top view of the main body 102 of the adjustable finger splint 100 of FIG. 1 according to some implementations. In the current illustration, the PIP platform 502 and the MCP platform 202 are visible. As the slide platform 204 extends past the back edge of the PIP platform 502, a portion of the slide platform 204 is also visible. In the current example, the slide locking members 1202 are also visible. The slide locking members 1202 may be configured to lock or mate with the recessed portion 1012 of the slide 104 (not shown) via the opening 1014 in the bottom portion of the wedge 404. For instance, the slide 104 may be first placed through the slide opening 1102 from the back of the main body 102. The wedge 404 of the slide 104 may then be positioned above the slide locking members 1202 to align the opening 1014 with the slide locking members 1202. Next, the slide 104 may be lowered such the slide locking members 1202 are received by the recessed portion 1012 of the slide 104. The slide 104 may then adjust with respect to the main body 102 as the slide locking members 1202 move within the recessed portion 1012 relative to the main body 102. In some cases, the palmar pad 108 (not shown) is then placed over the MCP platform 202 by mating the coupling component of the palmar pad 108 with the receptacle 612. When in place the palmar pad 108 blocks or prevents the slide 104 from decoupling from the slide locking members 1202 and, thus, from decoupling from the main body 102.

From the illustrated example, it should be understood that the width of the MCP platform 202 is wider than the width of the PIP platform 502. In some cases, the width of the MCP platform 202 may be between approximately 6.0 cm and 7.0 cm and the length of the MCP platform 202 may be between approximately 3.0 cm and 4.0 cm. The MCP platform 202 may also have a thickness that varies from back to front. For example, the thickness at the back of the MCP platform 202 may be between approximately 1.8 cm and 2.2 cm and the thickness at the front of the MCP platform 202 may be between approximately 0.2 cm and 0.7 cm.

Figure 15:
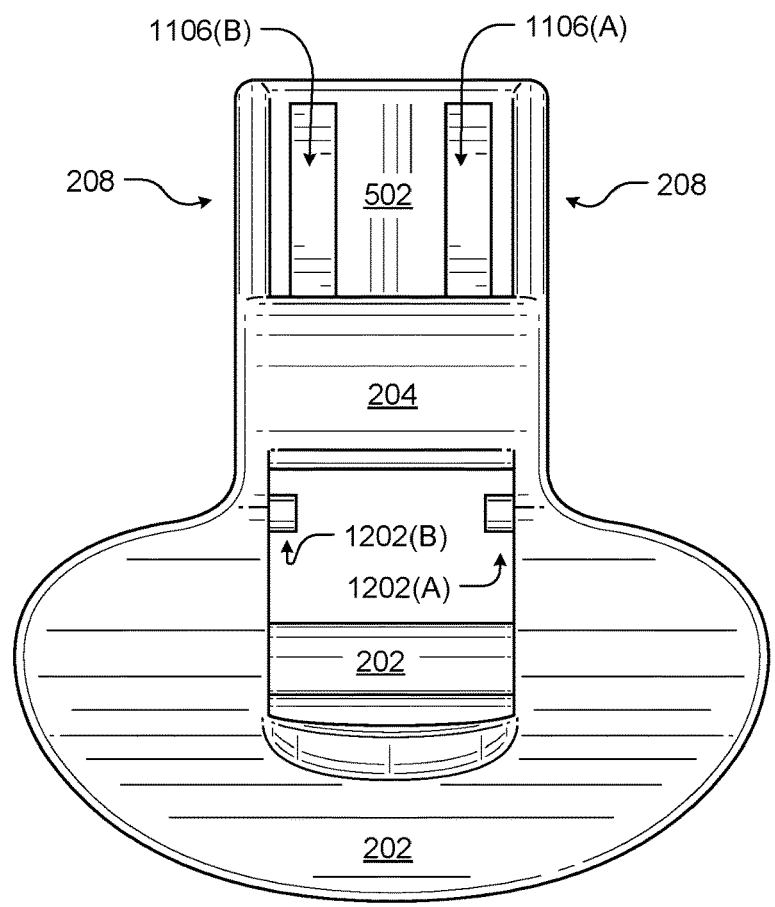
FIG. 15 depicts an example bottom view of the main body of the adjustable finger splint of FIG. 1 according to some implementations.

FIG. 15 depicts an example bottom view of the main body 102 of the adjustable finger splint 100 of FIG. 1 according to some implementations. In the current illustration, the slide platform 204 and the MCP platform 202 are visible. As the PIP platform 502 extends past the front edge of the slide platform 204, a portion of the PIP platform 502 is also visible. In the current example, the slide locking members 1202 are also visible. As discussed above, the slide locking members 1202 may be configured to lock or mate with the recessed portion 1012 of the slide 104 (not shown) via the opening 1014 in the bottom portion of the wedge 404. The receptacles 1106(A) and 1106(B) for receiving the coupling components of the dorsal pad 106 (not shown) are also visible. In some cases, the receptacles 1106 may be approximately 0.2 cm from the edge front edge of the main body 102, approximately 0.2 cm from the back edge of the main body 102, and approximately 0.2 cm from either side wall of the frame 208 of the main body 102.

Figure 16:
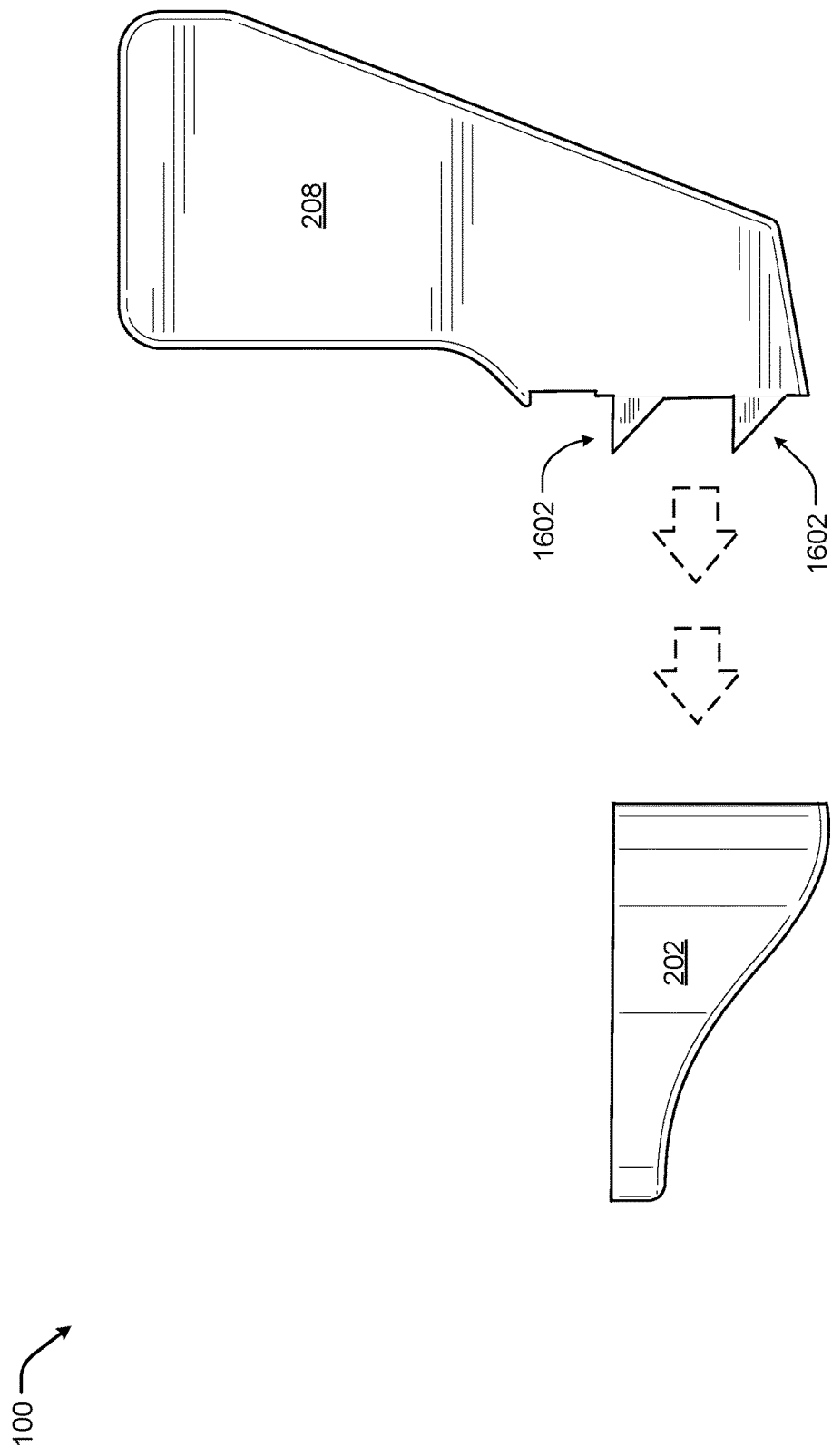
FIG. 16 depicts an example side view of a two-part main body of the adjustable finger splint of FIG. 1 according to some implementations.

FIG. 16 depicts an example side view of a two-part main body 102 of the adjustable finger splint 100 of FIG. 1 according to some implementations. In the above examples, the MCP platform 202 and the frame 208 may be integrally coupled or formed as a single component. However, in some cases, the MCP platform 202 may be formed as a separate component from the frame 208 and configured to releasably couple to the frame 208. For example, the palm of a specific user may be usually small or large and require a different sized MCP platform 202 for support. Alternatively, the user's finger may be too large to fit through the opening in the frame 208 while the MCP platform 202 is attached. In these examples, the MCP platform 202 may be selected to fit the individual user and then coupled to the frame 208. In the current example, the frame 208 may include male connector components 1602 and the MCP platform 202 includes female connector components. However, it should be understood that, in some implementations, the MCP platform 202 may include the male connectors and the frame 208 may include the female connectors.

Figure 17:
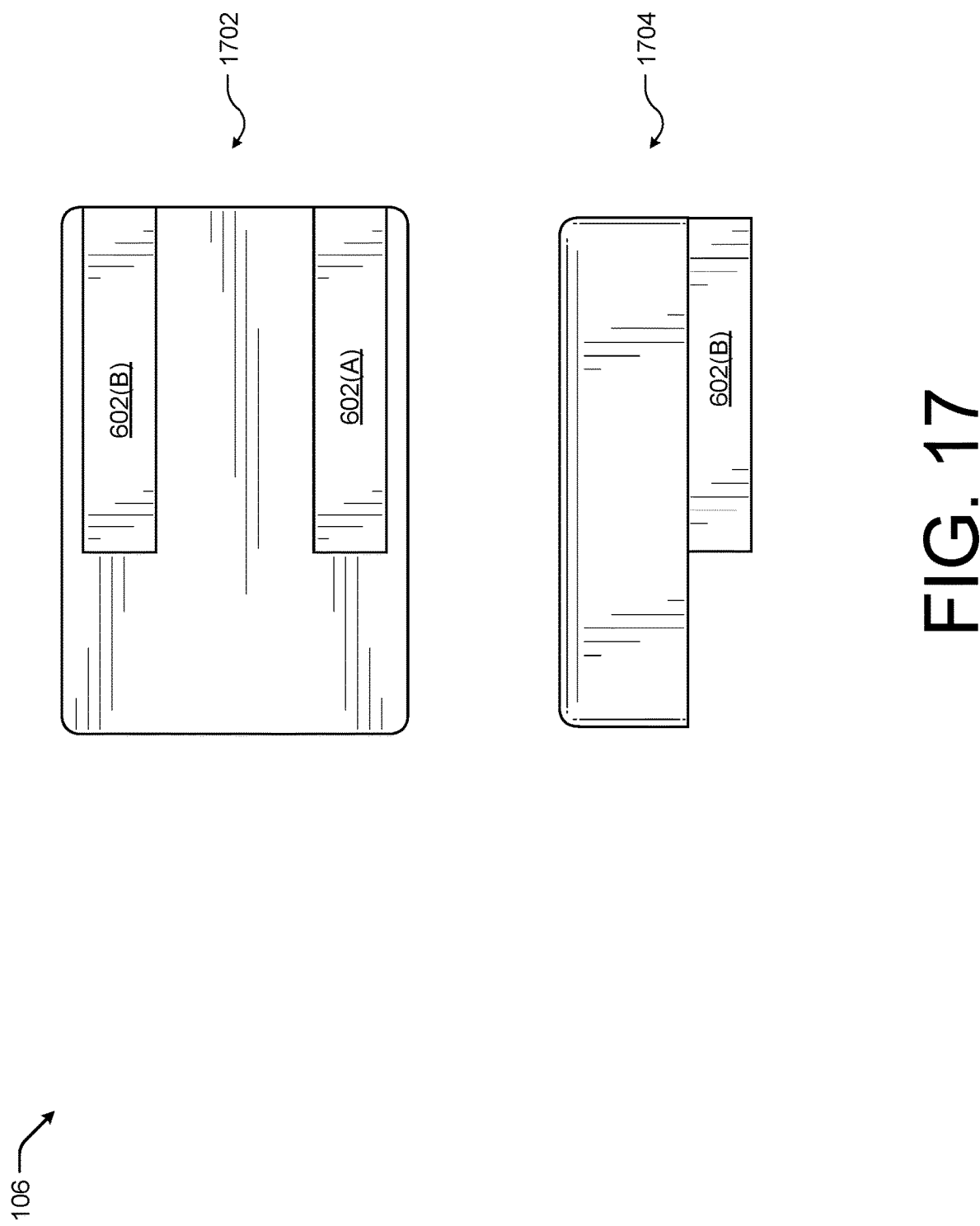
FIG. 17 depicts an example bottom view and side view of the proximal interphalangeal pad of the adjustable finger splint of FIG. 1 according to some implementations.

FIG. 17 depicts an example bottom view 1702 and a side view 1704 of the dorsal pad 106 of the adjustable finger splint 100 of FIG. 1 according to some implementations. In the current example, the dorsal pad 106 includes two coupling components 602(A) and 602(B) for securing the dorsal pad 106 to the PIP platform 502 of the main body 102 (not shown) of the splint 100. In other implementations, the PIP platform 502 may include any number of coupling components 602, such as one or three coupling components.

The dorsal pad 106 may be between approximately 0.5 cm and 1.5 cm tall, 1.5 cm and 2.5 cm wide, and 2.5 cm and 3.5 cm deep. In one particular example, the dorsal pad 106 may be approximately 0.8 cm tall (not including the extension of the coupling components 602), 2.0 cm wide, and 2.5 cm and 3.1 cm deep. In some cases, the coupling components 602 may be less than the full depth of the dorsal pad 106 as illustrated. In these cases, the coupling components 602 may be between approximately 0.2 cm and 0.7 cm tall, 0.2 cm and 0.4 cm wide, and 1.5 cm and 2.5 cm deep. The coupling components 602 may also be shorter than the receptacles 610 of the PIP platform 502 on the main body 102 (not shown), such that the dorsal pad 106 may slide or move relative to the main body 102 and, thereby, adjust for comfort of the user. In some cases, the dorsal pad 106 may be formed from a material, such as various plastics, polyurethanes, rubbers, foams, or other material. In some cases, the dorsal pad 106 may have having a shore A hardness of between approximately 80 A and 90 A.

Figure 18:
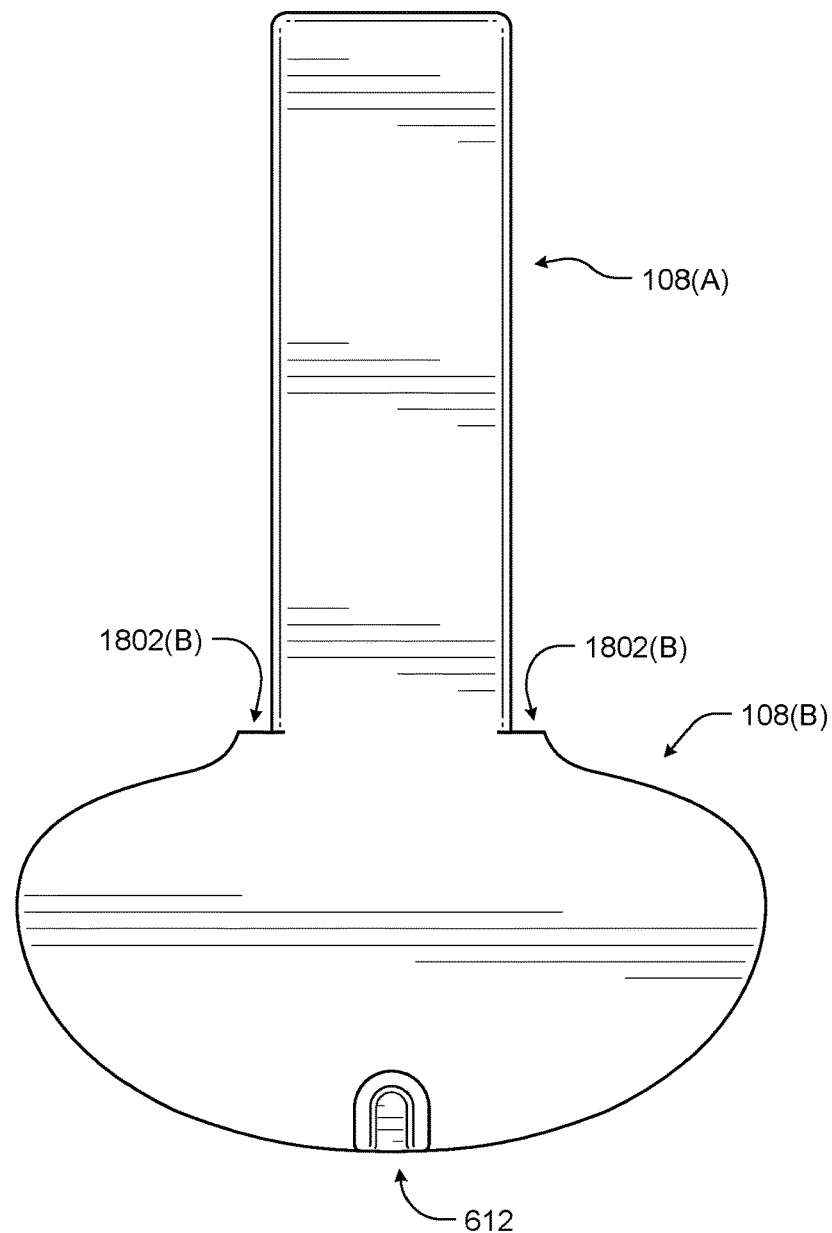
FIG. 18 depicts an example bottom view of the palmar pad of the adjustable finger splint of FIG. 1 according to some implementations.

FIG. 18 depicts an example bottom view of the palmar pad 108 of the adjustable finger splint 100 of FIG. 1 according to some implementations. As discussed above, the palmar pad 108 includes a front portion 108(A) and a back portion 108(B). The front portion 108(A) may be configured to flex when impacted by the slide 104 (not shown). In various implementing, the back portion 108(A) may be wider than the front portion 108(A) and configured to support the palm of the user. For example, the back portion 108(B) may be between approximately 3.0 cm and 4.0 deep and 6.0 cm and 7.0 cm wide and the front portion 108(A) may be between approximately 6.0 cm and 7.0 cm deep and 1.5 cm and 2.5 cm wide. Thus, the palmar pad 108 may be between approximately 9.5 cm and 10.5 cm deep. In another example, the palmar pad 108 may be between approximately 8.0 cm and 15 cm deep.

In the current example, the front portion 108(A) and the back portion 108(B) of the palmar pad 108 may be formed form the same material. However, in other examples, the front portion 108(A) and the back portion 108(B) of the palmar pad 108 may be formed from different materials. For instance, the material of the front portion 108(A) may be less rigid than the material of the back portion 108(B). In some cases, the palmar pad 108 may be formed from a material, such as various plastics, elastomers, polyurethanes, rubbers, foams, or other material. In some cases, the palmar pad 108 may have having a shore A hardness of between approximately 80 A and 98 A.

In the illustrated example, the palmar pad 108 also includes coupling component 606 for securing the palmar pad 108 to the main body 102 of the splint 100. In the current example, the coupling component 606 may be between approximately 0.2 cm and 0.5 cm tall, 0.5 cm and 1.0 cm wide, and 0.8 cm and 2.5 cm deep.

In some implementations, the main body 102 may also include grooves 1104 along the frame 208. In these examples, the palmar pad 108 may include a mating surfaces 1802(A) and 1802(B) to contact or be received within the grooves 1104. The contact between the mating surfaces 1802 and the grooves 1104 together with the coupling component 606 may prevent forward motion of the palmar pad 108 with respect to the main body 102 of the splint 100 during use.

Figure 19:
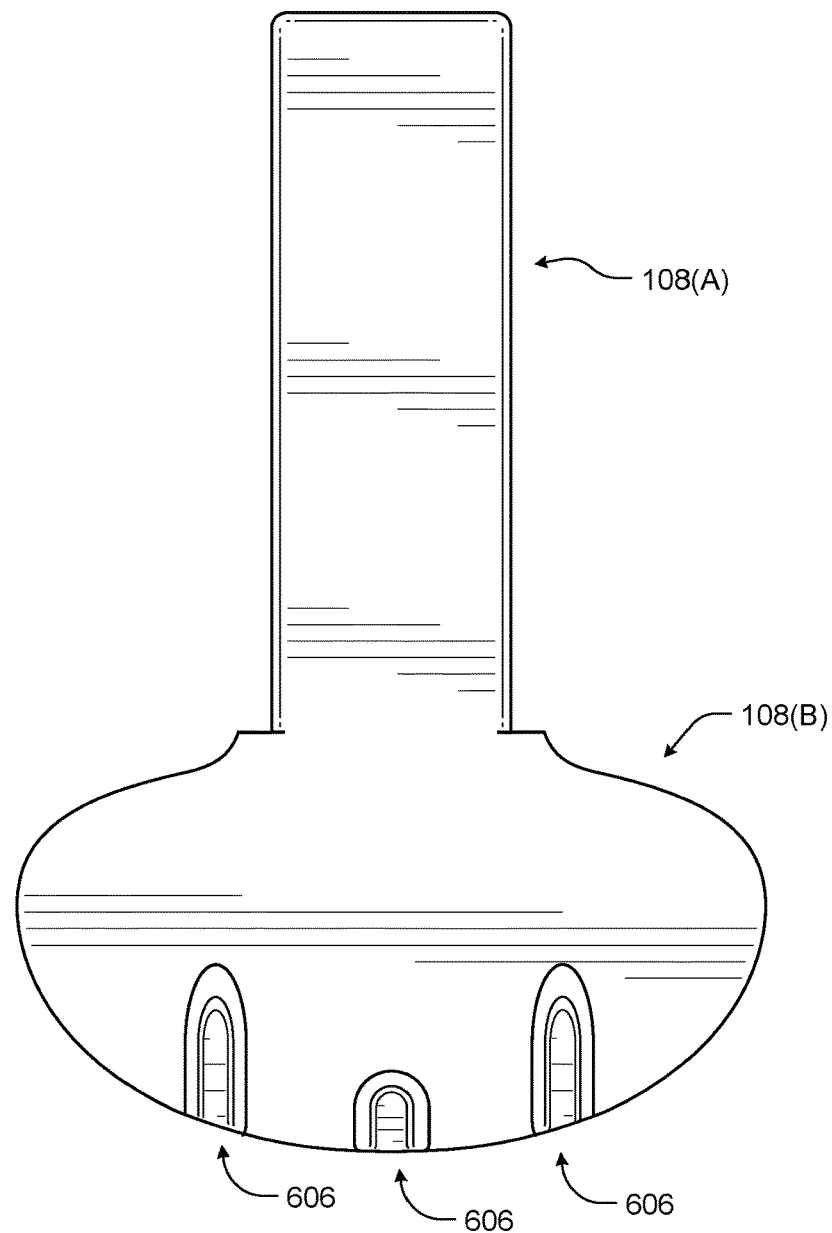
FIG. 19 depicts another example bottom view of the palmar pad of the adjustable finger splint of FIG. 1 according to some implementations.

FIG. 19 depicts another example bottom view of the palmar pad 108 of the adjustable finger splint 100 of FIG. 1 according to some implementations. Similar, to the implementation illustrated in FIG. 18, the current palmar pad 108 includes a front portion 108(A) and a wider back portion 108(B). In the current example, the palmar pad 108 also includes multiple coupling components 612. As illustrated, it should be understood that the length and/or width of each of the individual coupling components 606 may vary with respect to each other or across implementations.

Figure 20:
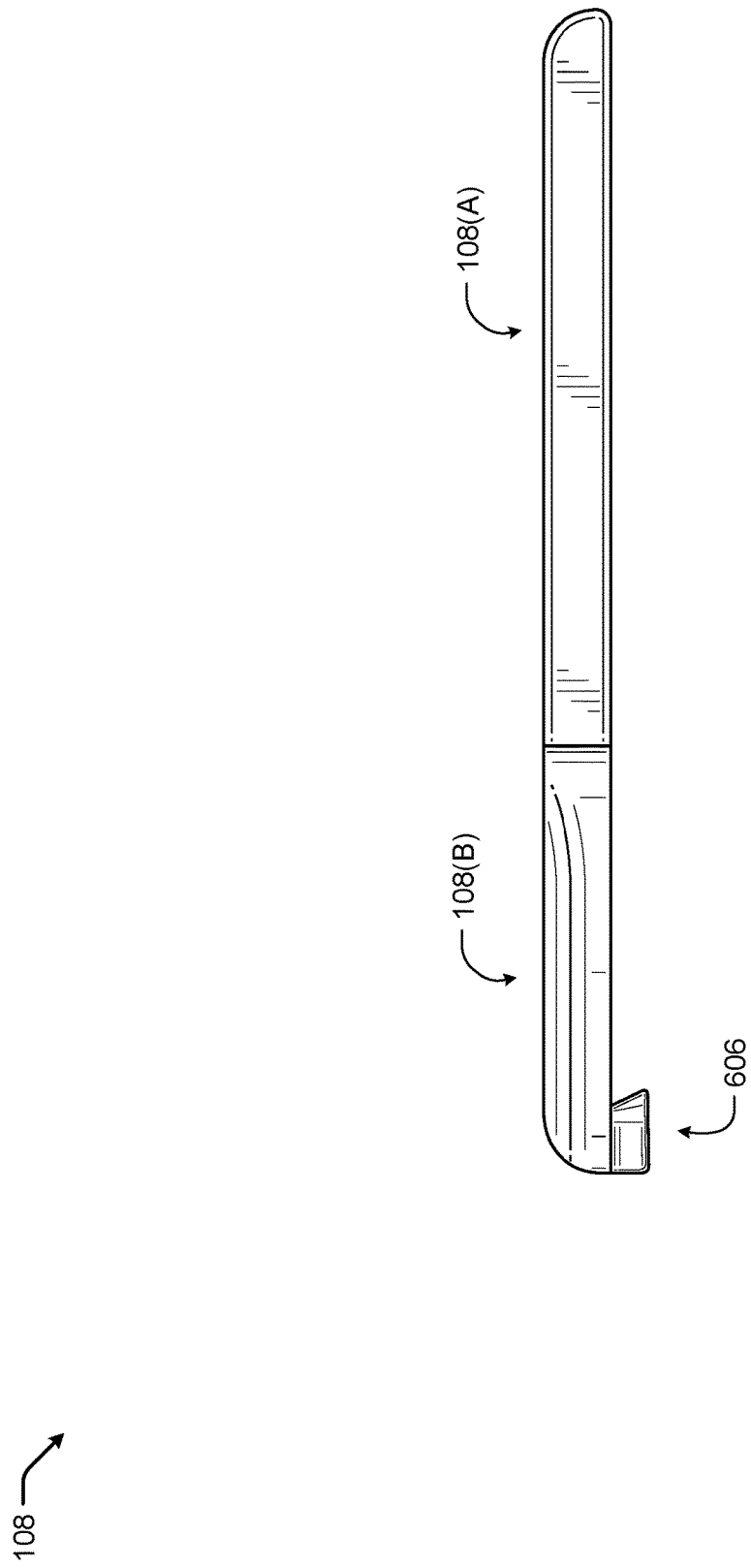
FIG. 20 depicts an example side view of the palmar pad of the adjustable finger splint of FIG. 1 according to some implementations.

FIG. 20 depicts an example side view of the palmar pad 108 of the adjustable finger splint 100 of FIG. 1 according to some implementations. In the current example, both portions (e.g., the front portion 108(A) and the back portion 108(B)) of the palmar pad 108 may be formed from a single material. In this example, the palmar pad 108 may have a thickness that may be between approximately 0.5 cm and 1.0 cm. In other examples, the thickness of the front portion 108(A) may vary or differ from the thickness of the back portion 108(B). For instance, the front portion 108(A) may be thicker than the back portion 108(B) as the injured finger may require more padding than the palm of the user. As discussed above, the palmar pad 108 may also include one or more coupling components, such as coupling component 606.

Figure 21:
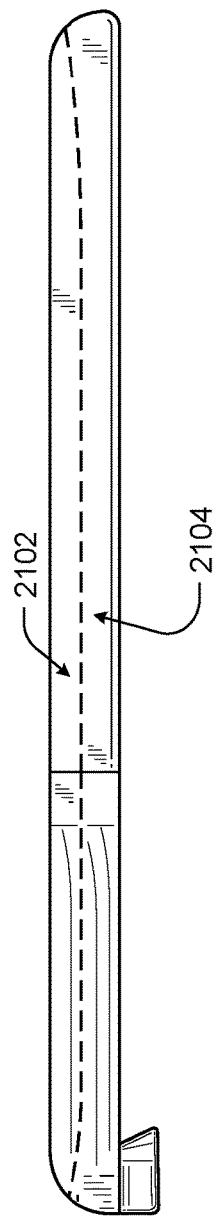
FIG. 21 depicts another example side view of the palmar pad of the adjustable finger splint of FIG. 1 according to some implementations.

FIG. 21 depicts another example side view of the palmar pad 108 of the adjustable finger splint 100 of FIG. 1 according to some implementations. In this example, the palmar pad 108 may be formed two layers, a top layer 2102 and a bottom layer 2104. For instance, the palmar pad 108 may require some rigidity or hardness to prevent the slide 104 (not shown) from puncturing or damaging the palmar pad 108 when the palmar pad 108 is impacted by the wedge 404 of the slide 104. At the same time, the palmar pad 108 may be configured to provide a desired level of flexibility to reduce pain on the finger when the splint 100 is in use. Thus, in the current example, the top layer 2102 may be formed from a first material and the bottom layer 2104 may be formed from a second material. In some cases, the second material may be harder than the first material. For example, the first material may be a plastic, polyurethanes, elastomers, or other material having a Shore A hardness between approximately 80 A and 90 A and the second material may also be a plastic, polyurethanes, elastomers, or other material having a hardness between approximately 90 A and 100 A.

Figure 22:
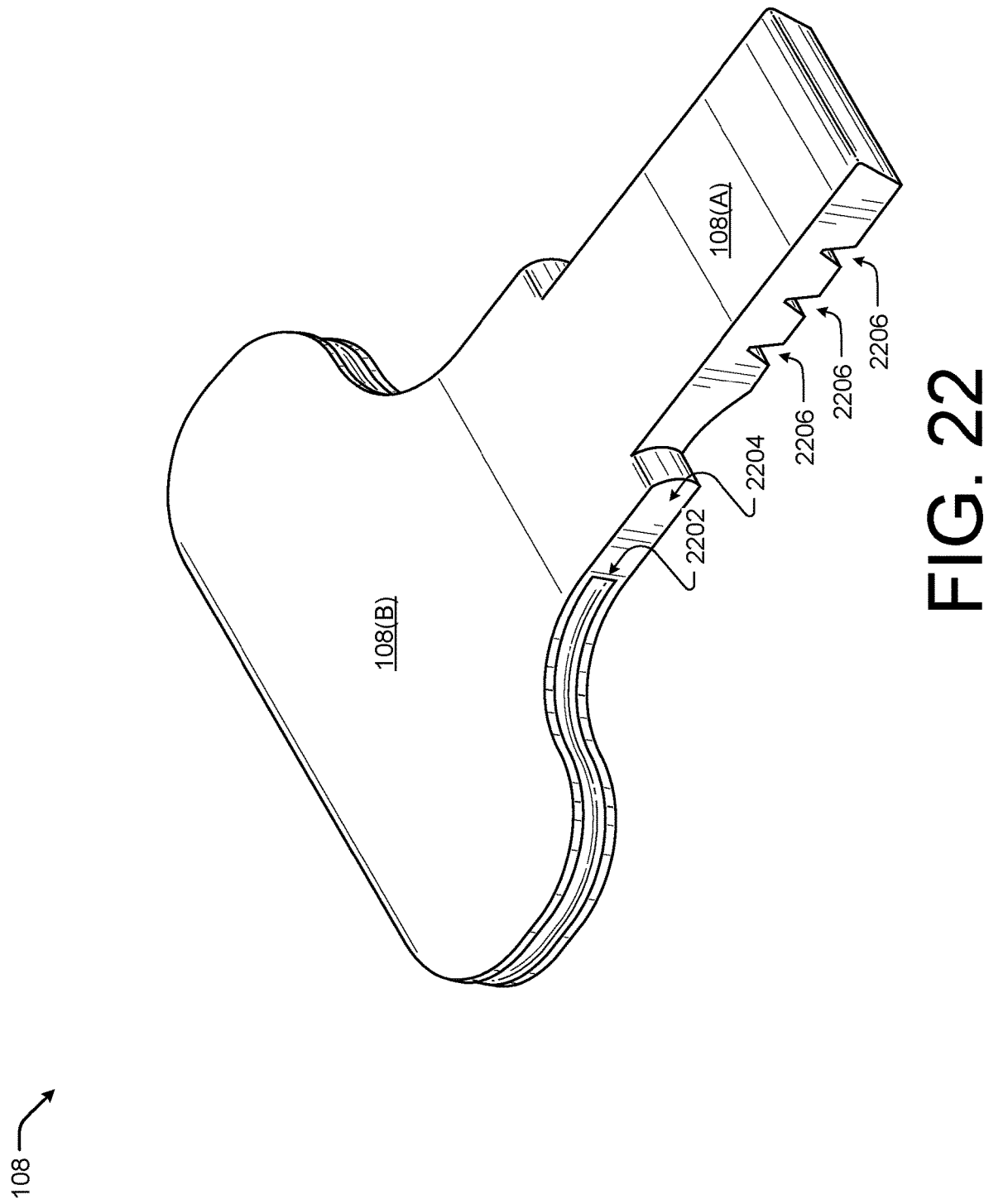
FIG. 22 depicts another example perspective view of the palmar pad of the adjustable finger splint of FIG. 1 according to some implementations.

FIG. 22 depicts another example perspective view of the palmar pad 108 of the adjustable finger splint 100 of FIG. 1 according to some implementations. As discussed above, the palmar pad 108 may be formed from two materials, a more flexible material and a more rigid material. In this example, the rigid material may be formed an interior layer 2202 that provides support for the back end of the palmar pad 108(B) to provide support for the palm of the user and some rigidity to the overall pad 108. The current example, also includes an exterior layer 2204 that runs along the top and bottom of the interior layer 2202 within the back end of the palmar pad 108(A) and forms the entirety of the front end of the palmar pad 108(A). In this example, the interior layer may be formed from the first material and the exterior layer may be formed from the second material.

In the illustrated example, the front end of the palmar pad 108(A) or the finger portion of the palmar pad 108 may include notches, generally indicated by 2206, along the bottom surface of the pad 108. The notches 2206 may be used to secure the palmar pad 108 to the slide 104 and to assist in maintain the palmar pad 108 in contact and in a desired alignment with the slide 104. In the current example, the palmar pad 108 includes three notches 2206, however, it should be understood that any number of notches 2206 may be implemented. In some cases, the notches 2206 may also add thickness to the palmar pad 108 and increase comfort while maintaining desired flexibility.

Figure 23:
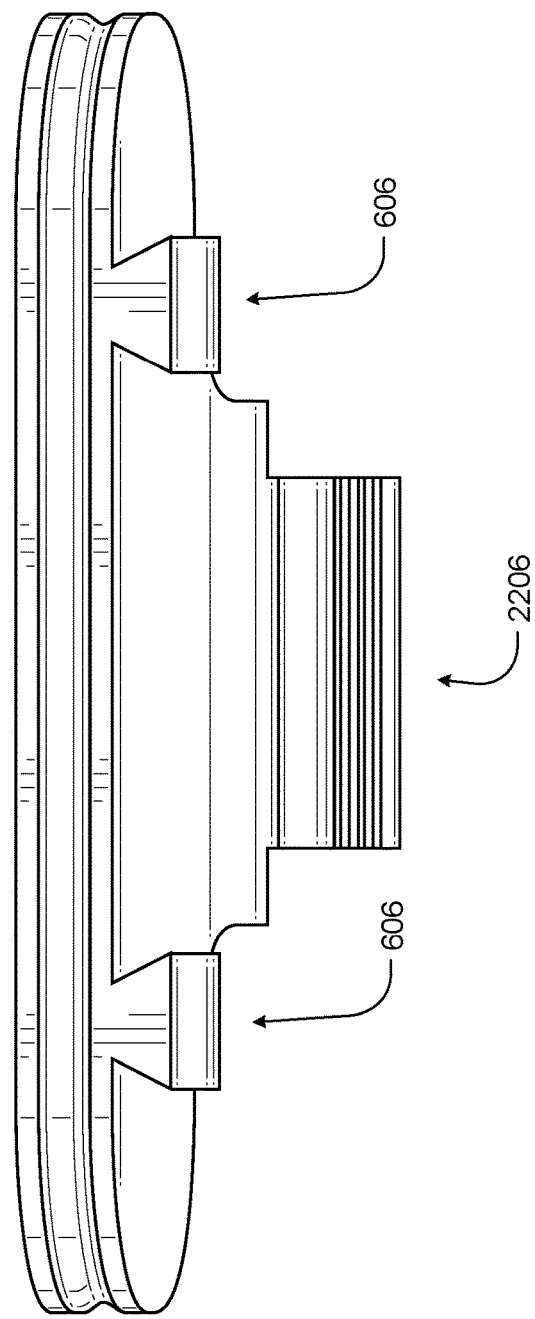
FIG. 23 depicts another example back view of the palmar pad of the adjustable finger splint of FIG. 1 according to some implementations.

FIG. 23 depicts another example back view of the palmar pad 108 of the adjustable finger splint 100 of FIG. 1 according to some implementations. In the current example, the palmar pad 108 includes two coupling components 606 and multiple notches 2206 for coupling the palmar pad 108 to both the main body 102 and the slide 104 (not shown), as discussed above.

Figure 24:
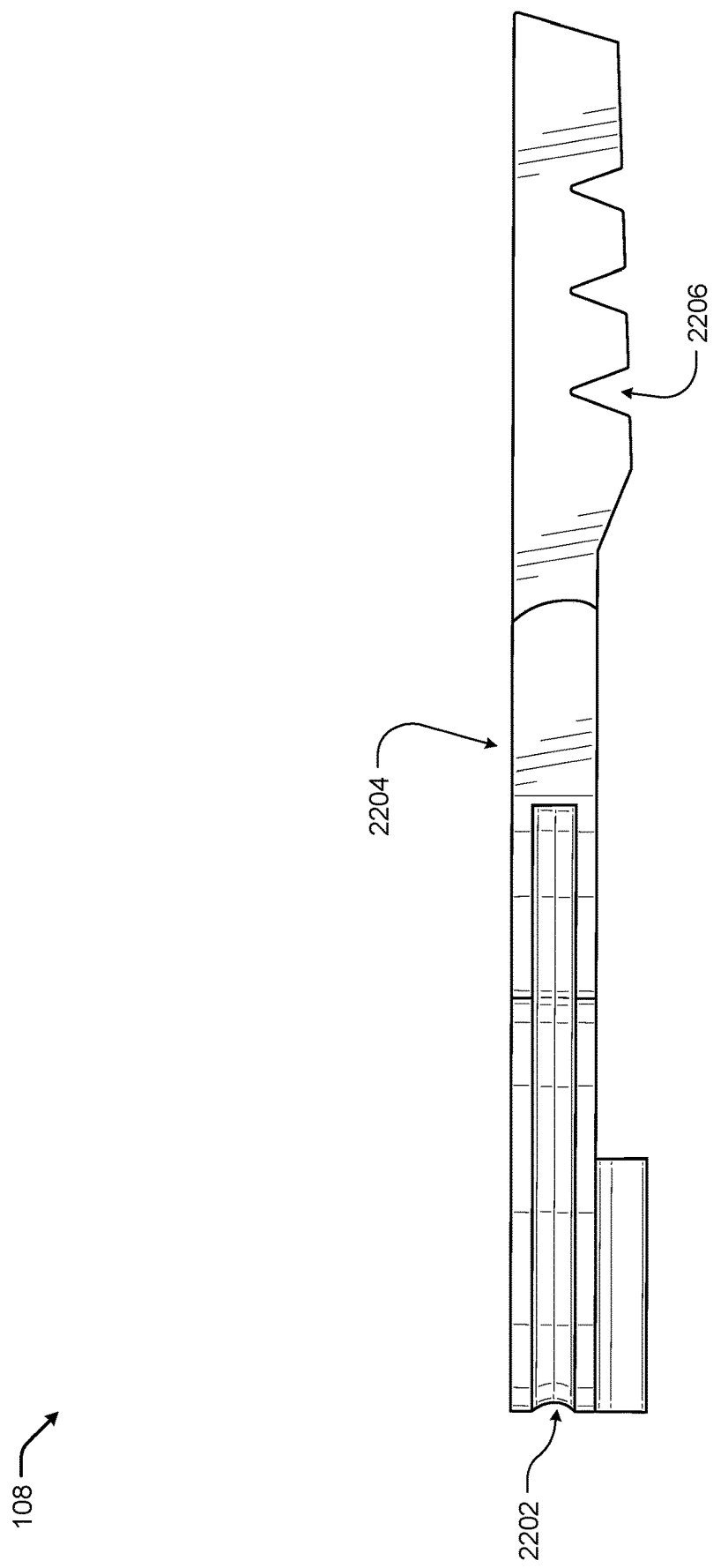
FIG. 24 depicts another example side view of the palmar pad of the adjustable finger splint of FIG. 1 according to some implementations.

FIG. 24 depicts another example side view of the palmar pad 108 of the adjustable finger splint 100 of FIG. 1 according to some implementations. In the current example, again the palmar pad 108 includes an interior layer 2202 and an exterior layer 2204. The notches 2206 are also shown for coupling the palmar pad 108 to the slide 104 (not shown).

Figure 25:
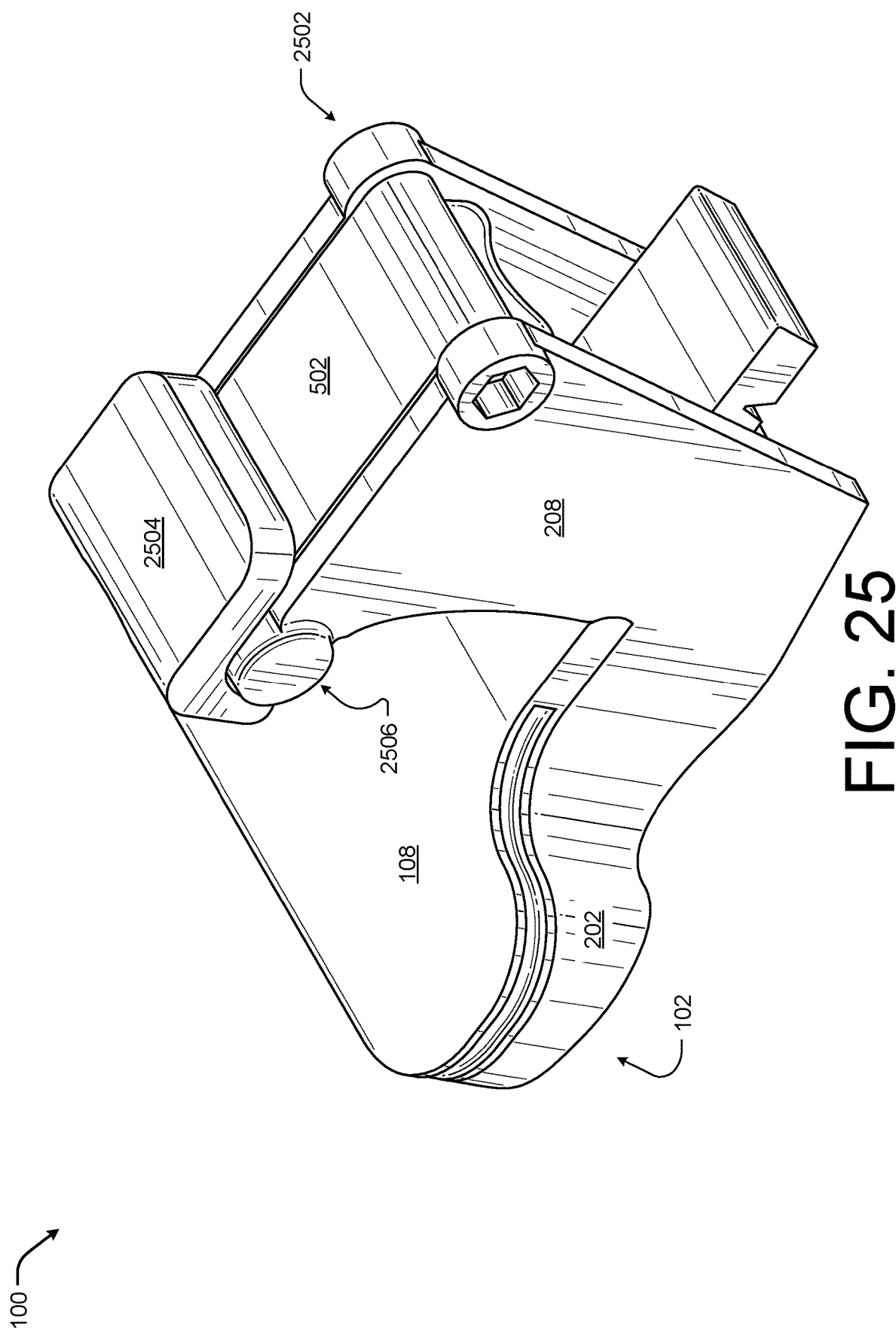
FIG. 25 depicts an example perspective view of a main body of the adjustable finger splint of FIG. 1 with an adjustable proximal interphalangeal platform in a closed position according to some implementations.

FIG. 25 depicts an example perspective view of a main body 102 of the adjustable finger splint 100 of FIG. 1 with an adjustable PIP platform 502 in a closed position according to some implementations. In some cases, the user's finger may be severely injured or bent. In these cases, the user may be unable to push the finger through the finger opening 114 if the PIP platform 502 is affixed to the frame 208. Thus, in the illustrated example, the PIP platform 502 may be movable between a closed position and an open position.

In the illustrated example, the PIP platform 502 may be coupled to the frame 208 via hinges, generally indicated by 2502, such that the PIP platform 502 may open upward from the frame 208. The PIP platform 502 may also be locked or held in place via locking platform 2504. The locking platform 2504 may also be coupled to the frame 208 via mating component 2506. The PIP platform 502 may then be released from the closed position by disengaging the locking platform 2504, as will be discussed in more detail below with respect to FIG. 26.

Figure 26:
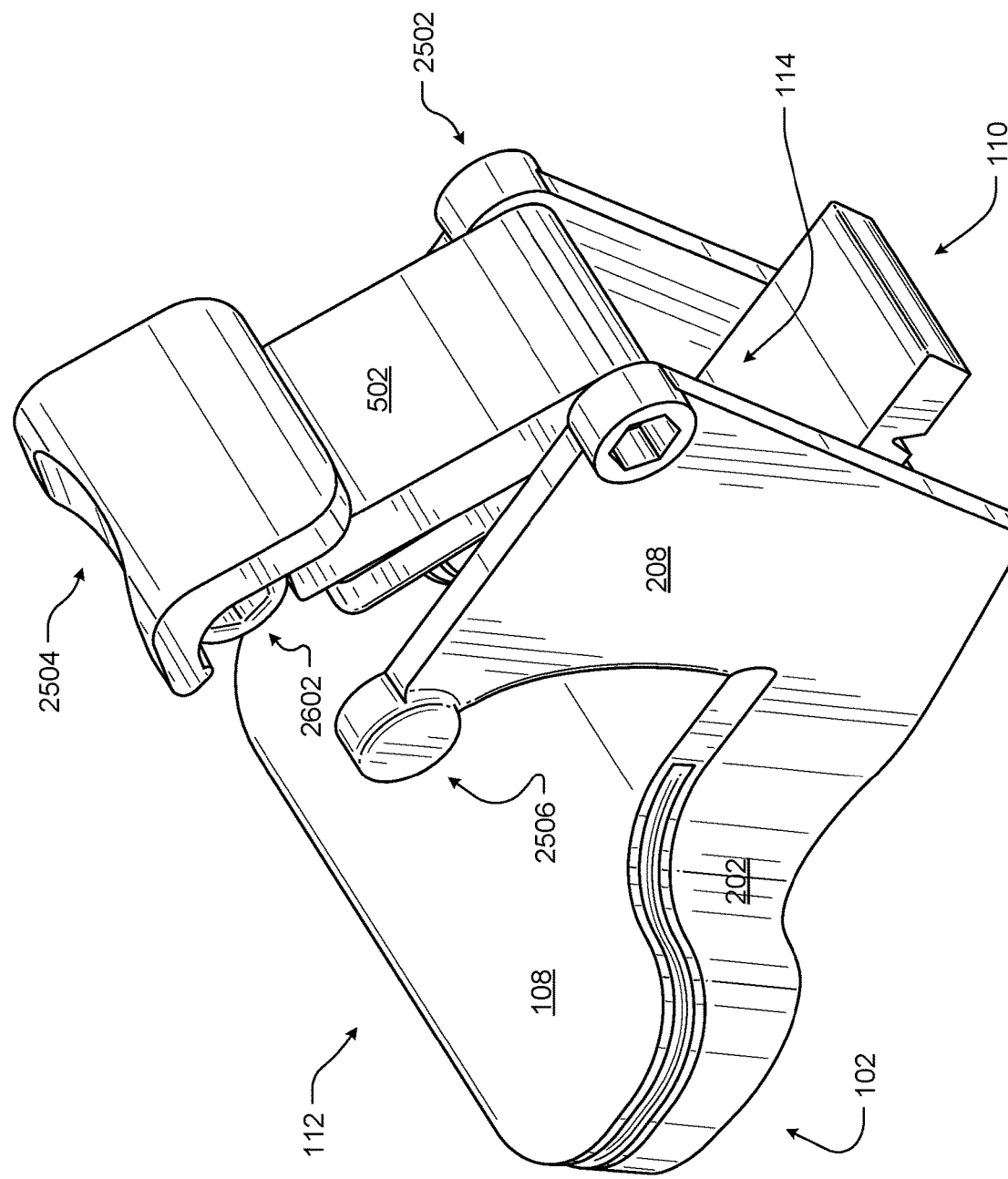
FIG. 26 depicts an example perspective view of a main body of the adjustable finger splint of FIG. 5 with the adjustable proximal interphalangeal platform in an open position according to some implementations.

FIG. 26 depicts an example perspective view of a main body 102 of the adjustable finger splint 100 of FIG. 25 with the adjustable PIP platform 502 in an open position according to some implementations. In the current example, the locking platform 2504 has been pushed up and towards the front end 110 of the splint 100, such that the locking platform 2504 no longer obstructs the opening 114. For instance, when in the closed position, a locking member 2602 of may extend outward and under the locking platform 2504 and releasably couple with the mating component 2206. For instance, when the locking platform 2504 is moved downward and towards the front end 110 of the splint 100, the locking platform 2504 prevents the PIP platform 502 from moving during use. In one specific example, a bolt couples 502 to 208 creating a hinged door so the platform 502 and dorsal pad (not shown) can be rotated up and away from the finger. A shorter bolt may also couple 2204 to 2502 creating a latch. After the finger is placed in the device, the door is closed and the latch may be rotated to couple to the mating component 2506.

In the current example, the PIP platform 502 is shown as a hinged component, however, it should be understood that in other examples, the PIP platform 502 may be configured to slide along a groove in the frame 208 between and the open and closed positions. It should also be understood that various other types of locking platforms, mechanisms, or members may be used. In one specific example, the PIP platform 502 may be completely removable form the frame 208.

FIG. 27 depicts an example perspective view of an adjustable finger splint 100 usable by a third-party according to some implementations. In some cases, injury to one or more fingers may be caused by age or be one of numerous injuries stained by the user. In these cases, the user may be unable to apply necessary force to the slide 104 to cause the injured finger to extend. Thus, in some implementations, the adjustable finger splint 100 may be designed, such that a third-party (e.g., physical therapist, hand therapist, doctor, surgeon, nurse, or other medical professional) is able to adjust the slide 104 relative to the main body 102. In these implementations, the slide 104 may include a pull or handle 2702 proximate to the front end 406 of the slide 104, such that the third-party may use to adjust the slide 104 relative to the main body 102 by pulling on the handle 2702. The main body 102 may also include a grip or other stabilizing portion 2704 that the third-party may utilize to substantially maintain the position of the main body 102 when adjusting the position of the slide 104. In one particular implementation, the main body 102 may be weighted such that when the adjustable finger splint 100 is set or rests on a table or other surface, the main body preserves its position as the palm side is moved.

FIG. 28 depicts an example side view of the adjustable finger splint 100 of FIG. 27 according to some implementations. As illustrated, the handle 2702 of the slide 104 may extend to both the right and left of the wedge 404. Thus, a third-party that is either right or left handed may utilize the handle 2702. In some cases, the handle 2702 may decoupled from the slide 104, such that the slide 104 may be placed through the frame 208 from the back of the splint 100 and then the handle 2702 may be attached from the front.

Figure 29B:
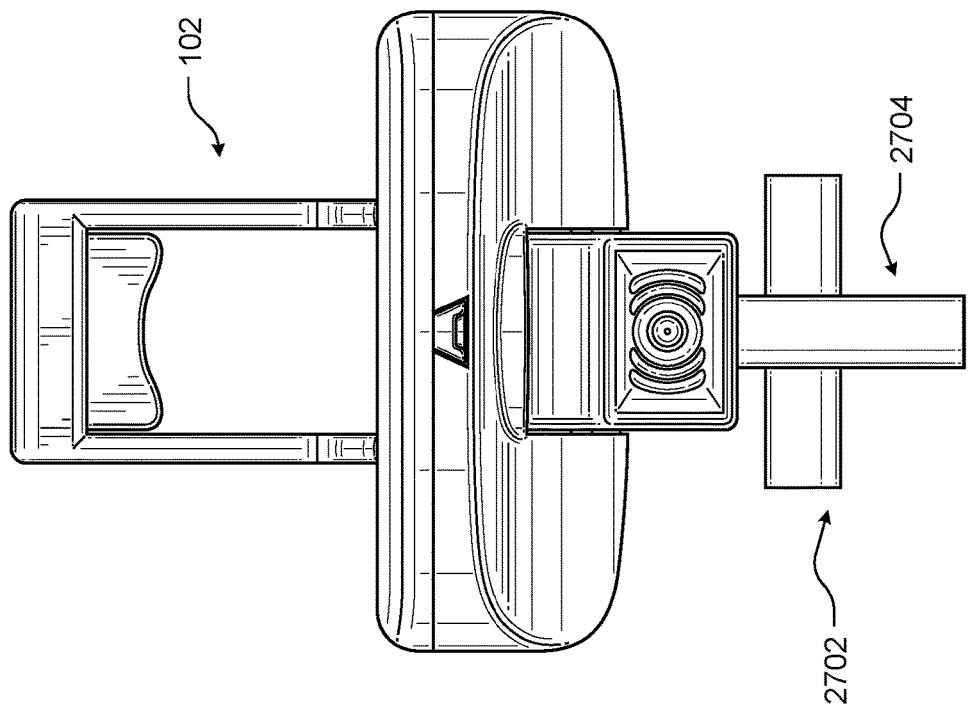
FIG. 29B depicts an example back view of a slide of the adjustable finger splint of FIG. 27 according to some implementations.
Figure 29A:
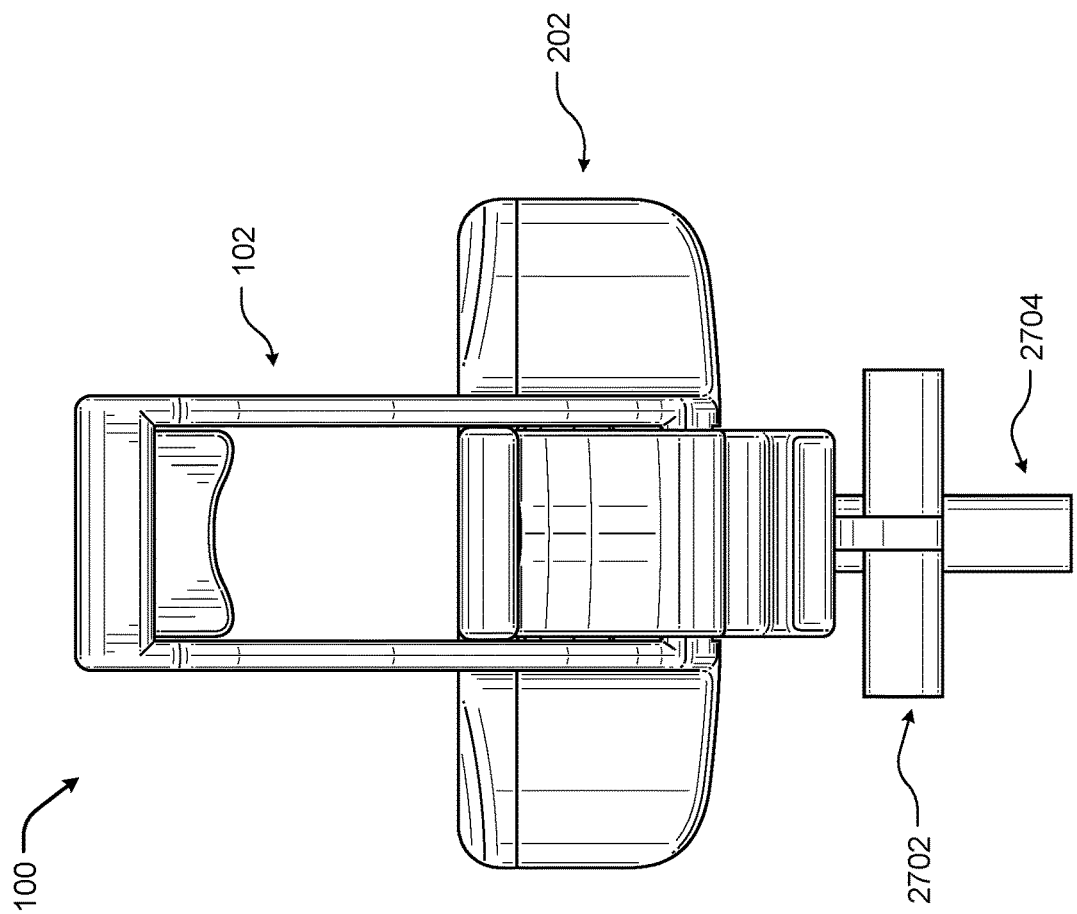
FIG. 29A depicts an example front view of the adjustable finger splint of FIG. 27 according to some implementations.

FIG. 29A depicts an example front view and FIG. 29B depicts an example back view of the adjustable finger splint 100 of FIG. 27 according to some implementations. As discussed above, the slide 104 may include the handle 2702 to assist a third-party individual in operating the finger splint 100. In this example, the handle 2702 extends to both the right and left of the wedge 404. In the current example, the extensions of the handle 2702 are less wide than the width of the MCP platform 202. However, in other examples, it should be understood that the length and width of the extensions of the handle 2702 may vary, for instance, the extensions may extend past the outer edges of the MCP platform 202.

The main body 102 also includes a stabilizing portion 2704 that may be gripped by the third-party individual when pulling on the handle 2702. In the current example, the stabilizing portion 2704 is shown as a rounded handle. But it should be understood, that the stabilizing portion 2704 may take other forms, such as a gripped handle, weighted portion that may rest on a table or other surface, etc.

Figure 30:
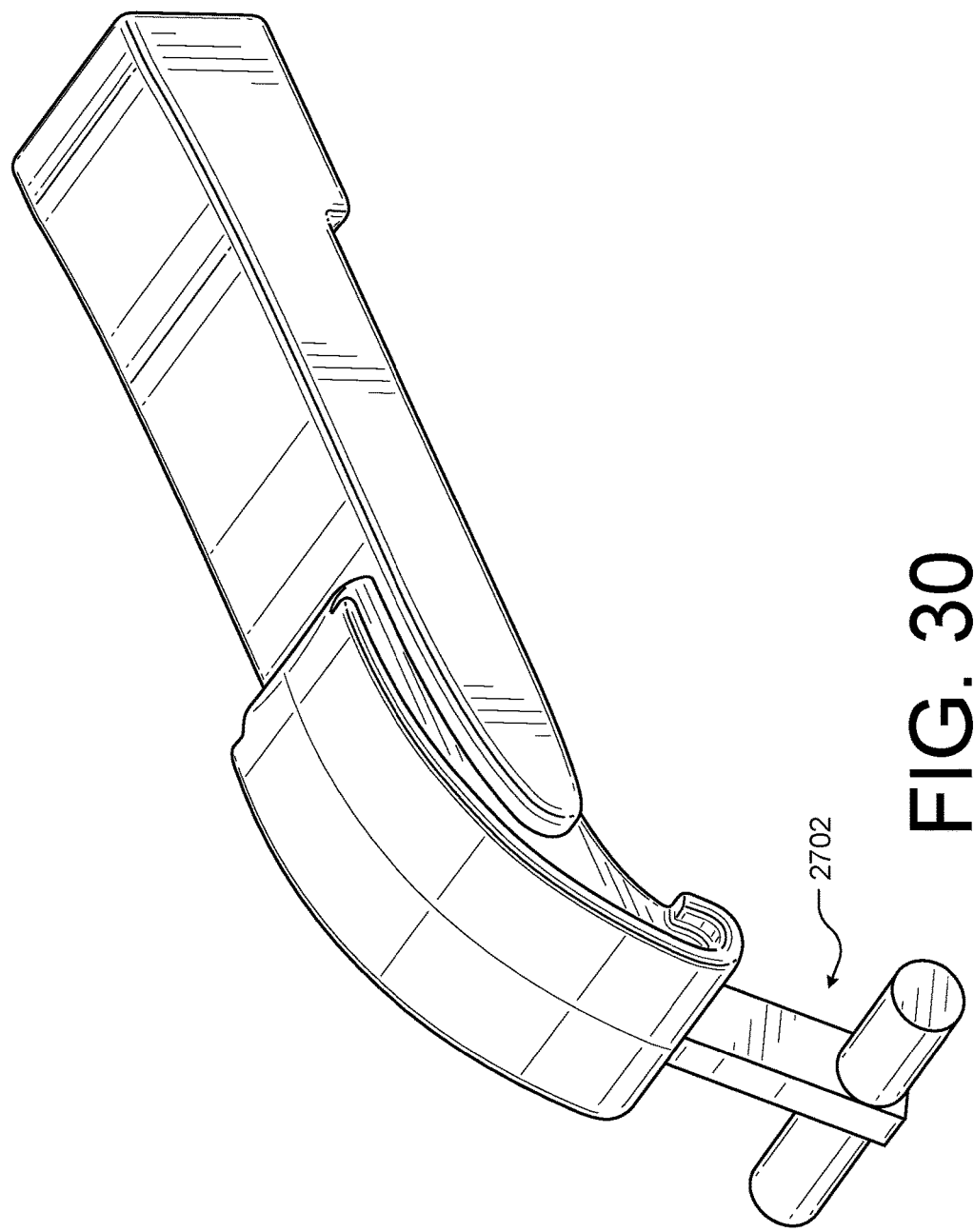
FIG. 30 depicts an example perspective view of the slide of the adjustable finger splint of FIG. 27 according to some implementations

FIG. 30 depicts an example perspective view of the slide of the adjustable finger splint of FIG. 27 according to some implementations. As discussed above, the slide 104 may include the handle 2702 to assist a third-party individual in operating the finger splint 100. In this example, the handle 2702 extends to both the right and left of the wedge 404. In the current example, the extensions of the handle 2702 are less wide than the width of the MCP platform 202. However, in other examples, it should be understood that the length and width of the extensions of the handle 2702 may vary, for instance, the extensions may extend past the outer edges of the MCP platform 202.

Figure 31:
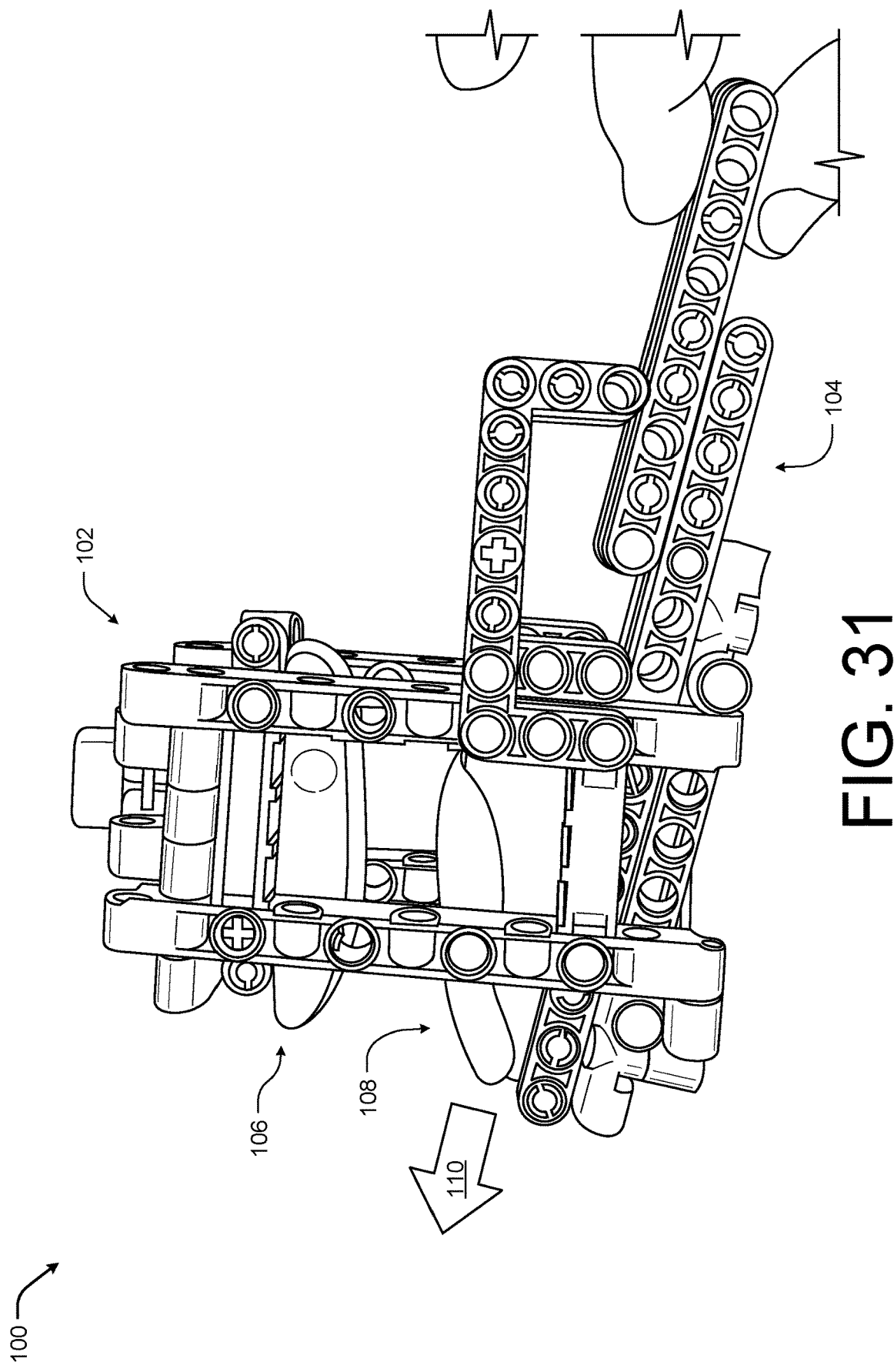
FIG. 31 depicts an example embodiment of an adjustable finger splint according to some implementations.

FIG. 31 depicts an embodiment of an adjustable finger splint 100. The adjustable finger splint 100 may comprise a main body 102, a slide 104, a dorsal pad 106, and a palmar pad 108, as discussed above. As illustrated, the slide 104 and the palmar pad 108 are movable relative to the main body 102 and the dorsal pad 106, such that as the slider is moved in a direction indicated by 110, the finger of the user is increasingly straightened relative to the hand. In this manner, the user may control the amount of pressure applied based on the user's comfort level.

Figure 32:
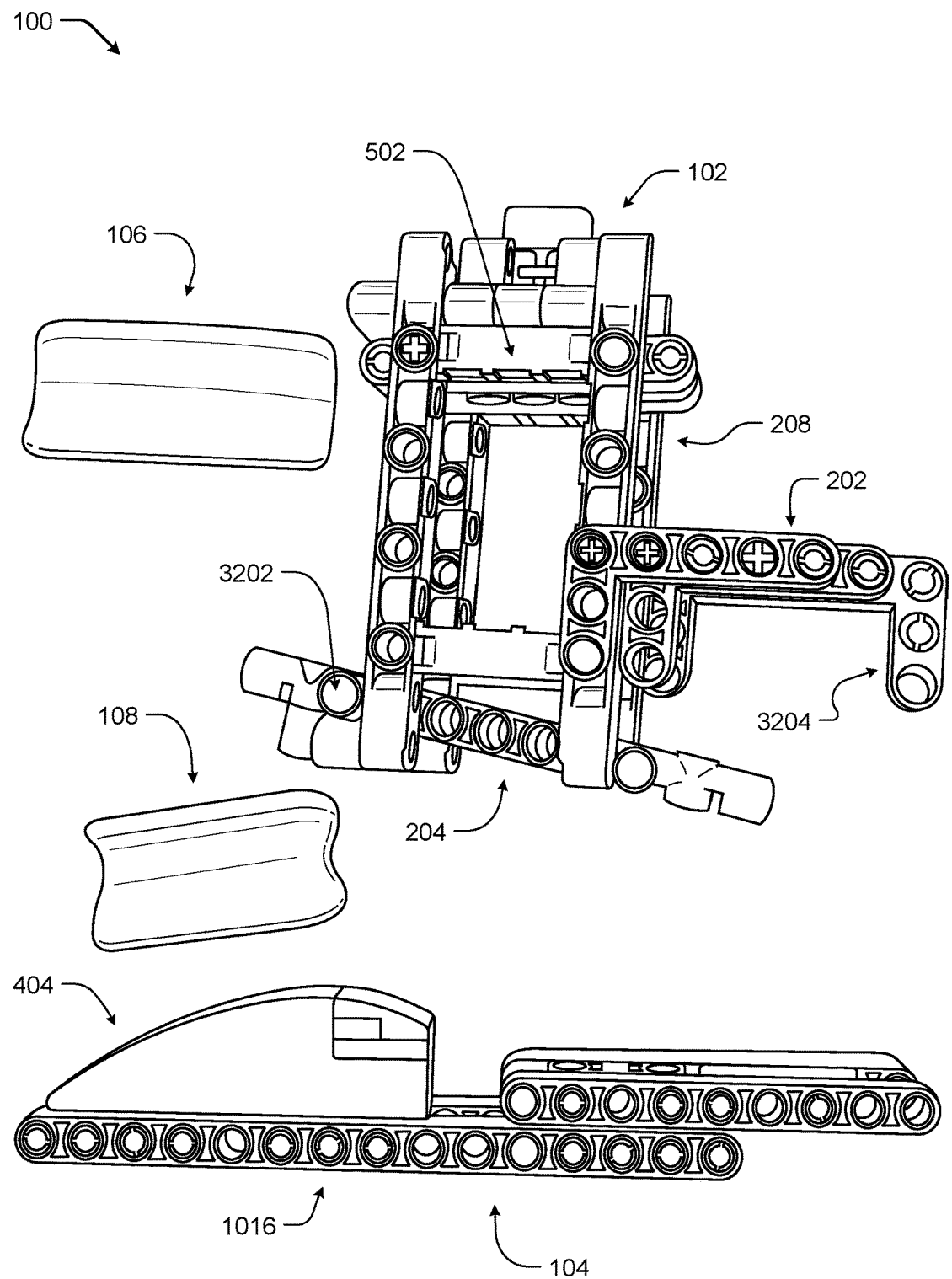
FIG. 32 depicts an example embodiment of an adjustable finger splint having releasable components according to some implementations.

FIG. 32 depicts the main body 102, the slide 104, the dorsal pad 106, and the palmar pad 108 separated from one another. As shown in FIG. 32, the main body 102 can have a frame 208 including a slide platform 204, a MCP platform 202, and a PIP platform 502. The slide 104 can comprise a wedge 404 and a slide rail 1016.

The slide platform 204 can be positioned at or near the bottom of the frame 208 and can extend along at least a portion of the main body. In some embodiments, the slide platform 204 can be coupled with the frame 208 via an adjustable hinge 3202, such that the angle of the slide platform 204 relative to the frame 208 can be adjusted. As will be discussed below, the slide rail 1016 of the slide 104 can slide along the slide platform 204 during use.

The MCP platform 202 can extend out behind the frame 208 at a position above the height of the slide platform 204, such that at least a portion of the slide rail 1016 of the slide 104 can fit between the top of the slide platform 204 and bottom of the MCP platform 202, as discussed above. In some examples, at least a portion the MCP platform 202, such as an MCP extension 3204 protruding downward from the MCP platform 202, can contact the slide rail 1016 of the slide 104 during use, thereby helping to keep the slide 104 in place within the main body 102. As will be discussed below, a user's MCP joint can contact the top of the MCP platform 202 during use.

The PIP platform 502 can be positioned at the top of or supported by the frame 208. The dorsal pad 106 can be coupled to the underside of the PIP platform 502, as discussed above. The PIP platform 502 and dorsal pad 106 can be positioned above the height of the MCP platform 202, such that a user's finger can be inserted into a space between the MCP platform 202 and the dorsal pad 106. During use, the top of a user's PIP joint can contact the underside of the dorsal pad 106 when the user's finger is inserted into the adjustable finger splint 100.

During use, the slide rail 1016 of the slide 104 can be moved along the slide platform 204 of the main body 102, such that the slide 104 is movable relative to the main body 102. In some examples, the slide rail 1016 and the slide platform 204 can be slideably coupled with each other, such as by having a protrusion in one of the slide rail 1016 or the slide platform 204 notched into a groove that extends along the other one of the slide rail 1016 or the slide platform 204.

The wedge 404 can be coupled to the top of the slide rail 1016. However, in the current example, the wedge 404 may be releasably coupled to the slide rail 1016, such that wedges 404 having different curvatures may be used in conjunction of the splint 100 to treat an injured finger. The top of the wedge 404 can be shaped with a curvature, as discussed above. The slide 104 can be moved along the slide platform 204 to adjust the position of the wedge 404 relative to a finger inserted into the adjustable finger split 100.

In this example, the palmar pad 108 rests on the wedge 404 or be coupled with the wedge 404, such that the bottom of a user's DIP joint contacts the palmar pad 108 above the wedge 404 during use. The palmar pad 108 can slide along the curvature of the top of the wedge 404, such that the palmar pad 108 can maintain contact with a user's DIP joint as the wedge 404 moves underneath the palmar pad 108. In some examples, the palmar pad 108 can be separate from the wedge 404 and be held in place against the wedge 404 by the presence of the user's finger. In other examples, the palmar pad 108 can be slideably coupled with the wedge 404, such as by having a protrusion in one of the palmar pad 108 or wedge 404 notched into a groove that extends along the other one of the palmar pad 108 or wedge 404.

Although in some embodiments the elements of the PIP platform 502 can be fixed in position on the frame 208, in other embodiments components of the PIP platform 502 can be moveable and/or openable to make it easier to insert a finger into the adjustable finger splint 100 or to remove a finger from the adjustable finger splint 100.

Additionally, the main body 102, the slide 104, the dorsal pad 106, and the palmar pad 108 are shown as releasable components of the adjustable finger splint 100. However, it should be understood that one or more of the components 102-108 may be formed as a single component. For example, the palmar pad 108 may be secured to the slide 104 via a tongue and groove coupling, to allow the palmar pad 108 to move independently from the slide 104 along the length of the curvature of the wedge 404. In another example, the slide 104 may be coupled over the slide platform 204 in a manner that the slide 104 may move independently along the length of the slide platform 204 during use but remain coupled when a finger is not engaged with the finger splint 100.

As shown in FIGS. 33A-33F, in some of these moveable and/or openable embodiments, the PIP platform 502 can have a moveable panel 3302, one or more buckle elements 3304, and a latch 3306. The moveable panel 3302 and the one or more buckle elements 3304 can be hingeably coupled with the frame 208. The latch 3306 can be on at least one of the buckle elements 3304 and be configured to selectively lock the buckle elements 3304 over the moveable panel 3302. The dorsal pad 106 can be coupled with the underside of the moveable panel, as shown below.

Figure 33A:
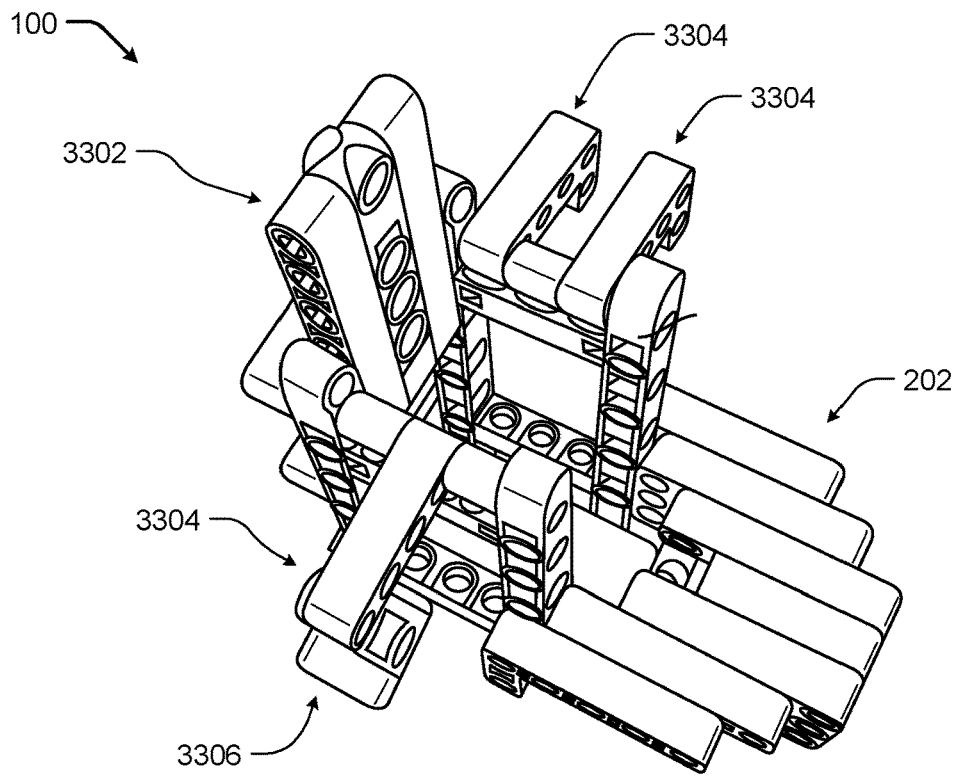
FIGS. 33A-33F depict example views of a PIP panel that can be opened and adjusted according to some implementations.
Figure 33B:
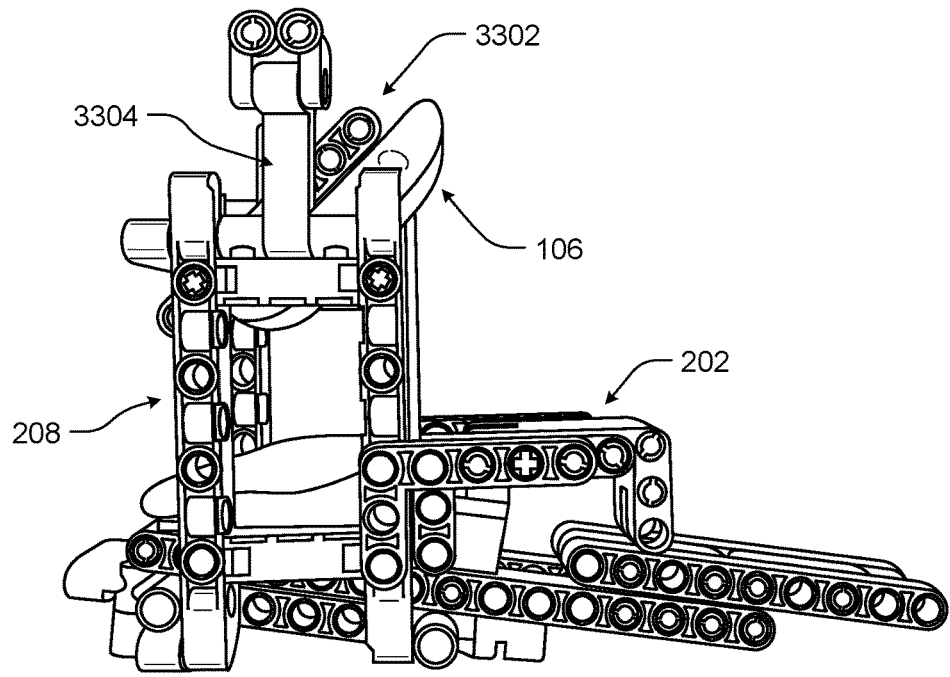

When a finger is to be inserted into the adjustable finger splint 100, the buckle elements 3304 and moveable panel 3302 can be angled upward, as shown in FIGS. 33A and 33B. The PIP platform 502 can thus be opened relative to the MCP platform 202 and/or slide 104, thereby providing more room for a finger to be inserted into the adjustable finger splint 100, as shown in the side view of FIG. 33B. For example, an injured finger with extreme flexion that cannot easily be straightened to fit into the adjustable finger split 100 can be given more room by opening the PIP platform 502 and angling the moveable panel 3302.

Figure 33C:
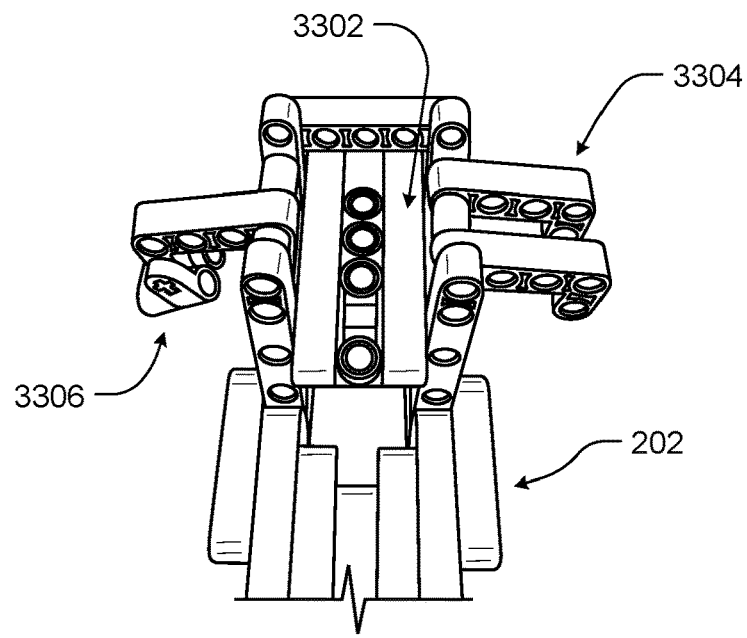
Figure 33D:
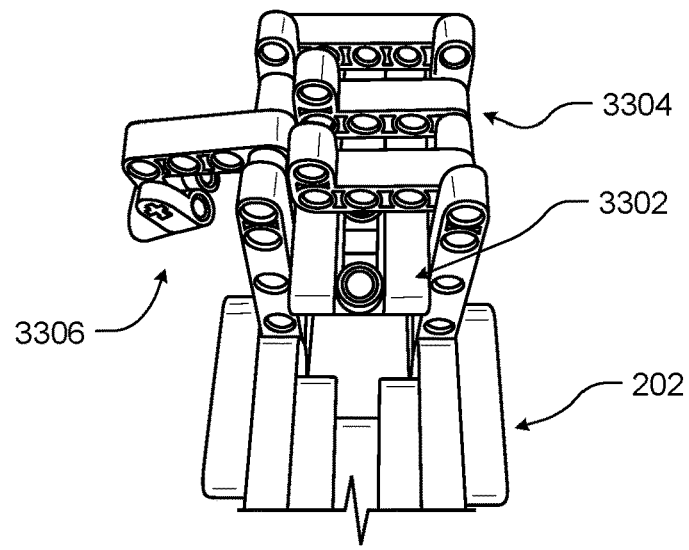
Figure 33E:
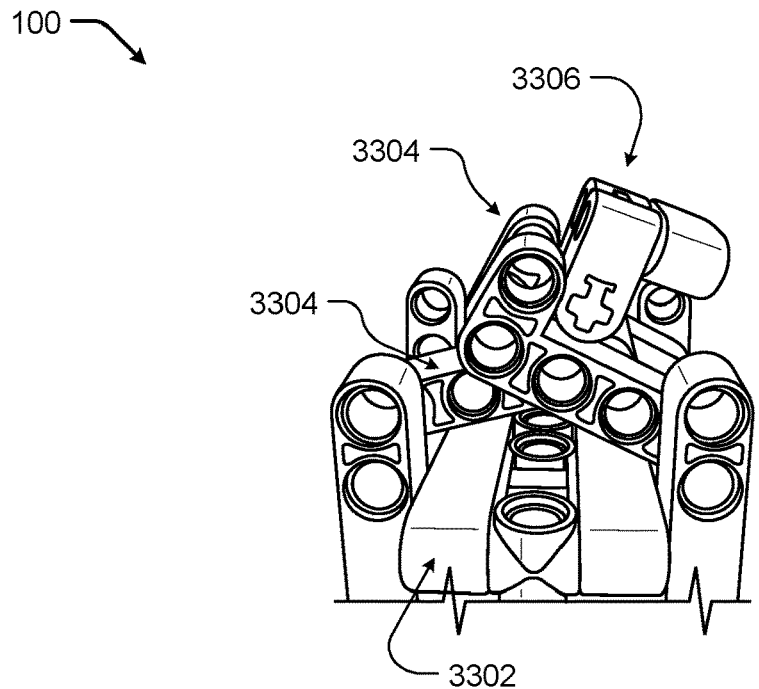
Figure 33F:
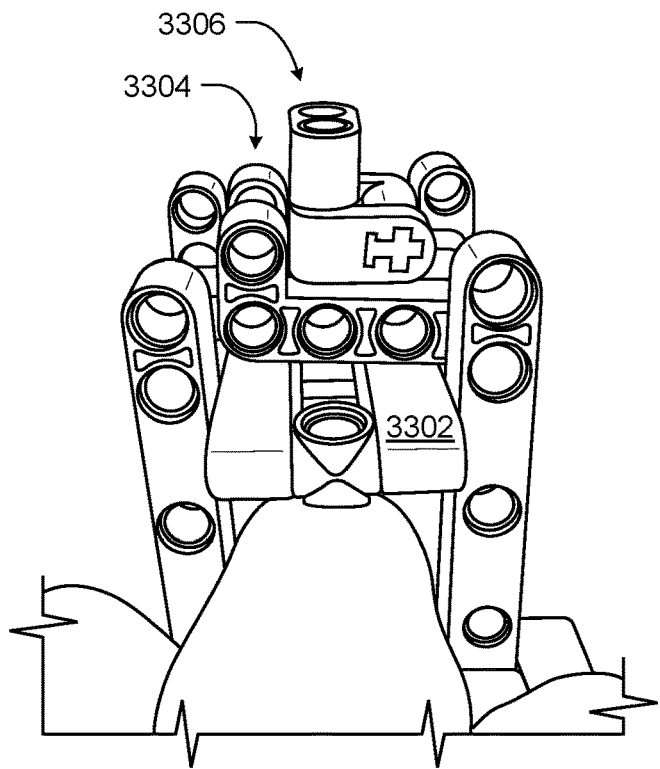

To close the PIP platform 502, the moveable panel 3302 can be lowered as shown in FIG. 33C, and the buckle elements 3304 can then be lowered over the moveable panel 3302 as shown in FIGS. 33D-33E. The latch 3306 than then be used to lock the buckle elements 3304 over the moveable panel 3302 as shown in FIG. 33F.

When the finger is to be removed, the latch 3306 can be released, such as by releasing a tab on the latch 3306, thereby freeing the buckle elements 3304 and moveable panel 3302 to again be angled upward as shown in FIG. 33B such that there is more room to remove a finger from the adjustable finger splint 100.

It should be understood that the examples illustrated in FIGS. 33A-33F, a buckle element 3304 is shown to allow the bent finger of a user to be inserted into the adjustable finger splint 100. However, it should be understood that other types of latches, locks, joints, and openings may be used to allow a bent finger sufficient access to the opening in the adjustable finger splint 100.

Figure 34A:
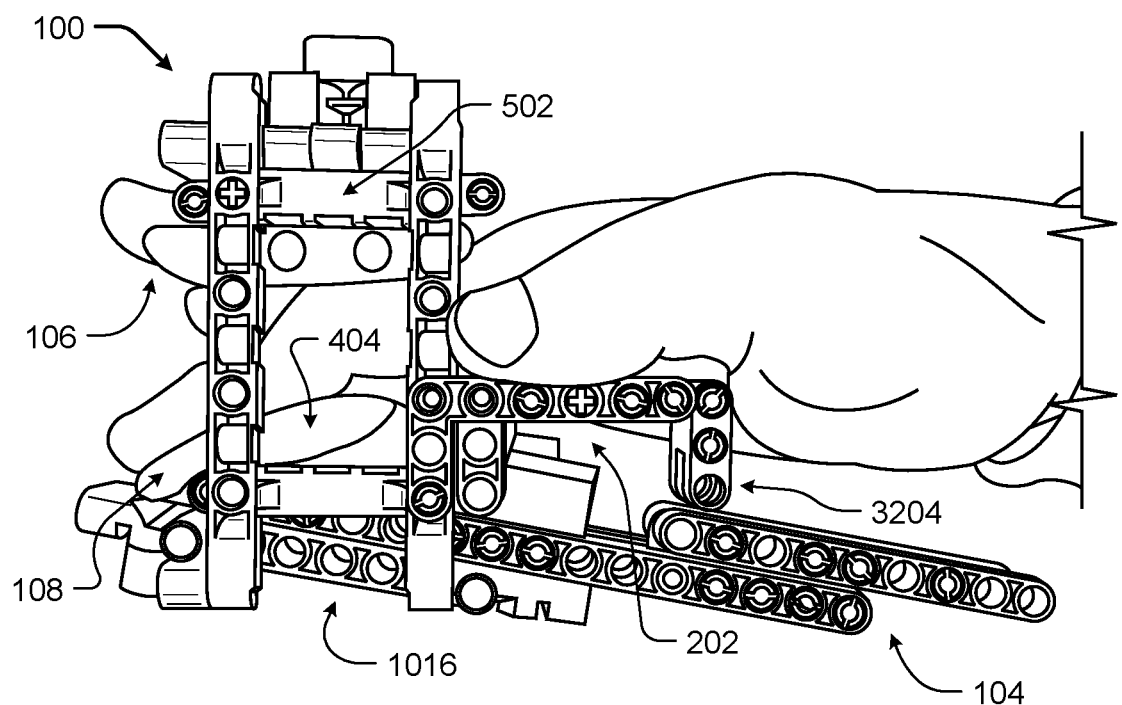
FIGS. 34A and 34B depict example embodiments of an adjustable finger splint in use according to some implementations.
Figure 34B:
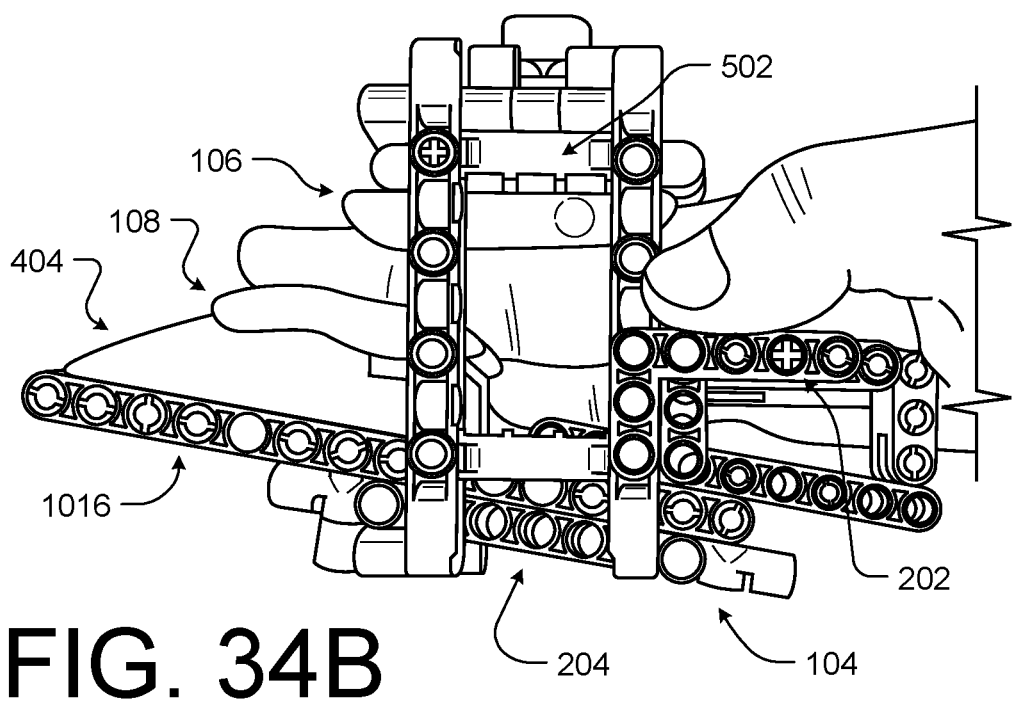

FIGS. 34A and 34B depicts the adjustable finger splint 100 in use. As shown in FIG. 34A, the wedge 404 of the slide 104 can be retracted at least partially into the frame 208 by sliding the slide rail 1016 along the slide platform 204 of the main body 102. A user's finger can then be placed into the adjustable finger splint 100 such that the bottom of the finger's MCP joint contacts the MCP platform 202, the top of the finger's PIP joint contacts the dorsal pad 106 underneath the PIP platform 502, and the bottom of the finger's DIP joint contacts the palmar pad 108 above the wedge 404. As discussed above with respect to FIGS. 33A-33F, in some embodiments the PIP platform 502 can be opened and/or angled to assist with insertion of the finger, followed by closing and locking the PIP platform 502 after the finger is in place.

After a user's finger is in place within the adjustable finger splint 100 with the slide 104 retracted, as shown in FIG. 4A, the slide 104 can be distally extended by sliding the slide rail 212 along the slide platform 204, as shown in FIG. 4B. As the slide 104 is distally extended, the curvature of the wedge 404 can press the finger's DIP joint upward by increasing amounts as the slide 104 slides farther along the slide platform 204. The palmar pad 108 can also move along the top of the wedge 404 and change its incident angle as the slide 104 is distally extended, with the curvature of the wedge 404 causing the angle and position of the palmar pad 108 to match the angle and position of the finger's DIP joint as the wedge 404 moves underneath the palmar pad 108.

In some examples, the main body 102 and/or slide 104 can have a locking mechanism, such as a latch, buckle, or ratchet, that can at least temporarily hold the slide 104 in place relative to the main body 102 once it has been distally extended and positioned for treatment of an inserted finger. In other examples, the force of an inserted finger pressed against the palmar pad 108 and wedge 404 and/or the contact of the slide rail 1016 against the MCP extension 3204 or other portion of the MCP platform 202 can help maintain the slide 104 in place during treatment.

Figure 35:
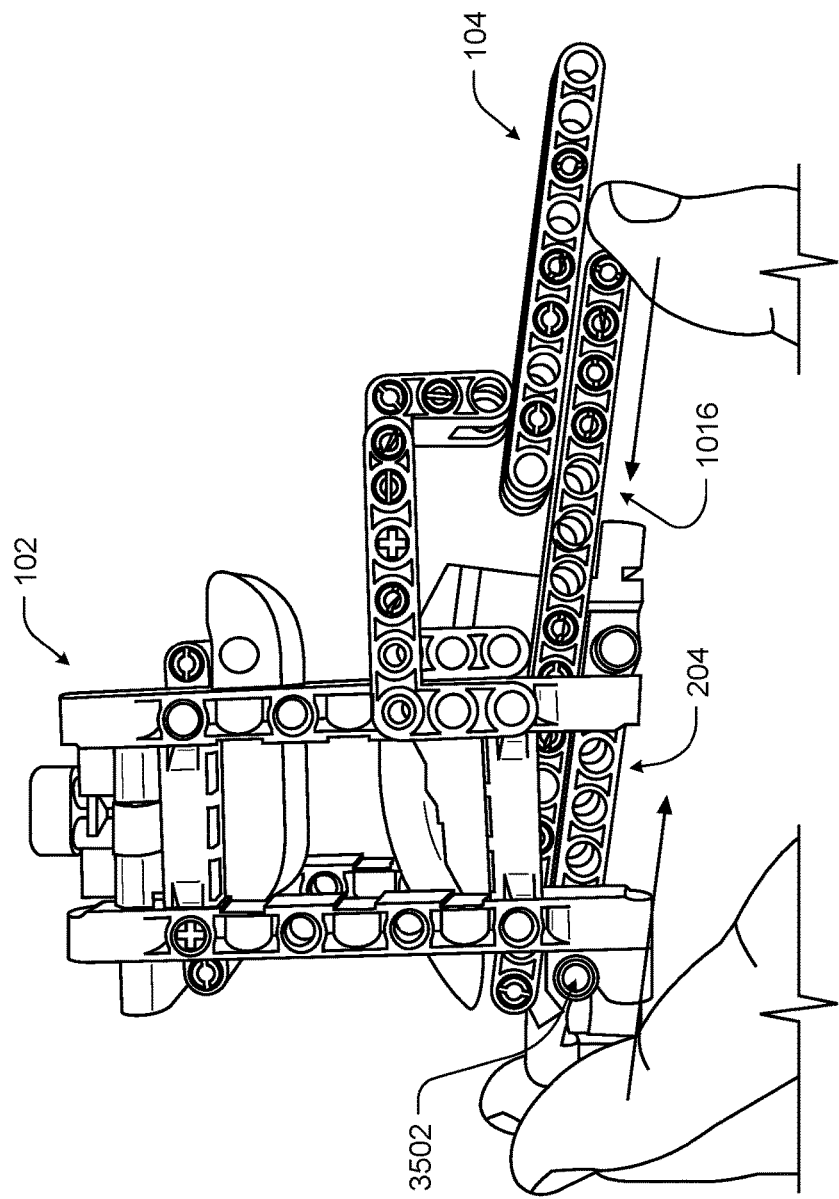
FIG. 35 depicts example forces used to operate an adjustable finger splint according to some implementations.

As shown in FIG. 35, the slide 104 can be extended from the main body 102 by squeezing the back of the slide rail 1016 and the front of the slide platform 204, thereby pushing the slide 104 along the slide platform 204. Such a squeezing motion provide forces in opposing directions that are substantially parallel to the finger within the adjustable finger splint 100. Such opposing parallel forces can have less impact on an injured finger than torque forces introduced by other devices that operate by turning screws to move components.

As noted above, in some examples the slide platform 204 can be moveable relative to the rest of the main body 102 via a hinge 3502, such that the angle of the slide platform 204 and the slide 104 can be adjusted. The angle of the slide 104 can therefore be adjusted in order to treat different injuries of different types and/or severities. For example, in FIGS. 34A and 34B, the slide platform 204 is angled upward so that the slide 104 can be positioned to treat an interphalangeal joint from about 40° flexion to about 10° hyperextension. However, the slide platform 204 can also be positioned to be flat or angled downward to position the slide 104 for treatment of more severely contracted joints. In examples in which the PIP platform 502 can be angled and/or opened, as discussed above with respect to FIGS. 33A-33F, the PIP platform 502 can be unlatched to allow a finger to be inserted or removed without adjusting the angle of the slide platform 204 and slide 104.

FIGS. 36A-D depicts an example views of an adjustable finger splint 100 with adjustable proximal interphalangeal platform 502 according to some implementations. In some situations, the dorsal pad 106 may need to be customized to the individual being treated and/or the shape of the dorsal pad 106 may be adjusted during treatment to gradually allow the injured finger to achieve an extended or straightened position. For example, an injured individual may start treatment with a dorsal pad 106 with an arc similar to that of FIG. 36B, reach a mid-way point and continue treatment with dorsal pad 106 of FIG. 36C, and then complete the treatment with a dorsal pad of FIG. 36D. Thus, the dorsal pad 106 eventually is substantially horizontal and allows the finger to fully extend at a period of time nearing the completion of treatment.

In these examples, the PIP platform 502 is also configured to releasably couple or decouple from the frame 208. In this example, the PIP platform 502 may include mating components 3602 configured to mate with paired mating components 3604 on the frame 208. For instance, a user may pinch or apply inward pressure on the bottom of the PIP platform 502, align the mating components 3202 and 3204, and release to position the PIP platform 502 with the frame 208. In some cases, the relative position of the PIP platform 502 with the frame 208 may be adjusted based on characteristics of the finger being treated. For example, the PIP platform may be tilted forward or backward relative to the frame 208. As one illustrative example, the PIP platform 502 may be initially tilted forward and adjusted backward toward an upright configuration as treatment progresses.

Figure 37:
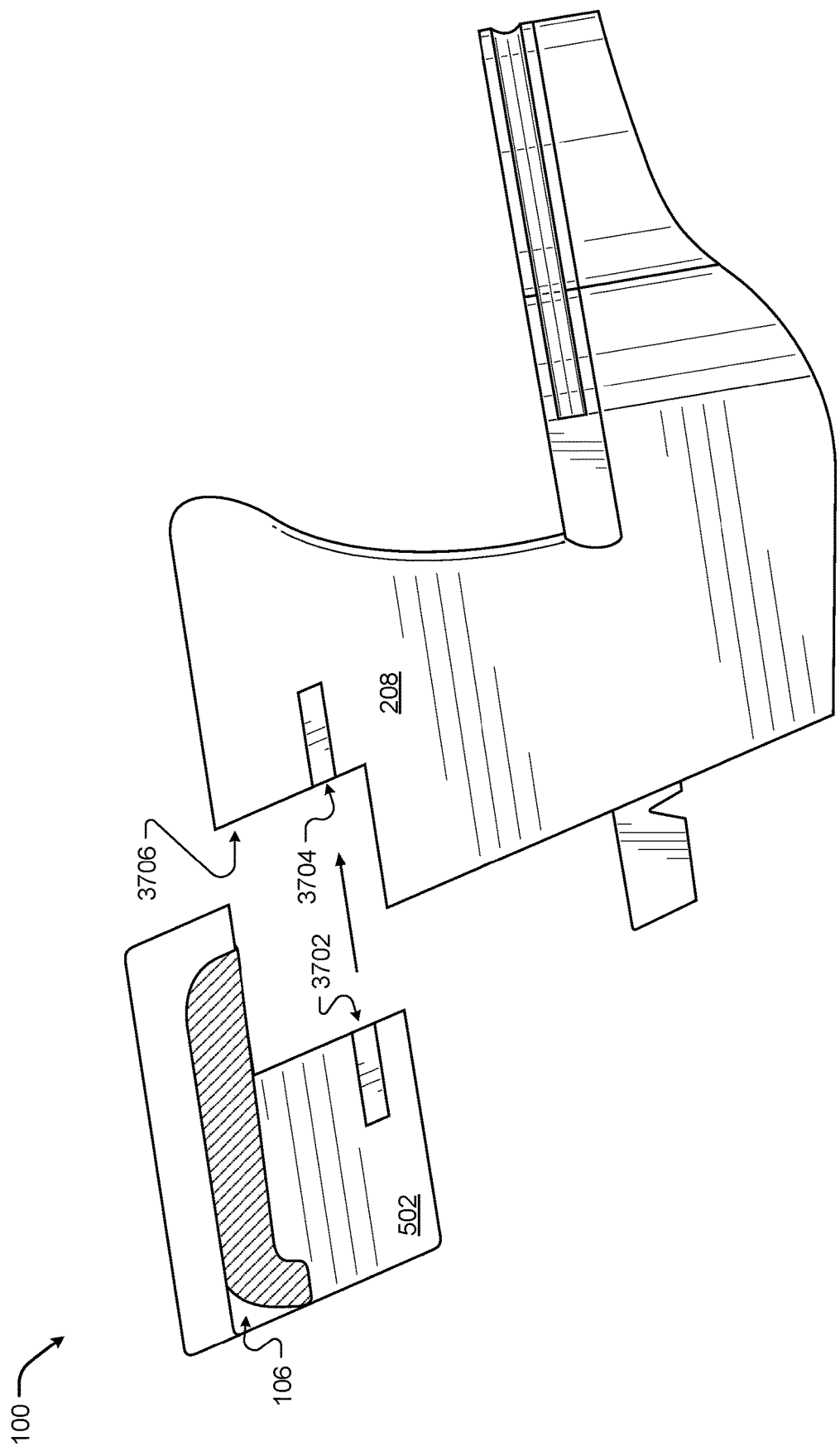
FIG. 37 depicts an example side view of an adjustable finger splint with adjustable proximal interphalangeal platform according to some implementations.

FIG. 37 depicts an example side view of an adjustable finger splint 100 with adjustable proximal interphalangeal platform 502 according to some implementations. In the illustrate example, the frame 208 is again releasably coupled to the PIP platform 502. However, in this example the PIP platform 502 may slide in a lock with the frame 508 using the mating components 3702 and 3704.

Figure 38:
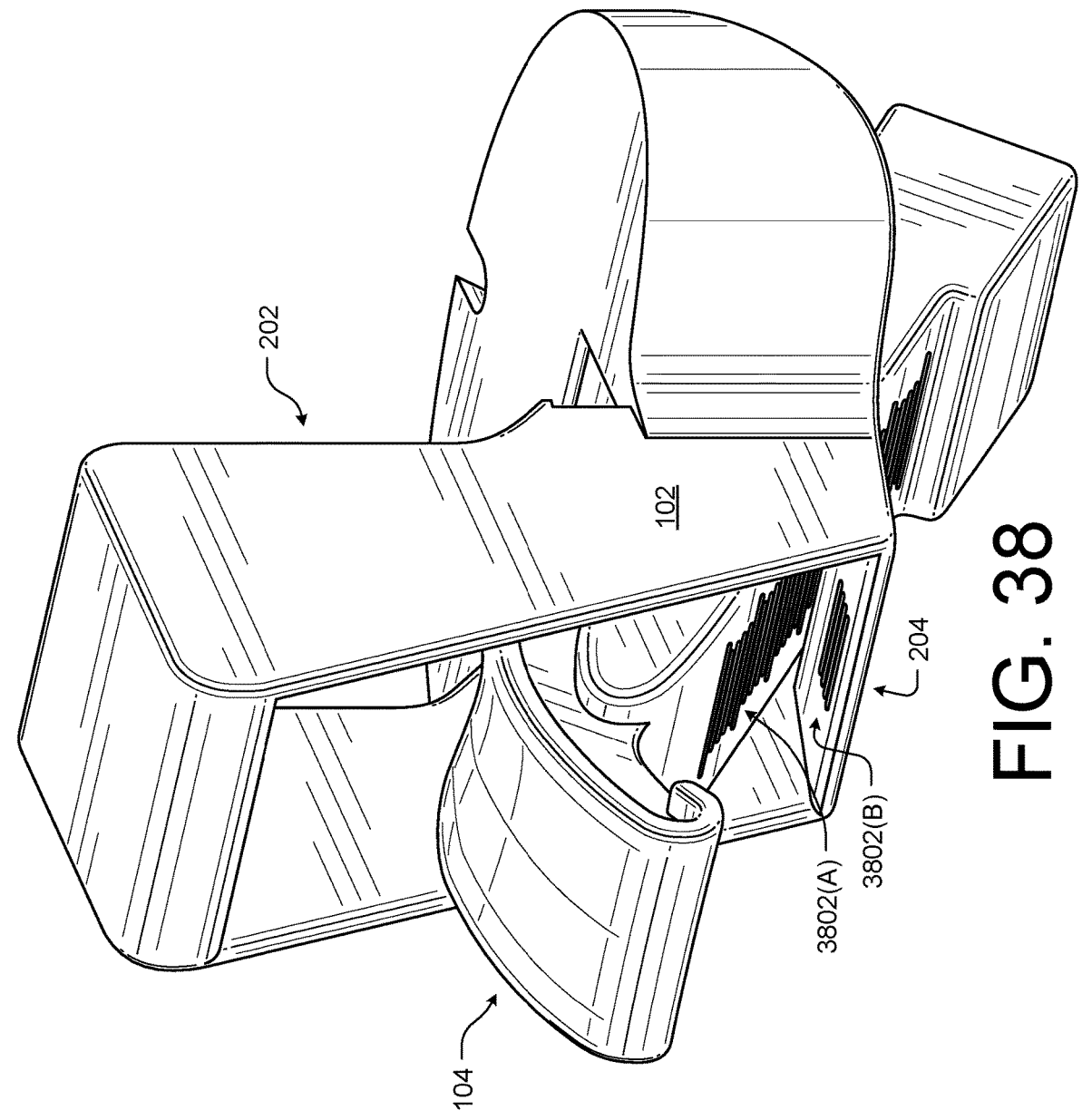
FIG. 38 depicts an example perspective view of an adjustable finger splint with ratchet locking system according to some implementations.

FIG. 38 depicts an example perspective view of an adjustable finger splint 100 with ratchet locking system 3802 according to some implementations. In this example, the slider 104 includes female ratchet components 3802(A) and the slider platform 204 of the main body 102 includes mating male ratchet components 3802(B). In this example, as the user move the slider 104 forward, the female ratchet components 3802(A) move over the male ratchet components 3802(B) due to the force applied by the user. When the user releases the slider 104 the female ratchet components 3802(A) aligned with the male ratchet components 3802(B) mate and lock together. When mated, the ratchet locking system 3802 is able to provide additional friction to hold the slider 104 at the desired position relative to the main body 102 to better maintain desired pressure on the injured finger.

It should be understood, that while the current example includes a ratchet system 3802, other types of locking systems may be utilized, such as a screw based system, lever based system, or crank based system, and the exact position of the locking system may be move, for example place along the inner surface of the walls of the frame 208 rather than along the top surface of the slider platform 204.

Figure 39:
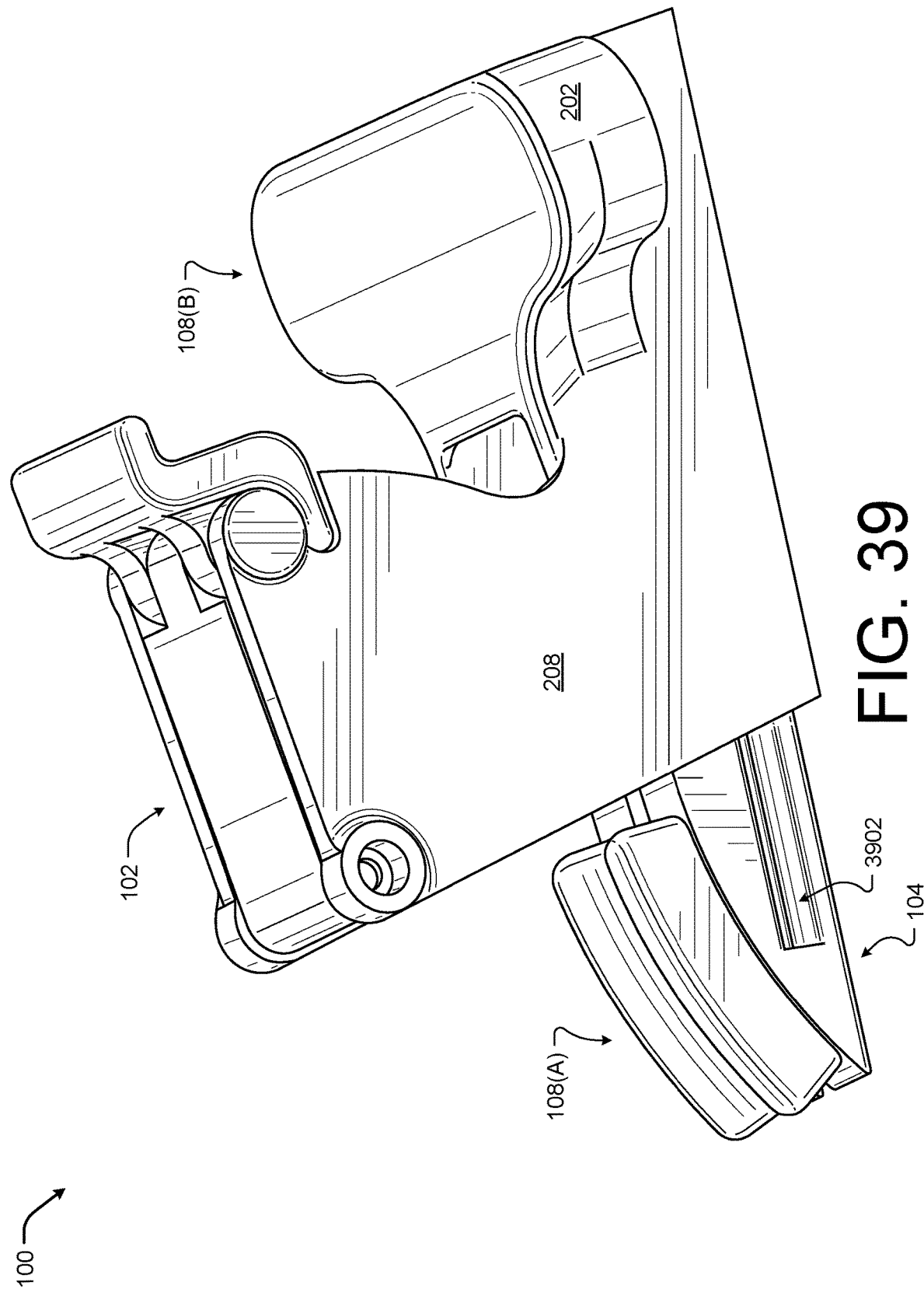
FIG. 39 depicts an example perspective view of an adjustable finger splint with a two-part palmar pad and guided slide according to some implementations.

FIG. 39 depicts an example perspective view of an adjustable finger splint 100 with a two-part 108(A) and 108(B) palmar pad 108 and guided slide 104 according to some implementations. In the current example, the palmar pad 108 is divided into two parts, the front portion 108(A) and rear portion 108(B). The front portion 108(A) is coupled to the slide 104 and the rear portion 108(B) is coupled to the MCP platform 202. In the current example, the slide 104 is also coupled to a guide along the inner walls (not shown) of the frame 208. For instance, the slide 104 may include a groove 3902 that mates with the guide on the frame 208. The mated guide and groove 3902 may allow the slide 104 to be maintained along a desired path with respect to the main body 102 during treatment.

Figure 40:
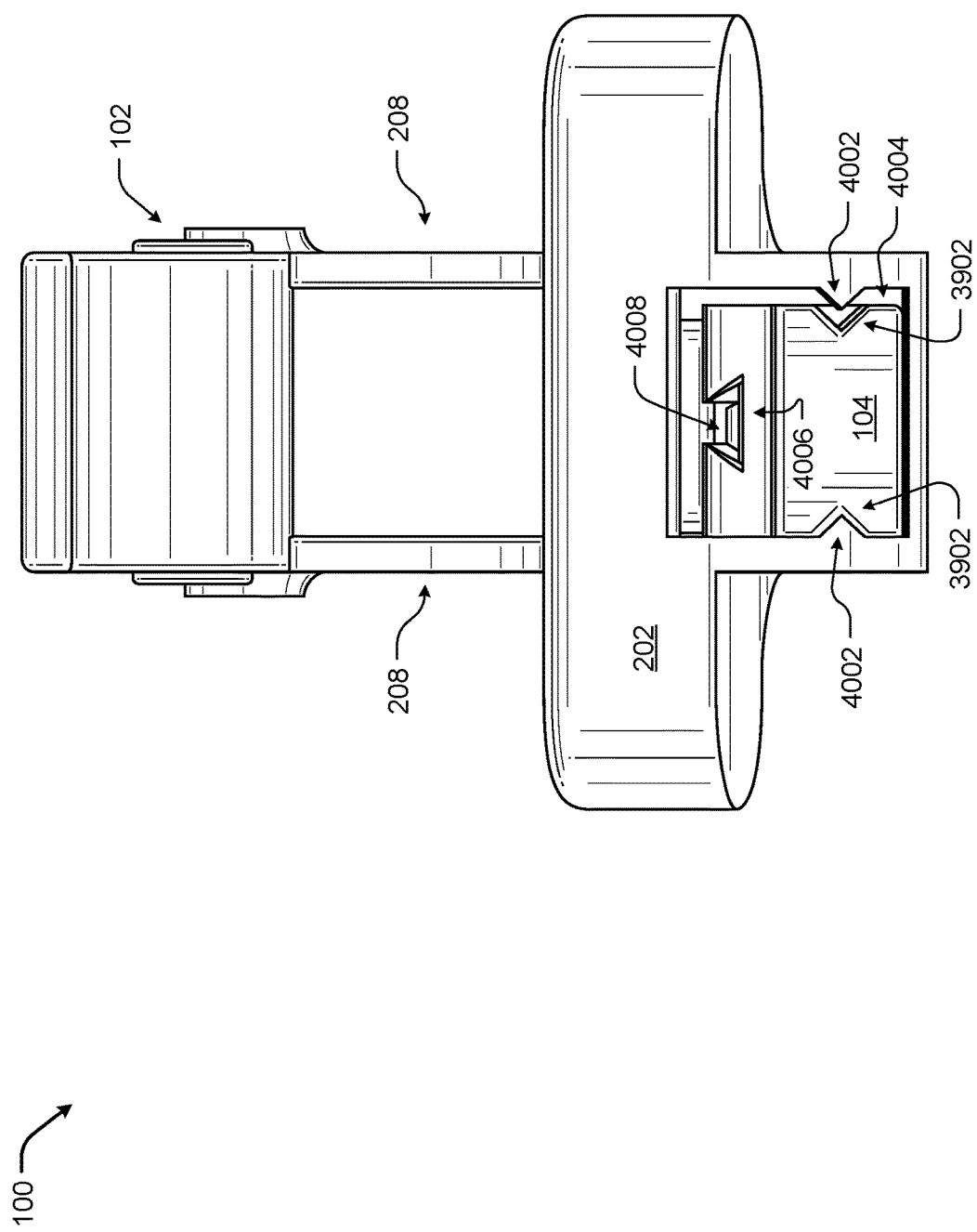
FIG. 40 depicts an example back view of an adjustable finger splint with a guided slide according to some implementations.

FIG. 40 depicts an example back view of an adjustable finger splint 100 with a guided slide 104 according to some implementations. As illustrated, the slide 104 includes grooves 3902 along the left-hand and right-hand walls that substantially mirror guides 4002 along the inner walls of the frame 208. As shown, a gap 4004 may separate the slide 104 from the main body 102 and allow the slide 104 to move relative to the main body 102 while the grooves 3902 and the guides 4002 maintain a path of the slide 104 with respect to the main body 102. In this example, a top groove 4006 along a top surface of the slide 104 and a corresponding guide 4008 along the main body 102 may also assist in maintaining the path of the slide 104 with that of the main body 102. In some cases, the top groove 4006 may also the slide 104 to move or slide within or be slideably coupled to the slide 104.

Figure 41:
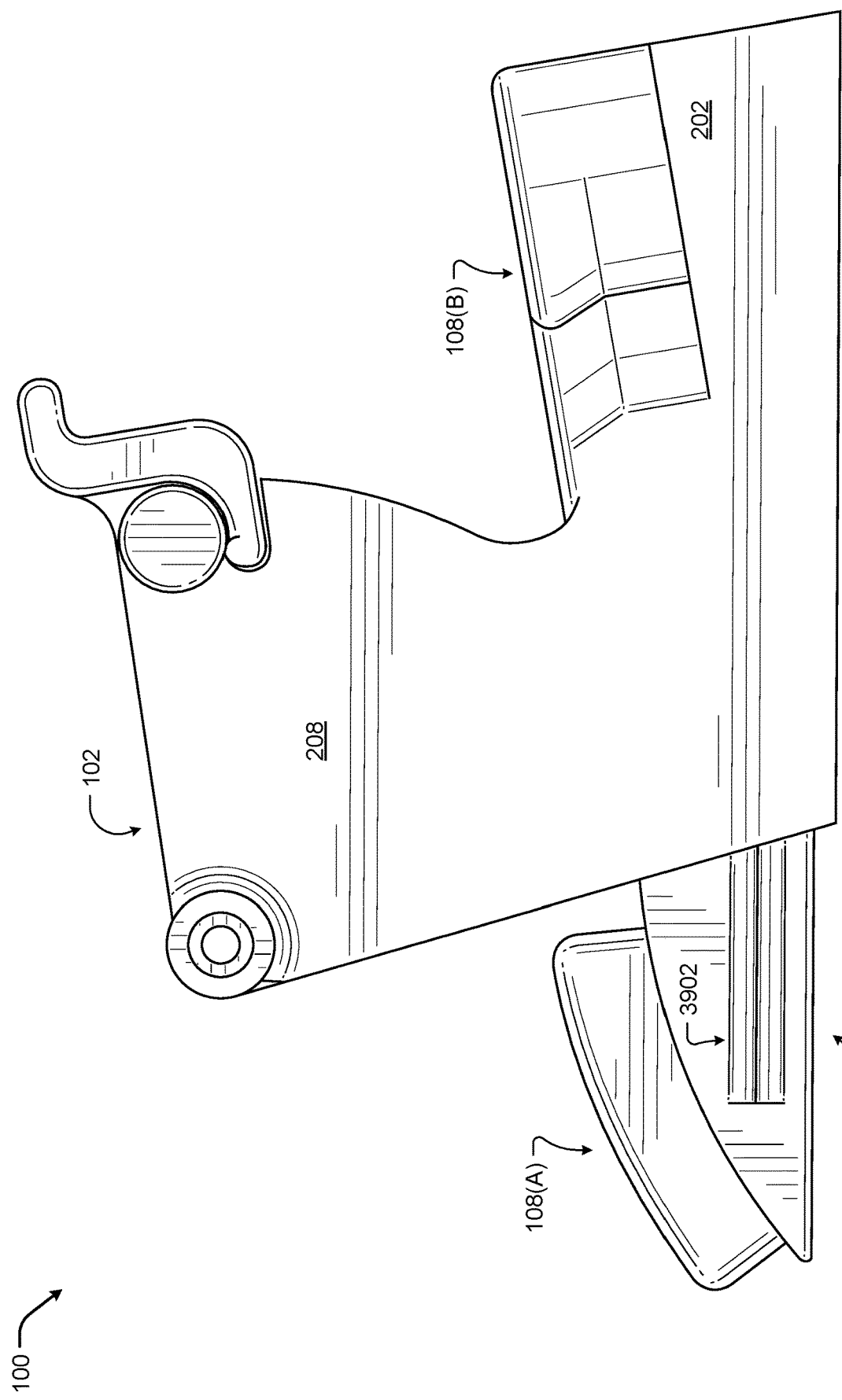
FIG. 41 depicts an example side view of an adjustable finger splint with a two-part palmar pad and guided slide according to some implementations.

FIG. 41 depicts an example side view of an adjustable finger splint 100 with a two-part palmar pad 108 and guided slide 104 according to some implementations. In the current example, the palmar pad 108 is divided into two parts, the front portion 108(A) and rear portion 108(B). The front portion 108(A) is coupled to the slide 104 and the rear portion 108(B) is coupled to the MCP platform 202. In the current example, the slide 104 is also coupled to a guide along the inner walls (not shown) of the frame 208. For instance, the slide 104 may include a groove 3902 that mates with the guide on the frame 208. The mated guide and groove 3902 may allow the slide 104 to be maintained along a desired path with respect to the main body 102 during treatment.

Figure 42:
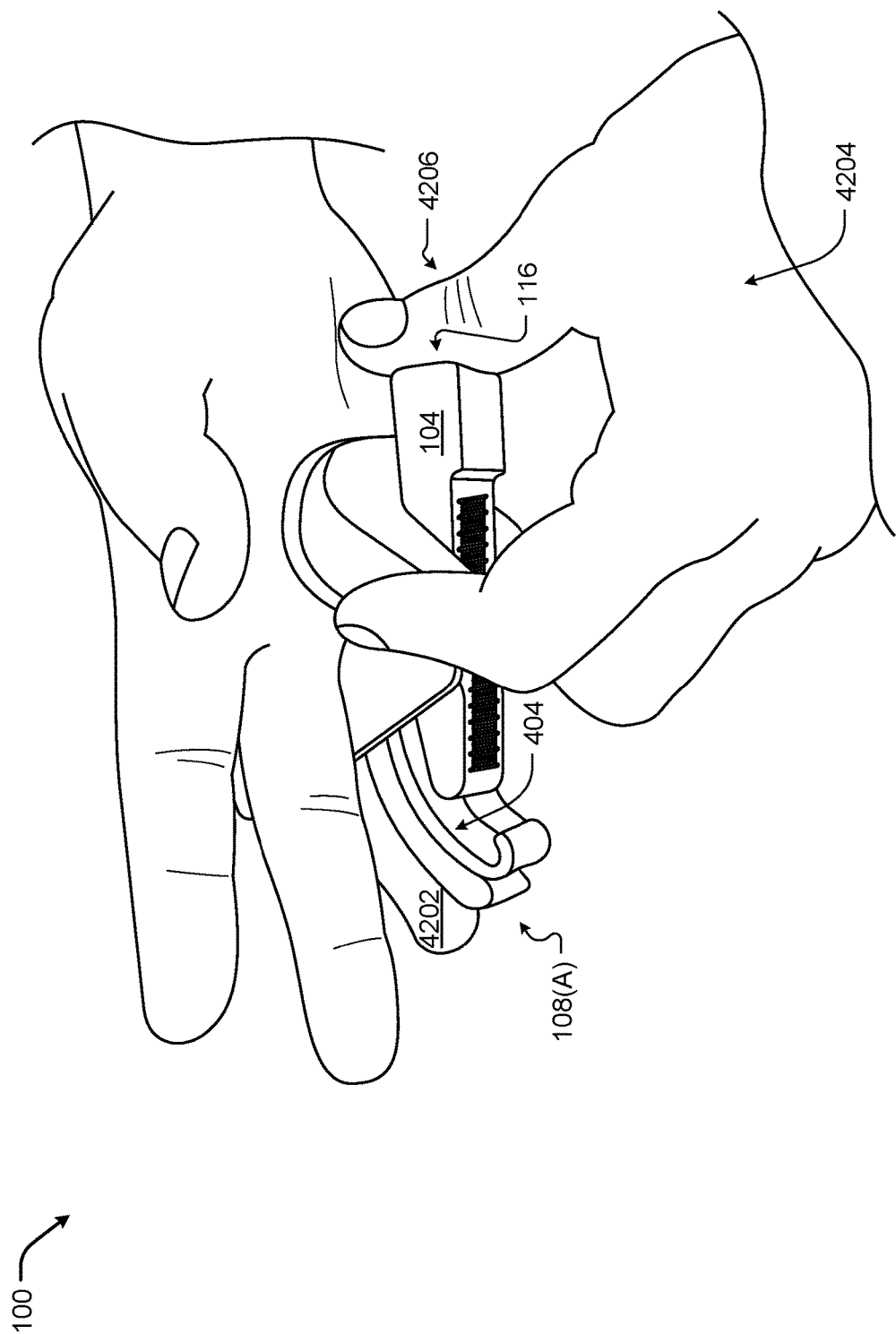
FIG. 42 depicts an example pictorial view of an adjustable finger splint in use according to some implementations.

FIG. 42 depicts an example pictorial view of an adjustable finger splint in use according to some implementations. As discussed above with respect to FIGS. 3 and 4, the user may apply forward pressure on the back end 116 of the slide 104 to cause the slide 104 to engage an injured finger 4202 with the front portion of the palmar pad 108(A). In this example, the user 4204 may apply pressure to the slide 104 via the thumb 4206. In this manner, the user 4204 is able to control the amount of pain caused by the treatment and, in some situations, to remove the hand from the splint 100, allowing the user 4204 use of the hand and a break from the pain.

Although the subject matter has been described in language specific to structural features and/or methodological acts, it is to be understood that the subject matter is not necessarily limited to the specific features or acts described above. Rather, the specific features and acts described above are disclosed as example embodiments.

What is claimed is:

1. An adjustable finger splint comprising:
   a main body including:
      a metacarpophalangeal (MCP) platform having at least one front surface to allow a user to apply a first pressure to the adjustable finger splint; and
      a frame coupled to the MCP platform, the frame extending upward from the main body and defining a cavity, the cavity to receive a finger; and
   a slide to releasably couple to the main body within the cavity to allow the slide to move relative to the main body, the slide defining a wedge having a predefined curvature and a back surface to allow the user to apply a second pressure to the adjustable finger splint, the second pressure in a direction substantially opposite the first pressure.

2. The adjustable finger splint as recited in claim 1, wherein the cavity includes:
   a front opening along a front side of the frame;
   a finger opening along a back side of the frame, the back side opposite the front side; and
   a slide opening along the back side of the frame, the slide opening separate from the finger opening by the MCP platform.

3. The adjustable finger splint as recited in claim 1, further comprising a palmar pad releasably coupled to a top surface of the MCP platform.

4. The adjustable finger splint as recited in claim 3, wherein the palmar pad includes a front portion that extends at least partially into the cavity and a back portion in contact with the top surface of the MCP platform.

5. The adjustable finger splint as recited in claim 3, wherein a top surface of the slide is configured to contact the palmar pad during use.

6. The adjustable finger splint as recited in claim 1, wherein the frame includes a proximal interphalangeal (PIP) platform, the PIP platform defining a top surface of the cavity.

7. The adjustable finger splint as recited in claim 6, wherein the PIP platform is movable relative to the frame to increase a size of an opening of the cavity.

8. The adjustable finger splint as recited in claim 6, further comprising a dorsal pad releasably coupled to a bottom surface of the PIP platform.

9. The adjustable finger splint as recited in claim 8, wherein the predefined curvature is selected to cause the finger within the cavity to extend during use.

10. The adjustable finger splint as recited in claim 1, wherein the slide includes a slide rail.

11. The adjustable finger splint as recited in claim 1, wherein the slide includes a handle.

12. The adjustable finger splint as recited in claim 1, wherein the main body includes a grip or third-party support.

13. An adjustable finger splint, comprising:
 a main body having a metacarpophalangeal (MCP) platform and a frame, the frame defining a cavity and including two side rails, a proximal interphalangeal (PIP) platform, and a slide platform and the MCP platform including at least one front surface to allow a user to apply a first pressure to the adjustable finger splint; and
 a slide moveable with respect to the main body, the slide having a wedge, a back surface, and a slide rail, the wedge extending outward from the cavity from a first side and the slide rail positioned below the MCP platform and extending outward from the cavity from a second side, the second side of the cavity opposite the first side of the cavity, and the back surface to allow the user to apply a second pressure to the adjustable finger splint, the second pressure in a direction substantially opposite the first pressure.

14. The adjustable finger splint as recited in claim 13, wherein the slide releasably couples to the main body.

15. The adjustable finger splint as recited in claim 13, wherein the slide is irremovably attached to the main body.

16. The adjustable finger splint as recited in claim 13, further comprising:
 a dorsal pad coupled to the PIP platform such that the dorsal pad rests over the human finger during use; and
 a palmar pad coupled to the MCP platform such that the palmar pad rests below the human finger during use.

17. An adjustable finger splint, comprising:
 a main body having:
  a metacarpophalangeal (MCP) platform, the MCP platform having a top surface to support a palm of a user and at least one front surface to allow at least one healthy finger of the user to apply a first pressure to the adjustable finger splint; and
  a frame defining a cavity for receiving an injured finger of the user, the frame including two side rails, a proximal interphalangeal (PIP) platform, and a slide platform;
 a palmar pad releasably coupled to the top surface of the MCP platform;
 a slide moveable with respect to the main body through the cavity, the slide including a wedge and a side rail, the wedge having a predefined curvature and the slide rail including at least one back surface to apply a second pressure to the adjustable finger splint, the second pressure in a direction substantially opposite the first pressure; and
 a dorsal pad releasably coupled to the PIP platforms.

18. The adjustable finger splint as recited in claim 17, further comprising a measuring device to indicate an extension or straightness of the injured finger.

19. The adjustable finger splint as recited in claim 17, further comprising a window in at least one of the side rails.

20. The adjustable finger splint as recited in claim 17, wherein the palmar pad has a first layer formed of a first material and a second layer formed of a second material.

* * * * *